US010786168B2

(12) United States Patent
Brown et al.

(10) Patent No.: US 10,786,168 B2
(45) Date of Patent: Sep. 29, 2020

(54) SYSTEMS AND METHODS FOR ANALYZING ELECTROPHYSIOLOGICAL DATA FROM PATIENTS UNDERGOING MEDICAL TREATMENTS

(71) Applicant: The General Hospital Corporation, Boston, MA (US)

(72) Inventors: Emery N. Brown, Brookline, MA (US); Seong-Eun Kim, Cambridge, MA (US); Michael Behr, Cambridge, MA (US); Demba Ba, Cambridge, MA (US)

(73) Assignees: The General Hospital Corporation, Boston, MA (US); Massachusetts Institute of Technology, Boston, MA (US)

( * ) Notice: Subject to any disclaimer, the term of this patent is extended or adjusted under 35 U.S.C. 154(b) by 0 days.

(21) Appl. No.: 15/826,182

(22) Filed: Nov. 29, 2017

(65) Prior Publication Data

US 2018/0146876 A1    May 31, 2018

Related U.S. Application Data

(60) Provisional application No. 62/427,524, filed on Nov. 29, 2016.

(51) Int. Cl.
*A61B 5/04* (2006.01)
*A61B 5/048* (2006.01)
(Continued)

(52) U.S. Cl.
CPC .......... *A61B 5/04017* (2013.01); *A61B 5/048* (2013.01); *A61B 5/0006* (2013.01);
(Continued)

(58) Field of Classification Search
CPC .. A61B 5/04014; A61B 5/04017; A61B 5/048
See application file for complete search history.

(56) References Cited

U.S. PATENT DOCUMENTS 2,507,631 A   5/1950 Hartmann
2,957,880 A   10/1960 Rometsch
(Continued)

FOREIGN PATENT DOCUMENTS

EP      0765630 A1    4/1997
JP    2008178546 A    8/2008
(Continued)

OTHER PUBLICATIONS

Adak S (1998) Time-dependent spectral analysis of nonstationary time series. J Amer Statist Assoc 93(444):1488-1501.
(Continued)

*Primary Examiner* — Eric D. Bertram
(74) *Attorney, Agent, or Firm* — Quarles & Brady LLP

(57) ABSTRACT

Systems and methods for analyzing electrophysiological signals acquired from a subject are provided. In some aspects, a method includes receiving electrophysiological signals acquired from a subject using one or more sensors, and assembling a set of time-series data using the acquired electrophysiological signals. The method also includes analyzing the set of time-series data using a state-space multitaper framework to generate spectral information describing the electrophysiological signals, and determining a brain state of the subject using the spectral information. The method further includes generating a report indicative of the determined brain state.

20 Claims, 25 Drawing Sheets

(51) Int. Cl.
*A61B 5/00* (2006.01)
*A61B 5/0402* (2006.01)
*A61B 5/0482* (2006.01)
*A61B 5/0488* (2006.01)
*A61B 5/0496* (2006.01)
*A61B 5/053* (2006.01)

(52) U.S. Cl.
CPC .......... *A61B 5/0402* (2013.01); *A61B 5/0482* (2013.01); *A61B 5/0488* (2013.01); *A61B 5/0496* (2013.01); *A61B 5/0533* (2013.01); *A61B 5/4812* (2013.01); *A61B 5/4821* (2013.01); *A61B 5/725* (2013.01); *A61B 5/7257* (2013.01)

(56) References Cited

U.S. PATENT DOCUMENTS

| | | | |
|---|---|---|---|
| 4,195,643 | A | 4/1980 | Pratt, Jr. |
| 4,392,849 | A | 7/1983 | Petre et al. |
| 4,448,199 | A | 5/1984 | Schmid |
| 4,911,167 | A | 3/1990 | Corenman et al. |
| 5,195,530 | A | 3/1993 | Shindel |
| 5,851,438 | A | 12/1998 | Chan |
| 5,908,850 | A | 6/1999 | Zeitlin et al. |
| 6,025,362 | A | 2/2000 | Fukunaga et al. |
| 6,032,063 | A | 2/2000 | Hoar et al. |
| 6,032,065 | A | 2/2000 | Brown |
| 6,067,467 | A | 5/2000 | John |
| 6,281,242 | B1 | 8/2001 | Regan et al. |
| 6,338,713 | B1 | 1/2002 | Chamoun et al. |
| 6,708,051 | B1 | 3/2004 | Durousseau |
| 6,740,214 | B1 | 5/2004 | Dobson et al. |
| 6,944,565 | B2 | 9/2005 | Mcneilage et al. |
| 7,006,872 | B2 | 2/2006 | Gielen et al. |
| 7,286,871 | B2 | 10/2007 | Cohen |
| 7,783,343 | B2 | 8/2010 | Sarkela et al. |
| 8,025,404 | B2 | 9/2011 | Bolger et al. |
| 8,073,534 | B2 | 12/2011 | Low |
| 8,244,526 | B2 | 8/2012 | Vos et al. |
| 8,298,154 | B2 | 10/2012 | Hete et al. |
| 8,315,970 | B2 | 11/2012 | Zalay et al. |
| 8,521,294 | B2 | 8/2013 | Sarma et al. |
| 8,630,722 | B2 | 1/2014 | Condurso et al. |
| 10,299,720 | B2 | 5/2019 | Brown |
| 2002/0128798 | A1 | 9/2002 | Lange et al. |
| 2002/0156357 | A1 | 10/2002 | Axelgaard |
| 2003/0088167 | A1 | 5/2003 | Fendrock et al. |
| 2003/0130585 | A1 | 7/2003 | Wenger |
| 2004/0143021 | A1 | 7/2004 | Larijani |
| 2004/0193068 | A1 | 9/2004 | Burton et al. |
| 2005/0054941 | A1 | 3/2005 | Ting et al. |
| 2006/0135880 | A1 | 6/2006 | Sarkela |
| 2006/0178585 | A1 | 8/2006 | Sharrock |
| 2006/0229519 | A1 | 10/2006 | Fujiwara et al. |
| 2007/0067003 | A1 | 3/2007 | Sanchez et al. |
| 2007/0073355 | A1 | 3/2007 | Dilorenzo |
| 2007/0100389 | A1 | 5/2007 | Jaax et al. |
| 2007/0123468 | A1 | 5/2007 | Jenkins |
| 2007/0150025 | A1 | 6/2007 | Dilorenzo et al. |
| 2007/0167694 | A1 | 7/2007 | Causevic et al. |
| 2007/0191704 | A1 | 8/2007 | DeCharms |
| 2007/0203540 | A1 | 8/2007 | Goetz et al. |
| 2008/0021345 | A1 | 1/2008 | Kern et al. |
| 2008/0249431 | A1 | 10/2008 | Bier et al. |
| 2008/0306397 | A1 | 12/2008 | Bonmassar et al. |
| 2010/0023089 | A1 | 1/2010 | DiLorenzo |
| 2010/0280333 | A1 | 11/2010 | Parshuram et al. |
| 2011/0044524 | A1 | 2/2011 | Wang et al. |
| 2011/0082381 | A1 | 4/2011 | Uthman et al. |
| 2011/0125046 | A1 | 5/2011 | Burton et al. |
| 2011/0137134 | A1 | 6/2011 | Hemmerling et al. |
| 2011/0137297 | A1 | 6/2011 | Kiani et al. |
| 2011/0218454 | A1 | 9/2011 | Low |
| 2011/0224570 | A1 | 9/2011 | Causevic |
| 2012/0022391 | A1 | 1/2012 | Leuthardt |
| 2012/0029378 | A1 | 2/2012 | Low |
| 2012/0101401 | A1 | 4/2012 | Faul et al. |
| 2012/0250963 | A1 | 10/2012 | Carroll et al. |
| 2013/0131464 | A1 | 5/2013 | Westbrook et al. |
| 2013/0197339 | A1 | 8/2013 | Bardakjian et al. |
| 2013/0211224 | A1 | 8/2013 | Isenhart et al. |
| 2013/0310422 | A1 | 11/2013 | Brown et al. |
| 2013/0331660 | A1 | 12/2013 | Al-Ali et al. |
| 2014/0012100 | A1 | 1/2014 | Al-Ali et al. |
| 2014/0180160 | A1* | 6/2014 | Brown ............... A61B 5/4821 600/544 |
| 2014/0187973 | A1 | 7/2014 | Brown et al. |
| 2014/0316217 | A1 | 10/2014 | Purdon et al. |
| 2014/0316218 | A1 | 10/2014 | Purdon et al. |
| 2014/0323897 | A1 | 10/2014 | Brown et al. |
| 2014/0323898 | A1 | 10/2014 | Purdon et al. |
| 2014/0371548 | A1 | 12/2014 | Al-Ali et al. |
| 2015/0011907 | A1 | 1/2015 | Purdon et al. |
| 2015/0080754 | A1 | 3/2015 | Purdon et al. |
| 2016/0007910 | A1* | 1/2016 | Boss ............... A61B 5/02055 600/301 |
| 2019/0290196 | A1 | 9/2019 | Brown |

FOREIGN PATENT DOCUMENTS

| | | |
|---|---|---|
| RU | 95243 U1 | 6/2010 |
| WO | 2004036379 A2 | 4/2004 |
| WO | 2004037114 A2 | 5/2004 |
| WO | 2004047632 A1 | 6/2004 |
| WO | 2012145285 A1 | 10/2012 |
| WO | 2012154701 A1 | 11/2012 |

OTHER PUBLICATIONS

Ba D, et al. (2014) Robust spectrotemporal decomposition by iteratively reweighted least squares. Proc Natl Acad Sci USA 111(50):E5336-E5345.

Babadi B et al (2014) A review of multitaper spectral analysis. IEEE Trans Biomed Eng 61(5):1555-1564.

Bohlin T (1977) Analysis of EEG signals with changing spectra a short-word Kalman estimator. Math Biosci 35(3-4):221-259.

Chemali, Jessica, et al. "Burst suppression probability algorithms: state-space methods for tracking EEG burst suppression." Journal of neural engineering 10.5 (2013): 056017.

Czanner G, et al (2008) Analysis of between-trial and within-trial neural spiking dynamics. J Neurophysiol 99(5):2672-2693.

Dahlhaus R (1997) Fitting time series models to nonstationary processes. Annal Stat 25(1):1-37.

Dahlhaus RD (2000) A likelihood approximation for locally stationary processes. Annal Stat 28(6):1762-1794.

Daubechies I, et al (2011) Synchrosqueezed wavelet transforms: An empirical mode decomposition-like tool. Appl Comput Harmon Anal 30(2):243-261.

Huang NE, et al. (1998) The empirical mode decomposition and the Hilbert spectrum for nonlinear and non-stationary time series analysis. Proc R Soc Lond A 454(1971):903-995.

International Searching Authority, International Search Report and Written Opinion for application PCT/US2017/063690, dated Feb. 13, 2018, 7 pages.

Jiru, A. "Relationships between spectral peak frequencies of a causal AR (P) process and arguments of roots of the associated ar polynomial." San Jose State University (2008).

Prerau MJ, et al (2017) Sleep neurophysiological dynamics through the lens of multitaper spectral analysis. Physiology 32(1):60-92.

Purdon PL, et al (2015) Clinical electroencephalography for anesthesiologists Part I: background and basic signatures. Anesthesiology 123(4):937-960.

Qi Y, et al (2002) Bayesian spectrum estimation of unevenly sampled nonstationary data. Proc IEEE Int Conf Acoust Speech Signal Process vol. 2, pp. 1473-1476.

Smith AC, et al (2003) Estimating a state-space model from point process observations. Neural Comput 15(5):965-991.

(56) References Cited

OTHER PUBLICATIONS

Tarvainen MP, et al (2004) Estimation of nonstationary EEG with Kalman smoother approach: An application to event-related synchronization (ERS). IEEE Trans Biomed Eng 51(3):516-524.
Absalom, et al., Closed Loop Anesthesia: Are We Getting Close to Finding the Holy Grail?, Anesthesia & Analgesia, 2011, 112(3):516-518.
Absalom, et al., Closed-Loop Control of Anesthesia Using Bispectral Index, Anesthesiology, 2002, 96(1):67-73.
Andrews, et al., The Chronux Manual, Aug. 16, 2008, 178 pages.
Araki, et al., Computer Control of Physiological States of Patients Under and After Surgical Operation, Annual Reviews in Control, 2005, 29:229-236.
Article: "Polyesters", http://web.archive.org/web/20020812093256/http://pslc.ws/macrog/pet.htm, Copyright 1995, 1996 Department of Polymer Science, University of Southern Mississippi, 4 pages.
Barras, et al., Total Intravenous Anesthesia on the Battlefield, The Army Medical Department Journal, 2009, pp. 68-72.
Bellville, et al., Servo Control of General Anesthesia, Science, 1957, 126:827-830.
Besch, et al., Occurrence of and Risk Factors for Electroencephalogram Burst Suppression During Propofol-Remifentanil Anaesthesia, British Journal of Anaesthesia, Advance Access Published Aug. 8, 2011, 8 pages.
Besthorn, et al., EEG Coherence in Alzheimer Disease, Electroencephalography and Clinical Neurophysiology, 1994, 90:242-245.
Bickford, Automatic Electroencephalographic Control of General Anesthesia, EEG Clin. Neurophysiol., 1950, 2:93-96.
Bickford, Use of Frequency Discrimination in the Automatic Electroencephalographic Control of Anesthesia (Servo-Anesthesia), EEG Clin. Neurophysiol., 1951, 3:83-86.
Blanco, et al., Time-Frequency Analysis of Electroencephalogram Series. III. Wavelet Packets and Information Cost Function, Physical Review E, 1998, 57(1):932-940.
Bonmassar, Resistive Tapered Stripline (RTS) in Electroencephalogram Recordings During MRI, IEEE Transactions on Microwave Theory and Techniques, 2004, 52(8):1992-1998.
Bourguignon, et al., A Sparsity-Based Method for the Estimation of Spectral Lines From Irregularly Sampled Data, IEEE Journal of Selected Topics in Signal Processing, 2007, 1(4):575-585.
Breshears, et al., Stable and Dynamic Cortical Electrophysiology of Induction and Emergence with Propofol Anesthesia, PNAS, 2010, 107(49):21170-21175.
Candes, et al., Enhancing Sparsity by Reweighted l1 Minimization, J. Fourier Anal. Appl., 2008, 14:877-905.
Ching, et al., A Neurophysiological-Metabolic Model for Burst Suppression, PNAS, 2012, 109(8):3095-3100.
Cimenser, et al., Tracking Brain States Under General Anesthesia by Using Global Coherence Analysis, PNAS, 2011, 108(21):8832-8837.
Ciuciu, et al., A Half-Quadratic Block-Coordinate Descent Method for Spectral Estimation, Signal Processing, 2002, 82:941-959.
Cotten, et al., Closed-Loop Continuous Infusions of Etomidate and Etomidate Analogs in Rats, Anesthesiology, 2011, 115(4):764-773.
Dodson, et al., Postoperative Effects of Methylphenidate, British Journal of Anaesthesia, 1980, 52:1265-1270.
European Patent Office, Extended European Search Report, Application No. 12781958.9, dated Sep. 15, 2014, 12 pages.
Gentilini, et al., Modeling and Closed-Loop Control of Hypnosis by Means of Bispectral Index (BIS) with Isoflurane, IEEE Transactions on Biomedical Engineering, 2001, 48(8):874-889.
Glass, Automated Control of Anesthesia Ten Years Later: Futuristic Novelty or Present Day Reality, Can. J. Anesth./ J. Can. Anesth., 2010, 57:715-719.
Goldman, et al., Acquiring Simultaneous EEG and Functional MRI, Clinical Neurophysiology, 2000, 111:1974-1980.
Hahn, et al., A Direct Dynamic Dose-Response Model of Propofol for Individualized Anesthesia Care, Journal of Latex Class Files, 2007, 6(1):1-8.
Hahn, et al., Closed-Loop Anesthetic Drug Concentration Estimation Using Clinical-Effect Feedback, IEEE Transactions on Biomedical Engineering, 2011, 58(1):3-6.
Hemmerling, et al., A Randomized Controlled Trial Demonstrates that a Novel Closed-Loop Propofol System Performs Better Hypnosis Control than Manual Administration, Can. J. Anesth./J. Can. Anesth., 2010, 57:725-735.
John, et al., Invariant Reversible QEEG Effects of Anesthetics, Consciousness and Cognition, 2001, 10:165-183.
Lemieux, et al., Recording of EEG During fMRI Experiments: Patient Safety, MRM, 1997, 38:943-952.
Leslie, et al., Closed Loop Control of Sedation for Colonoscopy Using the Bispectral Index, Anaesthesia, 2002, 57:690-709.
Liley, et al., Propofol and Remifentanil Differentially Modulate Frontal Electroencephalographic Activity, Anesthesiology, 2010, 113:292-304.
Lin, et al., EEG-Based Drowsiness Estimation for Safety Driving Using Independent Component Analysis, IEEE Transactions on Circuits and Systems-I: Regular Papers, 2005, 52(12):2726-2738.
Liu, et al., Feasibility of Closed-Loop Titration of Propofol Guided by the Bispectral Index for General Anaesthesia Induction: A Prospective Randomized Study, European Journal of Anaesthesiology, 2006, 23:465-469.
Liu, et al., Neural Origin of Spontaneous Hemodynamic Fluctuations in Rats Under Burst-Suppression Anesthesia Condition, Cerebral Cortex, 2011, 21:374-384.
Liu, et al., Titration of Propofol for Anesthetic Induction and Maintenance Guided by the Bispectral Index: Closed-Loop Versus Manual Control, Anesthesiology, 2006, 104:686-695.
Locher, et al., A New Closed-Loop Control System for Isoflurane Using Bispectral Index Outperforms Manual Control, Anesthesiology, 2004, 101:591-602.
Lotte, et al., A Review of Classification Algorithms for EEG-Based Brain-Computer Interfaces, Journal of Neural Engineering, 2007, 4:R1-R13.
Martin, et al., Investigating Neural-Hemodynamic Coupling and the Hemodynamic Response Function in the Awake Rat, NeuroImage, 2006, 32:33-48.
Mirsattari, et al., Treatment of Refractory Status Epilepticus With Inhalational Anesthetic Agents Isoflurane and Desflurane, Arch. Neurol., 2004, 61:1254-1259.
Molaee-Ardekani, et al., Delta Waves Differently Modulate High Frequency Components of EEG Oscillations in Various Unconsciousness Levels, Proceedings of the 29th Annual International Conference of the IEEE EMBS, 2007, pp. 1294-1297.
Morley, et al., Closed Loop Control of Anaesthesia: An Assessment of the Bispectral Index as the Target of Control, Anaesthesia, 2000, 55:953-959.
Mortier, et al., Closed-Loop Controlled Administration of Propofol Using Bispectral Analysis, Anesthesia, 1998, 53:749-754.
Orsini, et al., Propofol Infusion Syndrome: Case Report and Literature Review, Am. J. Health-Syst. Pharm., 2009, 66:908-915.
PCT International Search Report and Written Opinion, PCT/US2005/042401, dated Jun. 14, 2006, 17 pages.
PCT International Search Report and Written Opinion, PCT/US2009/062072, dated May 12, 2010, 13 pages.
PCT International Search Report and Written Opinion, PCT/US2011/050213, dated May 1, 2012, 12 pages.
PCT International Search Report and Written Opinion, PCT/US2012/036854, dated Aug. 16, 2012, 6 pages.
PCT International Search Report and Written Opinion, PCT/US2013/064852, dated Jan. 23, 2014, 6 pages.
PCT International Search Report and Written Opinion, PCT/US2014/033619, dated Sep. 23, 2014, 12 pages.
PCT International Search Report and Written Opinion, PCT/US2014/035166, dated Aug. 29, 2014, 17 pages.
PCT International Search Report and Written Opinion, PCT/US2014/035178, dated Sep. 15, 2014, 15 pages.
PCT International Search Report and Written Opinion, PCT/US2014/035319, dated Sep. 26, 2014, 15 pages.
PCT International Search Report and Written Opinion, PCT/US2014/035329, dated Sep. 26, 2014, 11 pages.

(56) References Cited

OTHER PUBLICATIONS

PCT International Search Report and Written Opinion, PCT/US2014/035333, dated Sep. 26, 2014, 14 pages.
PCT International Search Report and Written Opinion, PCT/US2014/044692, dated Nov. 4, 2014, 12 pages.
PCT International Search Report and Written Opinion, PCT/US2014/044720, dated Nov. 28, 2014, 13 pages.
PCT International Search Report and Written Opinion, PCT/US2014/055509, dated Dec. 2, 2014, 15 pages.
PCT International Search Report and Written Opinion, PCT/US2014/064144, dated Jan. 27, 2015, 7 pages.
Pritchett, et al., Power Analysis of Gamma Frequencies (30-47Hz), Adjusting for Muscle Activity (80-97Hz), in Anesthesia: A Comparison Between Young Adults, Middle-Aged and the Elderly, 30th Annual International IEEE EMBS Conference, 2008, pp. 825-830.
Purdon, et al., Electroencephalogram Signatures of Loss and Recovery of Consciousness from Propofol, PNAS, Published Online Mar. 4, 2013, pp. E1142-E1151.
Purdon, Multimodal Neuroimaging with Simultaneous Electroencephalogram and High-Field Functional Magnetic Resonance Imaging, Master Thesis Submitted to the Harvard-MIT Division of Health Sciences and Technology, Jun. 2005.
Puri, et al., Closed-Loop Anaesthesia Delivery System (CLADS(TM)) Using Bispectral Index: A Performance Assessment Study, Anaesthesia and Intensive Care, 2007, 35(3):357-362.
Roche-LaBarbe, et al., Coupled Oxygenation Oscillation Measured by NIRS and Intermittent Cerebral Activation on EEG in Premature Infants, NeuroImage, 2007, 36:718-727.
Rossetti, et al., Refractory Status Epilepticus, Effect of Treatment Aggressiveness on Prognosis, Arch. Neurol., 2005, 62:1698-1702.
Sacchi, et al., Interpolation and Extrapolation Using a High-Resolution Discrete Fourier Transform, IEEE Transactions on Signal Processing, 1998, 46(1):31-38.
Sartori, et al., On-Line Estimation of Propofol Pharmacodynamic Parameters, Proceedings of the 2005 IEEE Engineering in Medicine and Biology 27th Annual Conference, 2005, pp. 74-77.
Sawaguchi, et al., A Model-Predictive Hypnosis Control System Under Total Intravenous Anesthesia, IEEE Transactions on Biomedical Engineering, 2008, 55(3):874-887.
Schaffer, et al., The Effect of the Atmosphere and the Role of Pore Filling on the Sintering of Aluminum, Acta Materialia, 2006, 54(1):131-138.
Schwilden, et al., Closed-Loop Feedback Control of Methohexital Anesthesia by Quantitative EEG Analysis in Humans, Anesthesiology, 1987, 67:341-347.
Schwilden, et al., Closed-Loop Feedback Control of Propofol Anaesthesia by Quantitative EEG Analysis in Humans, Br. J. Anaesth., 1989, 62:290-296.
Struys, et al., Closed Loops in Anaesthesia, Best Practice & Research Clinical Anaesthesiology, 2006, 20 (1):211-220.
Struys, et al., Comparison of Closed-Loop Controlled Administration of Propofol Using Bispectral Index as the Controlled Variable Versus "Standard Practice" Controlled Administration, Anesthesiology, 2001, 95(1):6-17.
Tan, et al., Sparse Learning Via Iterative Minimization With Application to MIMO Radar Imaging, IEEE Transactions on Signal Processing, 2011, 59(3)1088-1101.
Truccolo, et al., A Point Process Framework for Relating Neural Spiking Activity to Spiking History, Neural Ensemble, and Extrinsic Covariate Effects, J. Neurophysiol., 2005, 93:1074-1089.
Van Vugt, Comparison of Spectral Analysis Methods for Characterizing Brain Oscillations, J. Neurosci. Methods, 2007, 162(1-2):49-63.
Vijn, et al., I.v. Anaesthesia and EEG Burst Suppression in Rats: Bolus Injections and Closed-Loop Infusions, British Journal of Anaesthesia, 1998, 81:415-421.
Vusanovic, et al., Microsegregation Phenomena in Al—Cu—Mg Alloy with Considering of Diffusion Phenomena in Primary Phase, Facta Universitatis, Series: Mechanical Engineering, 2001, 1(8):965-980.
Wang, et al., Precipitates and Intermetallic Phases in Precipitation and Hardening Al—Cu—Mg—(Li) Based Alloys, International Materials Reviews, 2005, 50(4):193-215.
Zdunek, et al., Improved M-FOCUSS Algorithm With Overlapping Blocks for Locally Smooth Sparse Signals, IEEE Transactions on Signal Processing, 2008, 56(10):4752-4761.

* cited by examiner

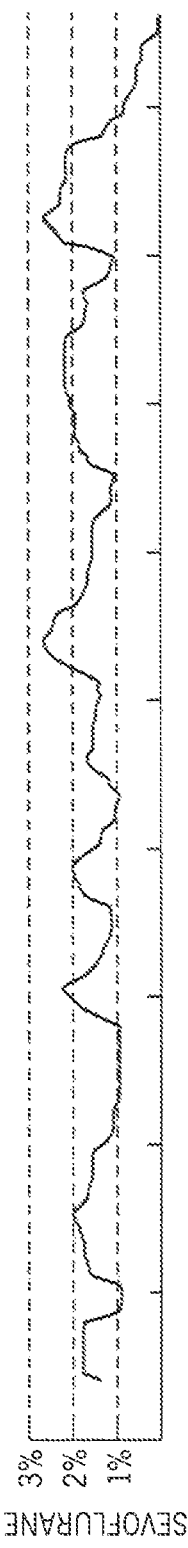
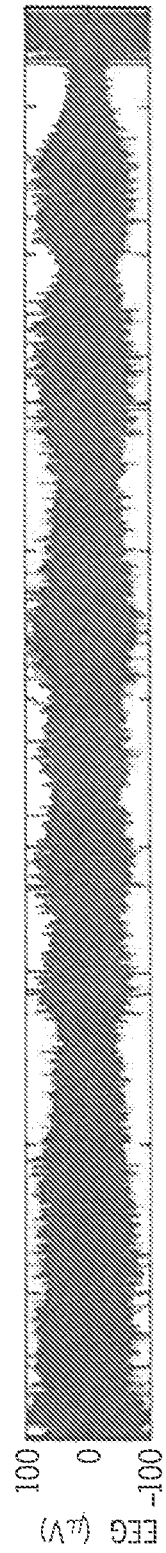
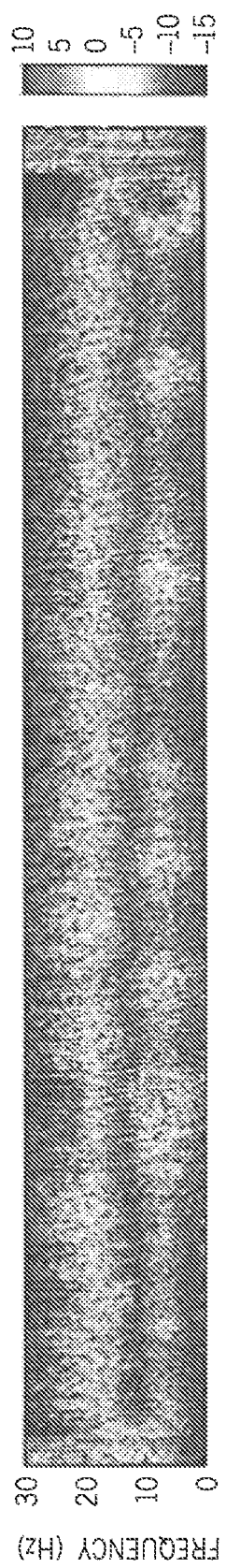
FIG. 5A
FIG. 5B
FIG. 5C

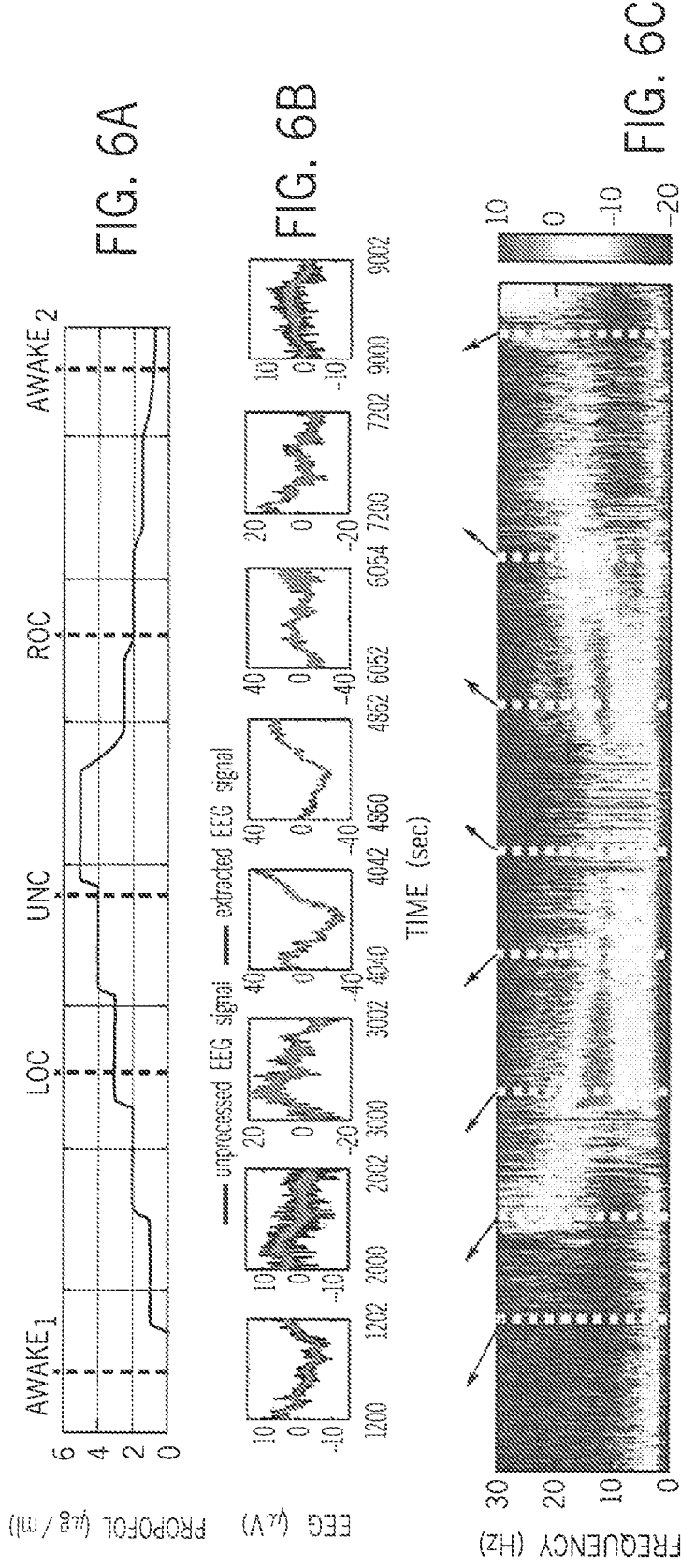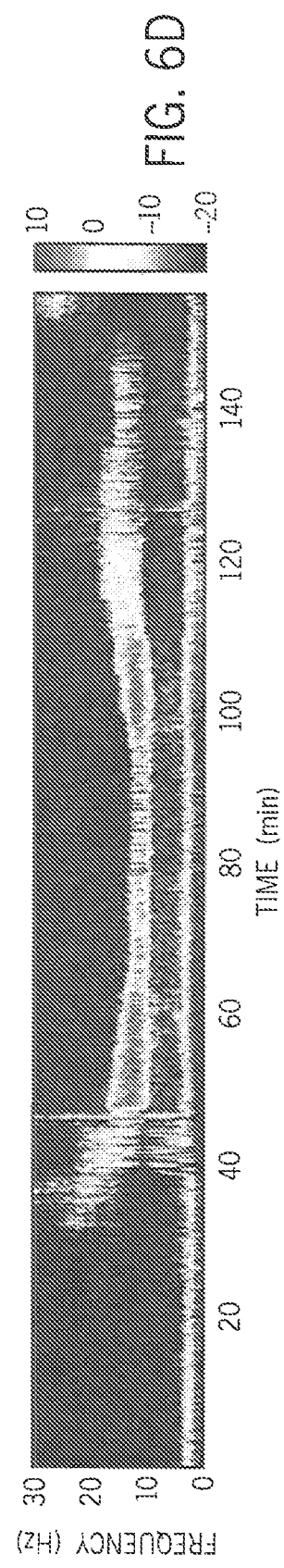

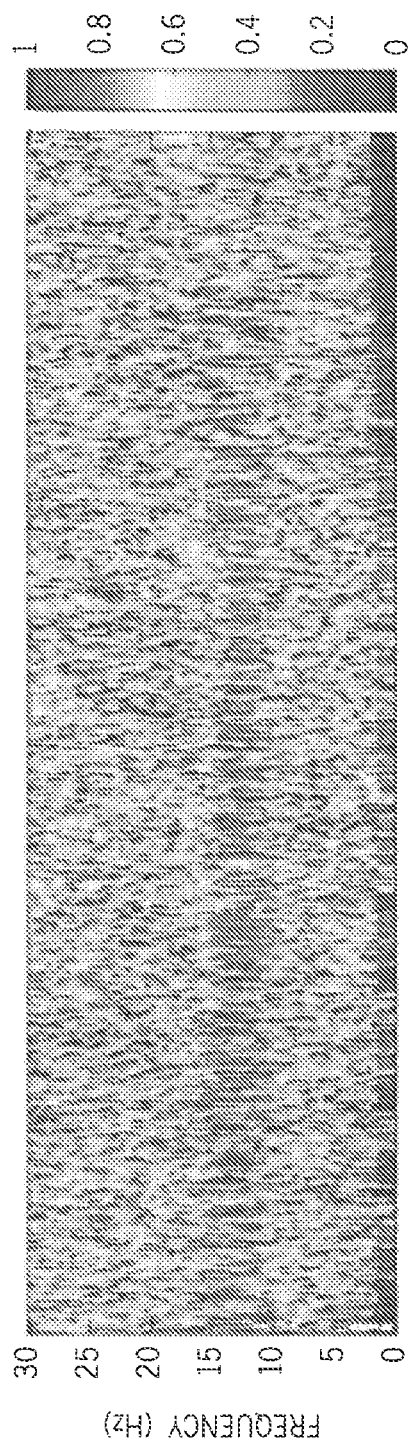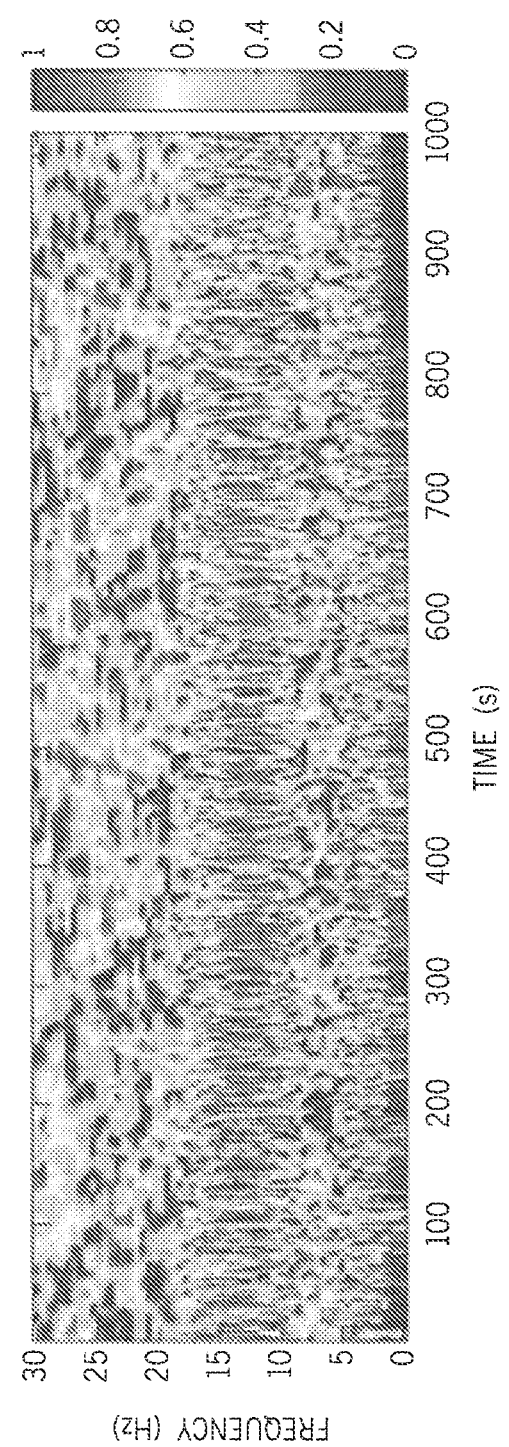

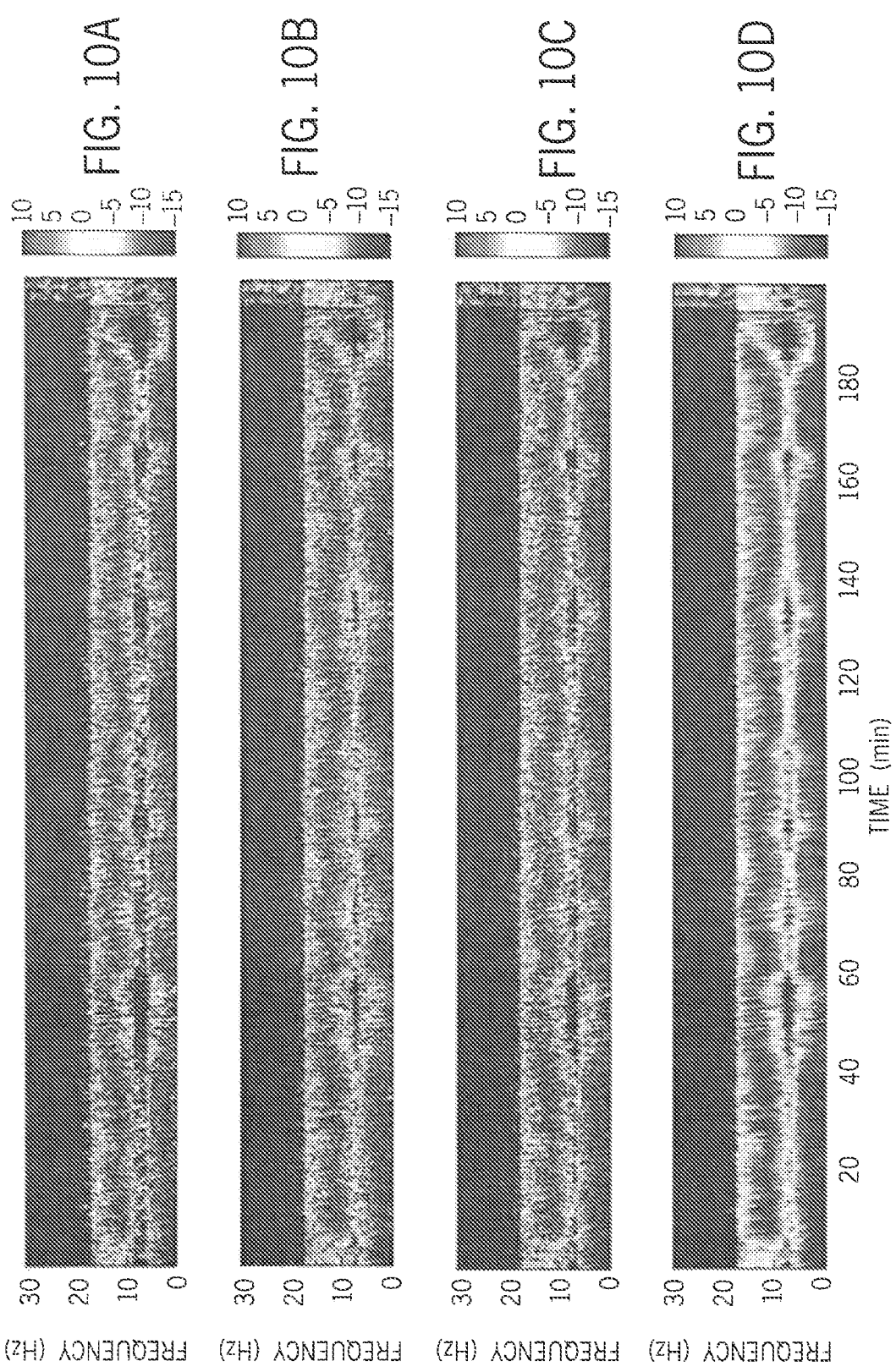

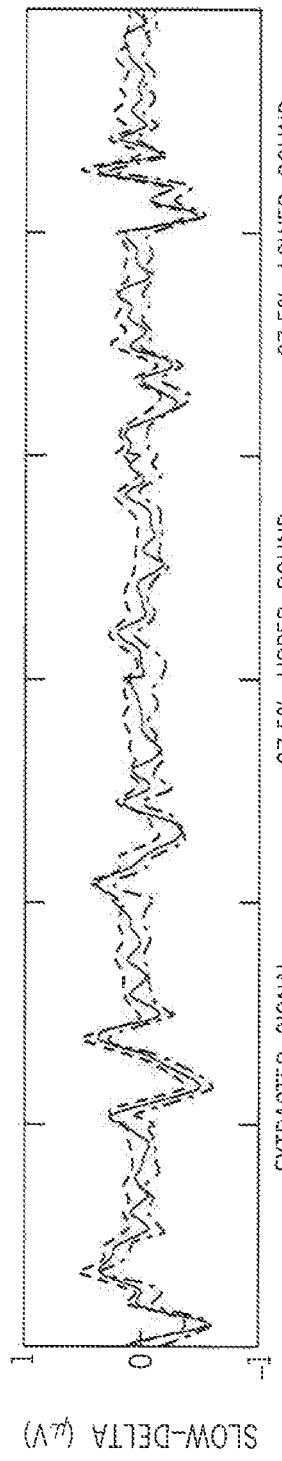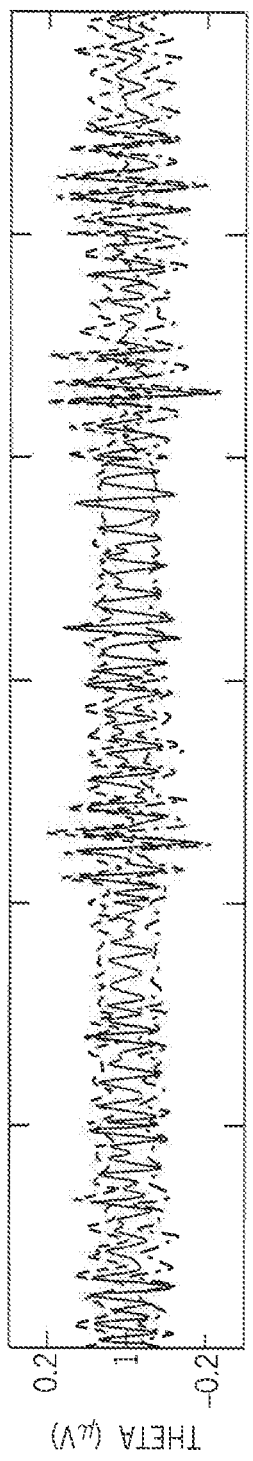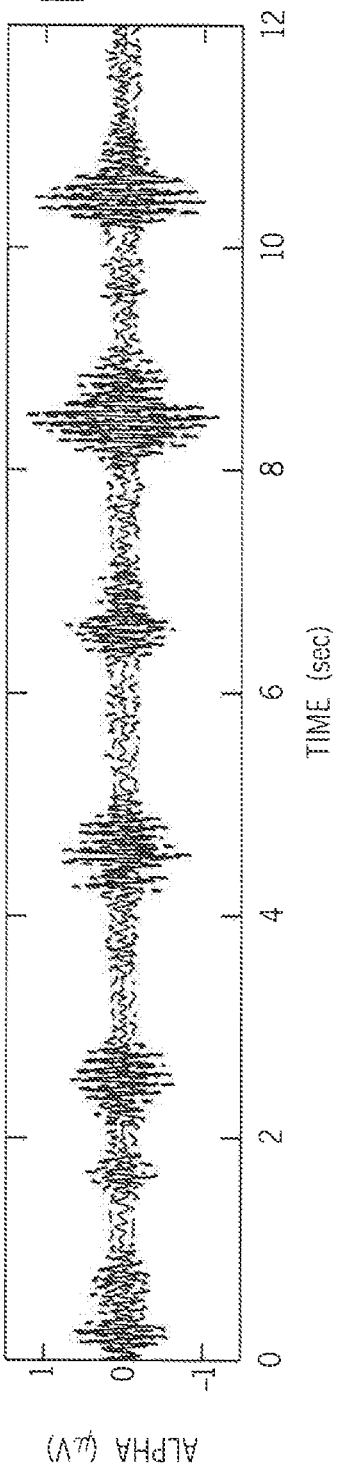

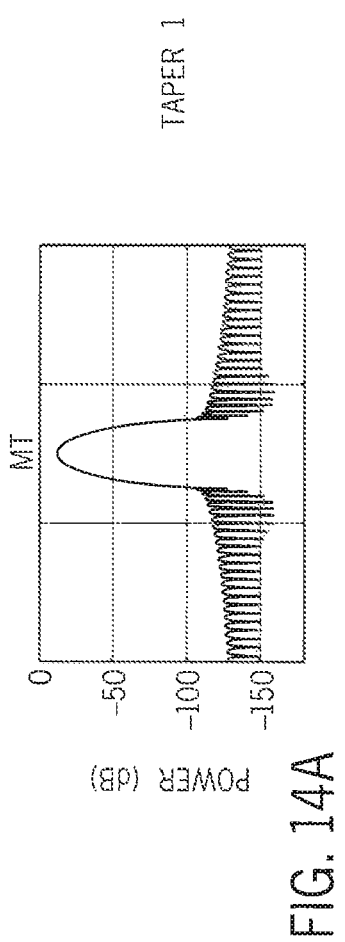
FIG. 14A / FIG. 14B — TAPER 1
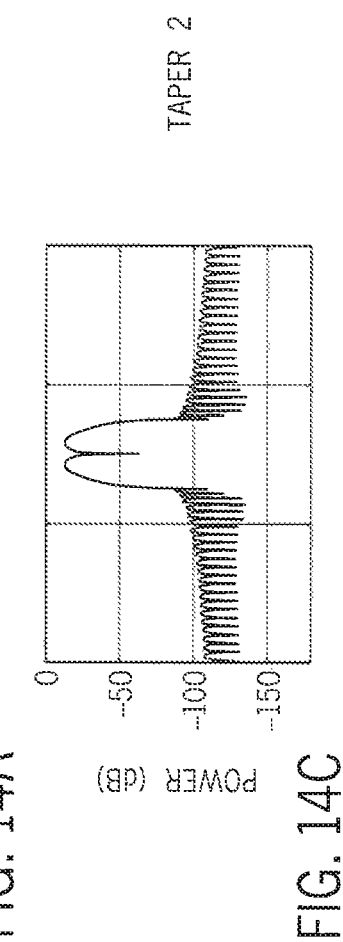
FIG. 14C / FIG. 14D — TAPER 2
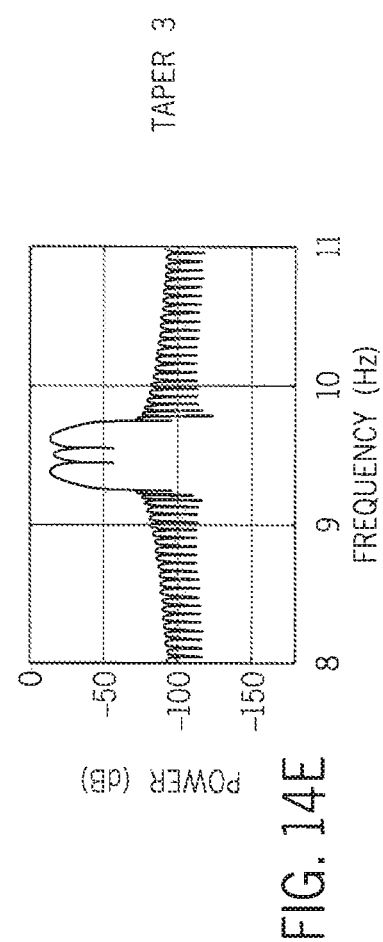
FIG. 14E / FIG. 14F — TAPER 3

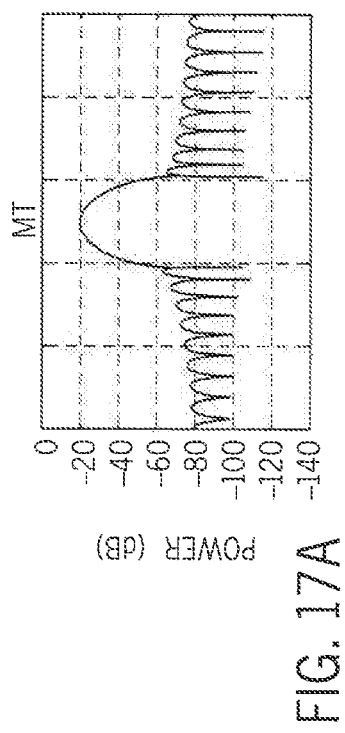
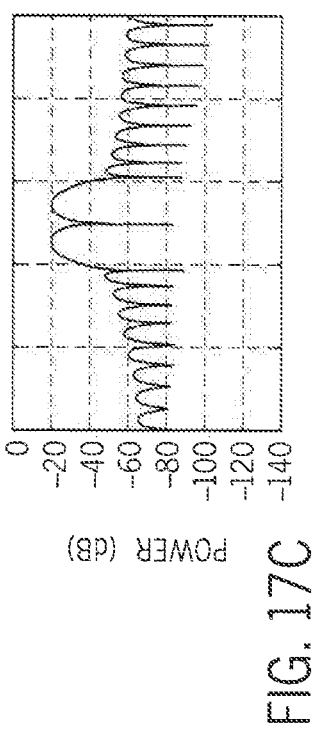
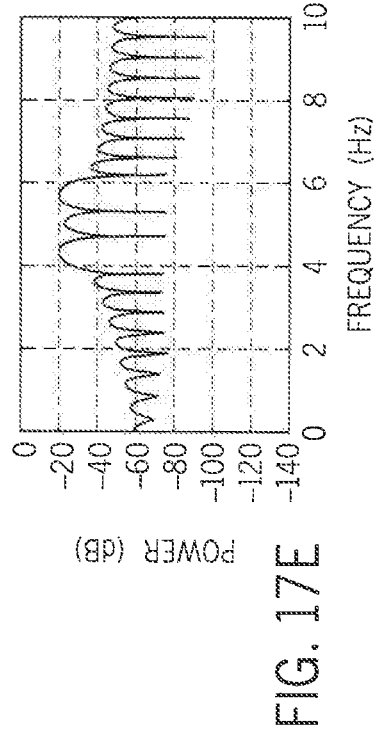
FIG. 17A  FIG. 17B
FIG. 17C  FIG. 17D
FIG. 17E  FIG. 17F

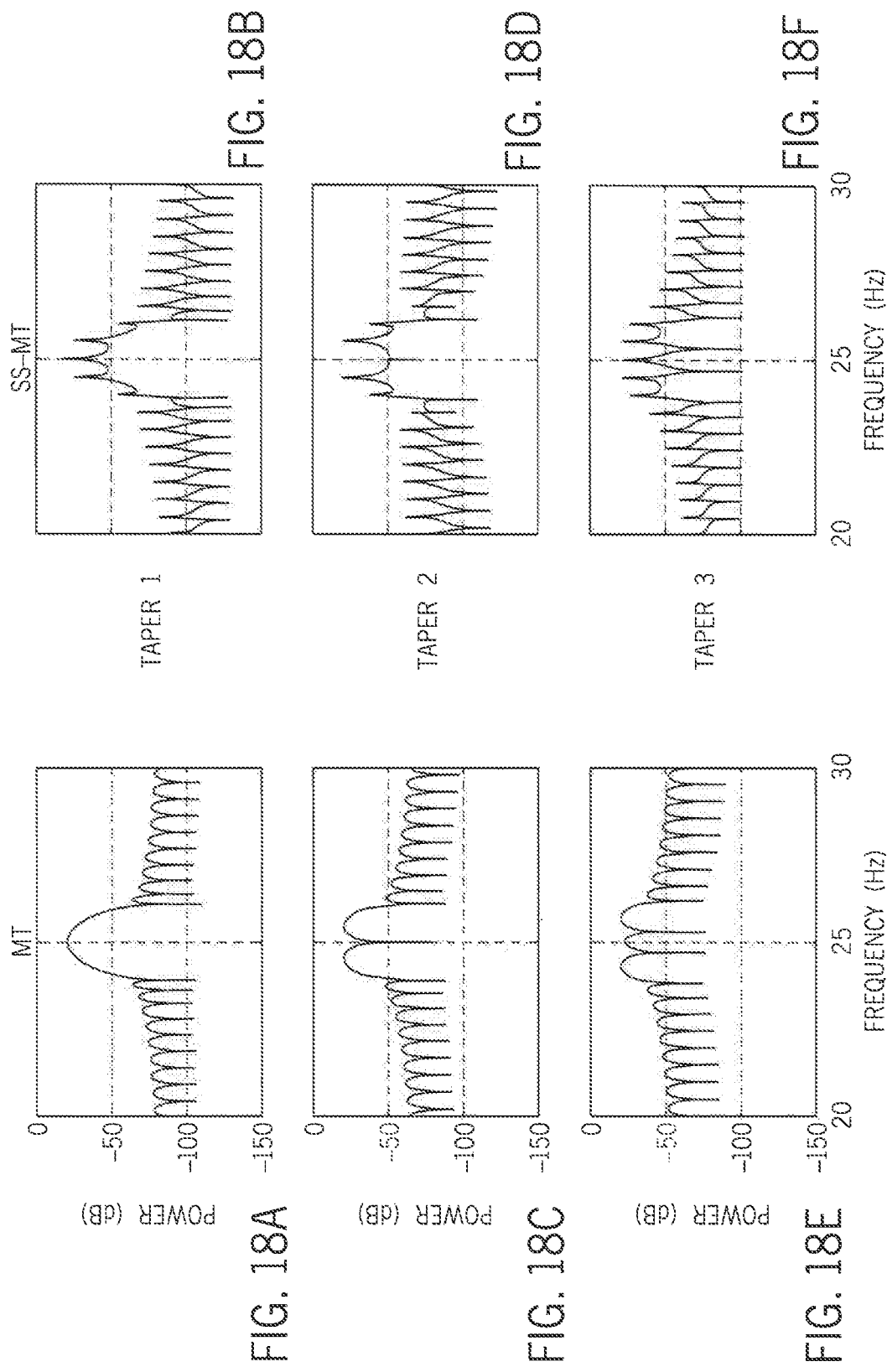

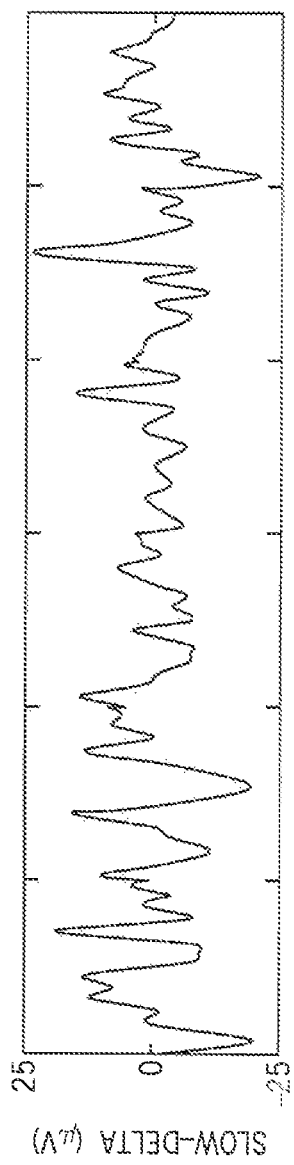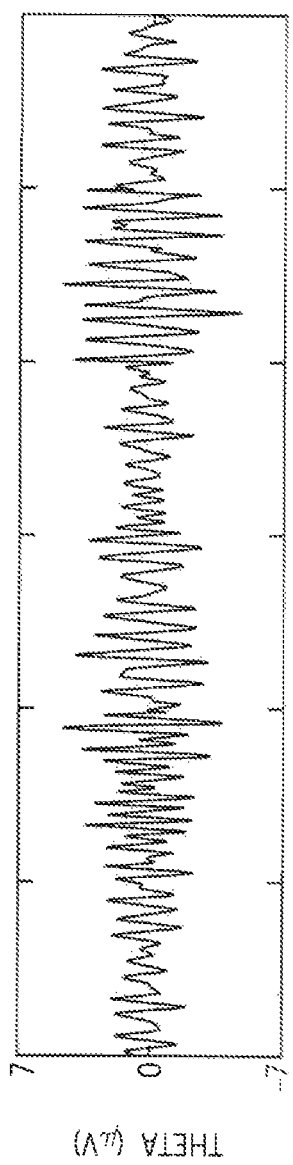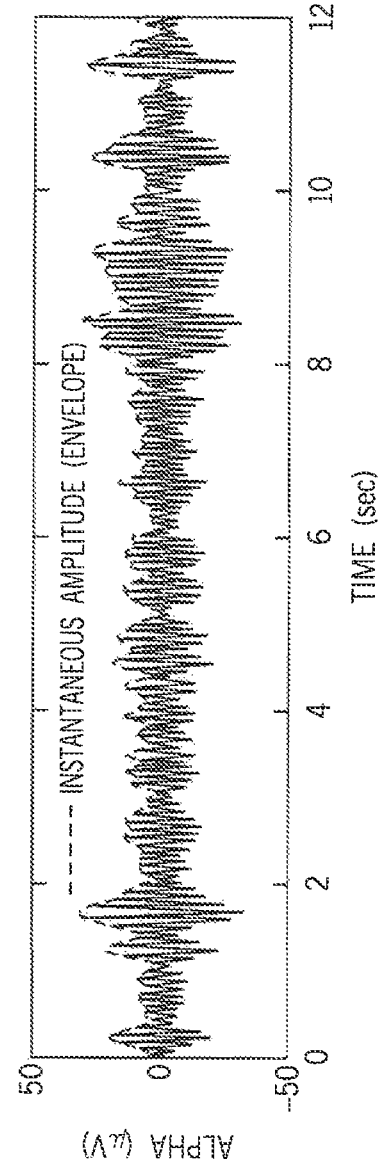

SYSTEMS AND METHODS FOR ANALYZING ELECTROPHYSIOLOGICAL DATA FROM PATIENTS UNDERGOING MEDICAL TREATMENTS

CROSS-REFERENCE TO RELATED APPLICATIONS

This application is based on, claims priority to, and incorporates herein by reference in its entirety for all purposes U.S. Application Ser. No. 62/427,524, filed Nov. 29, 2016.

STATEMENT REGARDING FEDERALLY SPONSORED RESEARCH

This invention was made with government support under R01-GM104948 awarded by the National Institutes of Health. The government has certain rights in the invention.

BACKGROUND

The present disclosure generally relates to systems and methods for processing data. More particularly, the present disclosure is directed to systems and methods for analyzing electrophysiological data from patients undergoing medical treatments.

Across nearly all fields of science and engineering, non-stationary behavior in time-series data, generated from various evolving temporal and/or spatial dynamics, is a ubiquitous phenomenon. Common examples include speech, image and video signals, brain activity measurements, seismic and oceanographic recordings, and radar emissions, and others. Given that the temporal and spatial dynamics in time-series data are often complex, non-parametric spectral techniques are typically used in data analysis. For example, Fourier methods combined with tapering techniques or wavelets are commonly used to analyze the spectral properties of the time-series data.

Many technologies have been developed to help clinicians diagnose and treat patients in clinical and home settings. These include monitoring systems that acquire and analyze electrophysiological signals during sleep, task activities, general anesthesia, sedation, coma, and other medical conditions or treatments. Specifically, EEG-based systems have been used in the operating room and intensive care unit to track neural activity of patients. Using proprietary algorithms, such systems combine different information derived by processing EEG data, and other electrophysiological data, and produce various partial or amalgamized representations or indices that indicate the level of consciousness of a patient. These are then used by clinicians to identify and then manage the state of the patient, often using pharmacological or other methods. In some "closed-loop" systems, feedback generated based on processed data is also used to activate or control treatment devices, such as drug infusion pumps, and so on. Whether a patient is controlled using an automated system or via more traditional clinician-specific control, the results are necessarily limited by the resolution and accuracy of the underlying information that is gathered.

The traditional approach to clinical interpretation of EEG data has been to visually examine time-domain waveforms, and associate different waveform morphologies with physiology, pathophysiology, or clinical outcomes. However, visual time-series analysis is a highly subjective and time-consuming process. For example, during sleep, EEG, electroculogram ("EOG"), electromyography ("EMG"), and respiration signals may be monitored, and then evaluated through visual analysis to diagnose sleep and respiratory disorders. These data records, lasting up to 10 hours in duration, are broken into 30-second segments, each of which must be visually interpreted. This makes it extremely difficult to effectively track non-stationary properties of the sleep signal over time, which may provide important information for characterizing clinically-relevant features of a patient's sleep. In addition, valuable information, including spectral information, is difficult to observe in the time-domain. In another example, general anesthetic and sedative drugs induce stereotyped non-stationary oscillations in the EEG that are much easier to interpret when analyzed in the time-frequency domain using spectral analysis. Therefore, spectral analysis has been an important tool for analyzing EEG, and other data.

In order to identify specific signatures of underlying neural activity present in acquired EEG data, it has been an emerging practice to compute time-frequency representations, often in the form of spectrograms. Techniques utilized include Fast Fourier Transforms ("FFT"), wavelet transforms, Gabor transforms, chirplet transforms, Hanning window, multitaper, and others. Such time-varying spectra, or spectrograms, can then be used to identify and track a patient's brain state, in order to determine proper drug dosage or administration, or identify a likelihood of arousal during a surgical procedure, for example.

In general, spectral techniques often analyze a selected "window" or time interval of a time-series of data in which signals are assumed to be stationary. The window is translated in time to take into consideration the non-stationary nature of the data. Spectral information is generated from each window of data, and used to produce spectrograms, which can be used to identify the dynamics of different spectral features describing the data.

Although commonly used, such window-based approaches have several shortcomings. First, the spectral estimates computed for a given window do not consider estimates computed in adjacent windows. Hence the resulting spectral representations may not fully capture the degree of smoothness inherent in the underlying signal, and as such may not accurately describe the temporal properties of the time-series. Second, the uncertainty principle imposes stringent limits on the spectral resolution achievable by Fourier-based methods within a window. Because the spectral resolution is inversely proportional to the window length, sliding window-based spectral analyses are problematic when the signal dynamics occur at a shorter time-scale than the window length. Also, performing analyses within specific windows considers only the local distribution of the time-series, rather than the joint distribution of all of the data. As a consequence, it is difficult to conduct formal statistical comparisons between the spectral properties of different data segments.

A common objective of many analyses conducted in EEG studies, speech processing, and applications of empirical mode decomposition ("EMD"), involves computing time-frequency representations that are smooth (continuous) in time and sparse in frequency and analyzing information obtained therefrom. However, the spectral estimation procedures typically used are not tailored to achieve smoothness in time and sparsity in frequency. In addition, Fourier-based methods do not allow time-domain or frequency-domain signal extraction because they estimate only signal power as a function of frequency. Furthermore, EMD extracts empirically derived harmonic components, or modes, and applies the Hilbert-Huang transform to the modes to compute instantaneous amplitude and phase. The theoretical basis of EMD and its inference framework remain open questions.

Batch analyses are also common in many applications estimating time-frequency information. Typically, these analyses use the entire data of a recorded time-series to provide estimates at different time points, in principle, such approach could enhance both time and frequency resolution. However, because they require entire sets of data, batch analyses are often performed post-acquisition, and only limited real-time applications. Therefore, windows-based spectral estimation methods remain the solution of choice.

In light of the above, there is a need for improved systems and methods for processing non-stationary data to generate accurate spectral information.

SUMMARY

The present disclosure overcomes the drawbacks of previous technologies by providing systems and methods for analyzing electrophysiological data in patients undergoing medical treatments. Specifically, the present disclosure is directed to a novel approach that incorporates a state-space framework with a multi-taper ("MT") technique to provide high-resolution spectral information, herein referred to as state-space multitaper ("SS-MT"). As will become apparent from description herein, this approach takes into account the continuity present in discrete and continuous time-series data while balancing bias-variance trade-off.

In one aspect of the present disclosure, a system for analyzing electrophysiological signals acquired from a subject is provided. The system includes an input configured to receive electrophysiological signals acquired from a subject, and at least one processor, in communication with the input. The at least one processor is configured to assemble a set of time-series data using the electrophysiological signals received by the input, and analyze the set of time-series data using a state-space multi-taper framework to generate spectral information describing the electrophysiological signals. The at least one processor is also configured to determine a brain state of the subject using the spectral information, and generate a report indicative of the brain state determined. The system also includes an output configured to provide the report.

In another aspect of the present disclosure, a method for analyzing electrophysiological signals acquired from a subject is provided. The method includes receiving electrophysiological signals acquired from a subject using one or more sensors, and assembling a set of time-series data using the acquired electrophysiological signals. The method also includes analyzing the set of time-series data using a state-space multi-taper framework to generate spectral information describing the electrophysiological signals, and determining a brain state of the subject using the spectral information. The method further includes generating a report indicative of the determined brain state.

In yet another aspect of the present disclosure, a method for monitoring a brain state of a subject is provided. The method includes acquiring electrophysiological signals acquired from a subject using one or more sensors, and assembling a set of time-series data using the acquired electrophysiological signals. The method also includes analyzing the set of time-series data using a state-space multitaper framework to generate spectral information describing the electrophysiological signals, and determining a brain state of the subject using the spectral information. The method further includes monitoring the brain state of the subject over time repeating steps of acquiring electrophysiological signals, assembling a set of time-series data, analyzing the set of time-series data and determining the brain state.

The foregoing and other aspects and advantages of the invention will appear from the following description. In the description, reference is made to the accompanying drawings that form a part hereof, and in which there is shown by way of illustration a preferred embodiment of the invention. Such embodiment does not necessarily represent the full scope of the invention, however, and reference is made therefore to the claims and herein for interpreting the scope of the invention.

BRIEF DESCRIPTION OF THE DRAWINGS

The present invention will hereafter be described with reference to the accompanying drawings, wherein like reference numerals denote like elements. The patent or application file contains at least one drawing executed in color. Copies of this patent or patent application publication with color drawing(s) will be provided by the Office upon request and payment of the necessary fee.

FIG. 5A shows a spectrogram analysis of EEG time-series recorded from a patient under general anesthesia maintained with sevoflurane and oxygen, illustrating the expired concentration of sevoflurane.

FIG. 5B shows raw EEG signals associated with FIG. 5A.

FIG. 5C shows a periodogram associated with FIGS. 5A and 5.

FIG. 6A shows a spectrogram analysis of EEG recorded in a volunteer subject receiving a computer controlled infusion of propofol, which illustrates time course of propofol target effect site concentrations based on the Schneider model and, wherein the black vertical lines define the anesthetic states determined by the behavioral analysis.

FIG. 6B shows a plurality of windows of two-seconds of unprocessed EEG curves (unrefined dark curves) and of EEG signals extracted from the SS-MT analysis (refined curves) at different target effect site concentrations.

FIG. 6C shows a MT spectrogram associated with FIGS. 6A and 6B.

FIG. 6D is a SS-MT spectrogram. The color scale is in decibels.

FIG. 8A shows MT coherogram a cross-spectrogram analysis of two EEG time-series recorded from a patient under general anesthesia maintained with a propofol infusion.

FIG. 8B relates to FIG. 8A, but shows a SS-MT coherogram.

FIG. 10A shows eigenspectrogram and spectrogram estimates of the state-space multitaper algorithm from EEG data recorded from a patient undergoing sevoflurane-induced general anesthesia (FIG. 5), illustrating an eigenspectrogram for a first tapered signal.

FIG. 10B shows eigenspectrogram and spectrogram estimates of the state-space multitaper algorithm from EEG data recorded from a patient undergoing sevoflurane-induced general anesthesia (FIG. 5), illustrating an eigenspectrogram for a second tapered signal.

FIG. 10C shows eigenspectrogram and spectrogram estimates of the state-space multitaper algorithm from EEG data recorded from a patient undergoing sevoflurane-induced general anesthesia (FIG. 5), illustrating an eigenspectrogram for a third tapered signal.

FIG. 10D shows eigenspectrogram and spectrogram estimates of the state-space multitaper algorithm from EEG data recorded from a patient undergoing sevoflurane-induced general anesthesia (FIG. 5), illustrating an eigenspectrogram for a state-space multitaper spectrogram. The color scale is in decibels.

FIG. 11A shows time-domain signals and their 95% credibility intervals, illustrating the slow-delta (0.1 to 4 Hz) oscillation.

FIG. 11B shows the theta (4 to 8 Hz) oscillation that relates to the data of FIG. 11A.

FIG. 11C shows the alpha (8 to 12 Hz) oscillation that relates to the data of FIGS. 11A and 11B, where the black curve is the extracted signal, the red dashed curve is the upper bound of the 95% credibility interval, and the blue dashed curve is the lower bound of the 95% credibility interval.

FIG. 14A shows the power spectral density ("PSD") of the tapers at 25 minutes and at frequency 9.5 Hz for the MT and the SS-MT spectrograms for the simulated time-series in FIG. 4 for taper 1.

FIG. 14B show the PSD for SS-MT algorithm for taper 1.

FIG. 14C shows show the PSD for MT method for taper 2.

FIG. 14D show the PSD for SS-MT algorithm for taper

FIG. 14E show the PSD for MT method for taper 3.

FIG. 14F show the PSD for SS-MT algorithm for taper 3.

FIG. 17A shows the PSD of the tapers at minute 70 and at frequency 5 Hz for the MT and the SS-MT spectrograms for the EEG time-series in FIG. 5 for taper 1.

FIG. 17B shows the PSD for SS-MT algorithm for taper 1.

FIG. 17C shows show the PSD for MT method for taper 2.

FIG. 17D shows the PSD for SS-MT algorithm for taper 2.

FIG. 17E shows the PSD for MT method for taper 3.

FIG. 17F shows the PSD for SS-MT algorithm for taper 3.

FIG. 18A shows the PSD of the tapers at minute 80 and at frequency 25 Hz for the MT and the SS-MT spectrograms for the EEG time-series in FIG. 5 for taper 1.

FIG. 18B shows the PSD for SS-MT algorithm for taper 1.

FIG. 18C shows show the PSD for MT method for taper 2.

FIG. 18D shows the PSD for SS-MT algorithm for taper 2.

FIG. 18E shows the PSD for MT method for taper 3.

FIG. 18F shows the PSD for SS-MT algorithm for taper 3.

FIG. 19A shows time-domain signals in different frequency bands extracted from the 12 sec period beginning at 140 minutes for the EEG time-series in FIG. 5B, illustrating the slow-delta (0.1 to 4 Hz) oscillation.

FIG. 19B shows time-domain signals in different frequency bands extracted from the 12 sec period beginning at 140 minutes for the EEG time-series in FIG. 5B, the theta (4 to 8 Hz) oscillation.

FIG. 19C shows time-domain signals in different frequency bands extracted from the 12 sec period beginning at 140 minutes for the EEG time-series in FIG. 5B, the alpha (8 to 12 Hz) oscillation. The red curve is the instantaneous amplitude.

DETAILED DESCRIPTION

Figure 1:
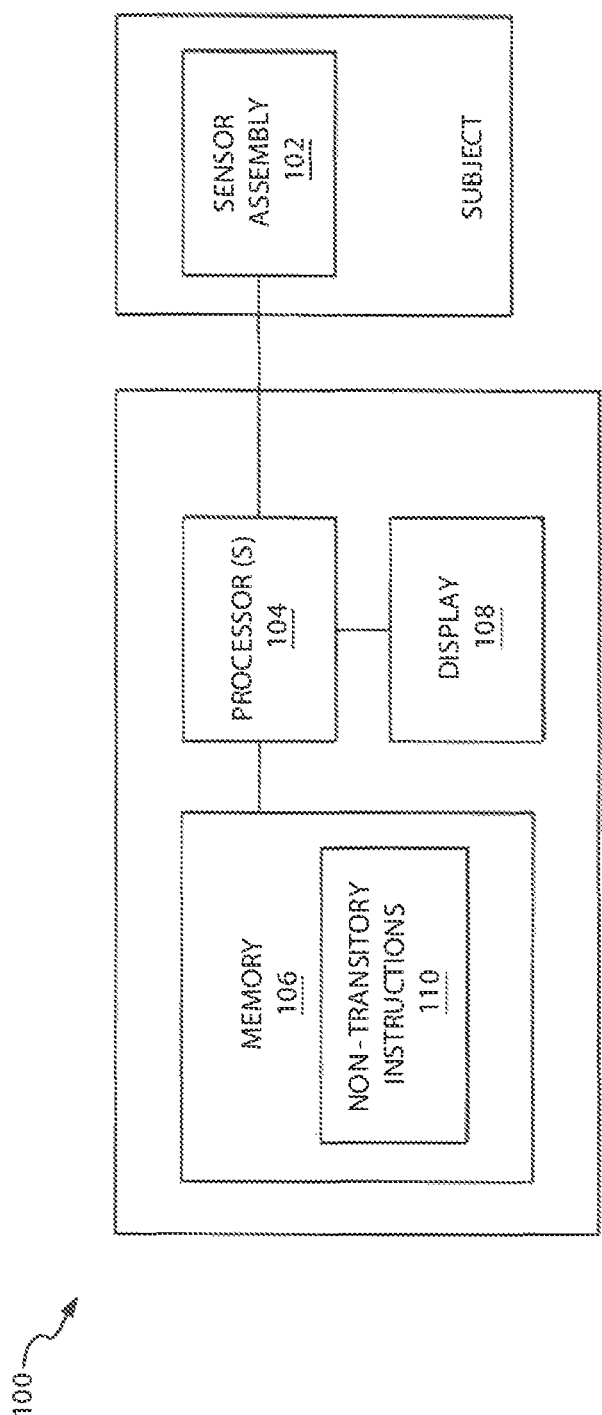
FIG. 1 is schematic block diagrams of an example system, in accordance with aspects of the present disclosure.

To characterize non-stationary signals, such as electrophysiological signals, traditional analyses often employ multitaper ("MT") techniques. These techniques rely on analyzing an interval or "window" in a time-series in which signals are assumed to be stationary. The window is then moved along the time-series and the computation is repeated. Such traditional MT approaches are often advantageous because they can balance the bias-variance trade-off by combining Fourier-based methods with tapering. However, because they treat each window independently, such techniques do not accurately reflect the continuous properties of the time-series. As a result, spectral and other information therefrom obtained may not fully capture the degree of temporal smoothness present in the underlying signals.

In recognizing the limitations of current MT techniques, the present disclosure introduces a novel approach for analyzing non-stationary signals based on a state-space framework, herein referred to as state-space multitaper ("SS-MT"). In some aspects, a random-walk model of non-stationary time-series is used as a sequence of second order stationary processes defined on non-overlapping intervals. The model may relate the spectral representations of Gaussian processes across the different intervals. In this way, the spectral estimate on a first interval, for instance, may be used to compute a new estimate on a second interval subsequent to the first interval. In some aspects, spectral information may be efficiently computed using parallel, one-dimensional complex Kalman filters. In addition, an expectation-maximization algorithm can be used to provide parameter and initial state estimates.

As will become apparent from descriptions below, the present SS-MT framework takes into account the temporal relationship between signals in time-series data, allowing for much more efficient use of data. In addition to the many advantages afforded by the present disclosure, as described below, the present framework can be used to produce high-resolution spectral information, and other information. Furthermore, the present SS-MT framework offers flexibility in extracting time-domain estimates of signal components and allows for making statistical inferences.

The present SS-MT framework may be utilized in a number of applications. For instance, electrophysiological data acquired from a subject under various clinical or experimental scenarios, including but not restricted to sleep, drug delivery, general or local anesthesia, sedation, coma, hyperthermia, and so on, may be analyzed for purposes of identifying, monitoring, or controlling states of the subject. In addition, the present approach may be broadly applicable to analyzing any non-stationary time-series data, such as speech, image and video signals, seismic and oceanographic recordings, radar emissions, and so on.

In some aspects, the present SS-MT framework can be used to dramatically improve spectrogram estimation compared with traditional MT methods. In one example, as will be described, the present SS-MT framework was applied to spectral analyses of simulated time-series and recordings from patients receiving general anesthesia. Compared with traditional MT techniques, SS-MT produced enhanced spectral resolution and substantial noise reduction (approximately 10-15 dB), and allowed statistical comparisons of spectral properties between arbitrary segments of the time-series.

Referring specifically to FIG. 1, an example system 100, in accordance with aspects of the present disclosure, is shown. In general, the system 100 may be configured for receiving and analyzing electrophysiological signals obtained from a subject. In some non-limiting applications, the system 100 may be a system for monitoring and/or controlling brain states of a subject. As shown, the system 100 may generally include a sensor assembly 102, one or more processors 104, a memory 106 and optionally a display 108. The system 100 may include other components not shown, including a power source, various inputs, outputs, integrated electronic components, logic elements, relays, analog/digital converters, and other circuitry. In one configuration, the system 100 may be a portable monitoring system. In another instance, the system 100 may be a pod, without a display, that is adapted to provide electrophysiological parameters, signals or data to an external display or computer.

Specifically, the sensor assembly 102 may include various sensors and sensor types, including electrophysiological sensors. Each sensor may be configured to sense signals from a subject, and transmit the sensed signals to the system 100 over a cable or using other communication links. By way of example, the sensor assembly 102 may include electroencephalography ("EEG"), electromyography ("EMG"), electrocorticography ("ECoG"), local field potentials ("LFP"), electrocardiography ("ECG"), electrooculography ("EOG"), galvanic skin response ("GSR"), oxygen saturation ("$SAO_2$"), oxygenation sensors, ocular microtremor ("OMT"), and other sensors.

In one embodiment, the sensor assembly 102 includes a single sensor of one of the types described above. In another embodiment, the sensor assembly 102 includes at least two EEG sensors. In still another embodiment, the sensor assembly 102 includes at least two EEG sensors and one or more oxygenation sensors, and the like. In each of the foregoing embodiments, additional sensors of different types are also optionally included. Other combinations of numbers and types of sensors are also suitable for use with the system 100.

By way of example, a given sensor in the sensor assembly 102, such as an EEG sensor, can include a cable. The cable can include three conductors within an electrical shielding. One conductor can receive/provide power, one can provide a ground signal, and one conductor can transmit signals from the sensor. For multiple sensors, one or more additional cables can be provided. In some embodiments, the ground signal is an earth ground, but in other embodiments, the ground signal is a subject ground, sometimes referred to as a subject reference, a subject reference signal, a return, or a subject return. In some embodiments, the cable carries two conductors within an electrical shielding layer, and the shielding layer acts as the ground conductor. Electrical interfaces in the cable can enable the cable to electrically connect to electrical interfaces in a connector of the system 100. In some embodiments, various sensors in the sensor assembly 102 and the system 100 may communicate wirelessly.

Although not shown in FIG. 1, the system 100 may include an input configured to receive signals from the sensor assembly 102. As described above, the input may include various electrical interfaces for receiving signals from a cable, for example. Alternatively, or additionally, the input may be configured to receive signals wirelessly. The system 100, sensor assembly 102, and/or input may also include various hardware and electronic elements for pre-processing signals acquired using the sensor assembly 102, including capabilities for amplifying, filtering, sampling, and digitizing signals. Pre-processed signals may be thereafter analyzed by the processor(s) 104.

In addition to being configured to carry out various processes of the system 100, the processor(s) 104 may be configured to execute steps, in accordance with methods of the present disclosure. To do so, the processor(s) 104 may execute non-transitory instructions 110 stored in the memory 106, as well as instructions received via input. As such, the processor(s) 104 may include one or more general-purpose programmable processors, such as central processing units ("CPUs"), graphical processing units ("GPUs"), microcontrollers, and the like. Alternatively, or additionally, the processor(s) 104 may include one or more processors having hardwired instructions or programming. Such processors may therefore be application-specific due to the hardwired instructions or programming therein.

In some aspects, the processor(s) 104 may be configured to apply a SS-MT framework to analyze signals received from the sensor assembly 102, and generate spectral information, as will be described. For example, the processor(s) 104 may be configured to generate spectral information in the form of high-resolution spectrograms, power spectra, and so on. Specifically, spectrograms describe the variation of spectral power at different frequencies over time. The processor(s) 104 may also be configured to determine current and future brain states of a subject based on spectral and other information. Example brain states may include states of anesthesia, sedation, or sleep.

In some aspects, the processor(s) 104 may determine various spectral signatures based on the spectral information obtained using a SS-MT framework. The processor(s) 104 may then utilize the spectral signatures to determine the brain states. For example, the spectral signatures may include specific features(i.e. total power, or power in one or more frequency bands, or relative power between various frequency bands) or trends (i.e. absolute or relative power changes, or power changes in one or more frequency bands), for instance, as ascertained from power spectra or spectrograms. The processor(s) 104 may then compare the spectral signatures to reference signatures to determine the brain states. The reference signatures may be stored in a database, for instance, listing or tabulating various signatures and brain states. Other signatures, including waveform, and coherence signatures may also be obtained and considered by the processor(s) 104 when determining the brain states.

The processor(s) 104 may then communicate analyzed signals, and information obtained therefrom, to an output, such as a display 106 if it is provided. Alternatively, or additionally, the processor(s) 104 may store raw and/or processed signals, information and data in the memory 106.

In some aspects, the processor(s) 104 may be configured generate feedback for controlling the subject. Specifically, the processor(s) 104 may identify a manner for achieving a predetermined or target brain state relative to determined brain states. For instance, based on a current level of anesthesia, as determined by analyzing EEG signals, for example, the processor(s) 104 may determine a drug dose, or infusion rate, sufficient to achieve a target level of anesthesia. Such determination may take into account subject characteristics, including age, height, weight, gender, medical condition and history, administered drugs or compounds, and so on. Feedback may then be provided to a clinician, in the form of a report. Alternatively, or additionally, feedback may be relayed to external equipment, such as a drug delivery system or infusion pump. To this end, the feedback may include information, or be in the form of control signals actionable or executable by such external equipment.

In some embodiments of the system 100 shown in FIG. 1, all of the hardware used to receive, process and analyze signals from the sensor assembly 102 may be housed within the same housing. In other embodiments, some of the hardware may be housed within separate housings. For instance, in one embodiment, the display 106 is incorporated in the system 100. In another embodiment, the display 106 may be separate from the system 100.

Figure 2:
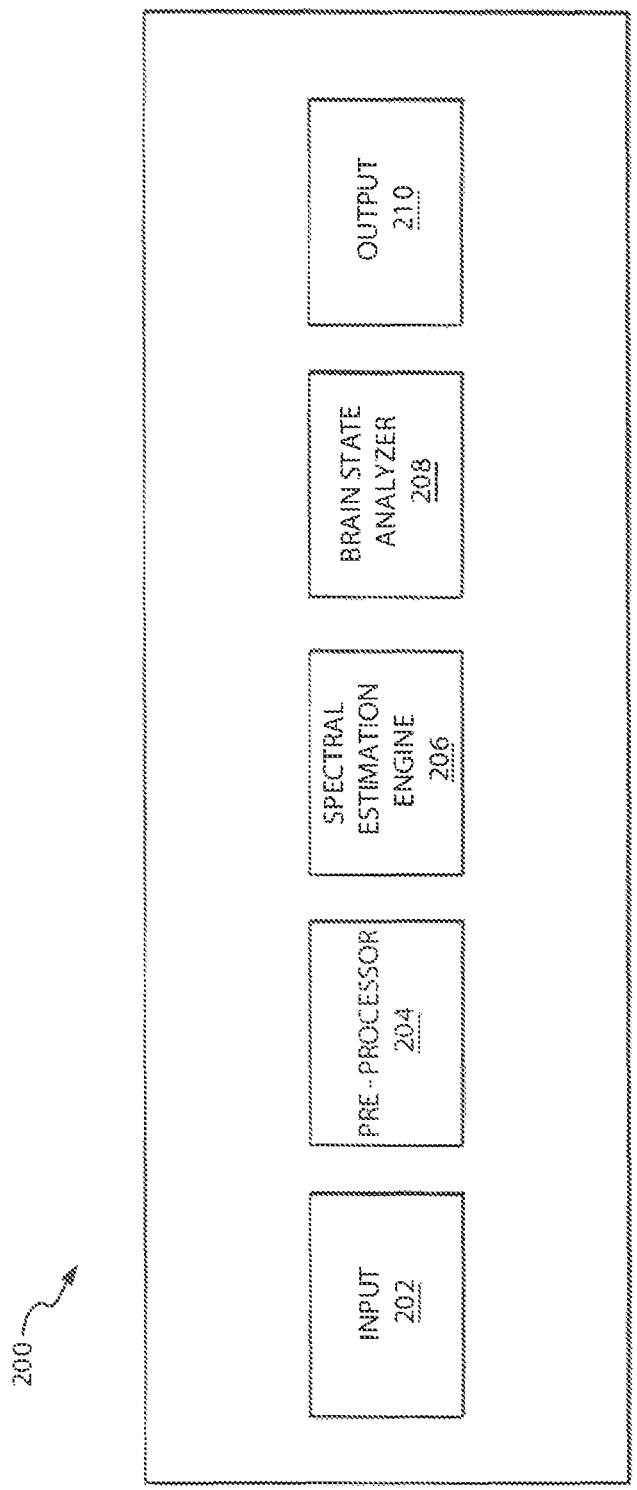
FIG. 2 is a schematic block diagram of another example system, in accordance with the present disclosure.

Referring now to FIG. 2, another example system 200 is illustrated in accordance with aspects of the present disclosure. In some implementations, the system 200 may utilize a SS-MT framework to generate improved spectral information for determining brain states of a subject. As shown, the system 200 may generally include an input 202, a pre-processor 204, a spectral estimation engine 206, a brain state analyzer 208, and an output 210. Some or all of these modules can be implemented in the system 100 described with respect to FIG. 1, or another suitable system.

The input 202 may include a variety of input elements and interfaces. For instance, in some implementations, the input 202 may be configured to receive electrophysiological signals detected by various sensors in a sensor assembly, as described with reference to FIG. 1. The input 202 may also be configured to receive information, data, as well as operational instructions or input from a user.

The pre-processor 204 may be configured to receive and pre-process signals and data from the input 202. For instance, the pre-processor 204 may sample and assemble a time-domain representation of acquired electrophysiological signals. The pre-processor 204 may also digitize raw or pre-processed signals to generate data. As such, the pre-processor 204 may include one or more analog-to-digital converters. In addition, the pre-processor 204 may also be configured to perform any desirable amplification, scaling, and filtering of signals or data. To do so, the pre-processor 204 may include various hardware, electronic and logic components and circuitry.

In some aspects, the pre-processor 204 may also be configured to receive and relay information or input from a user. For example, the pre-processor 204 may receive information related to a medical procedure performed on a subject, such as anesthesia or sedation. As such, information received by the pre-processor 204 may specify drugs or drug compound(s) administered, drug timings, drug doses, infusion rates, and so on. The pre-processor 204 may also receive information related to characteristics of the subject, such as age, height, weight, gender, medical condition or history, and so on.

The spectral estimation engine 206 may include one or more processors configured to receive pre-processed data from the pre-processor 204 and carry out various steps necessary for generating spectral information, in accordance with aspects of the present disclosure. To do so, the spectral estimation engine 206 may apply a SS-MT framework, as will be described. In some aspects, the spectral estimation engine 206 may generate spectrograms, power spectra and so on.

The spectral estimation engine 206 may then provide spectral information to the brain state analyzer 208. In turn, the brain state analyzer 208 may analyze the spectral information to determine various brain state(s) of the subject. For instance, the brain state analyzer 208 may utilize spectral signatures to determine the brain states(s), as described. The brain state analyzer 208 may also consider other information in the analysis, such as characteristics of the subject and details regarding any medical procedure performed on the subject. Such information may be received from the input 202 or the spectral estimation engine 206. In some aspects, the brain state analyzer 208 may be configured to determine current and/or future states of consciousness or sedation of a patient under anesthesia or sedation, as well as confidence intervals or indications with respect to the determined state(s). The brain state analyzer 208 may also determine sleep states of the subject.

Information corresponding to the determined state(s) may then be relayed to the output 210, along with any other desired information, in the form of a report generated either intermittently or in real time. For instance, the report may be provided to a display. The report may include a variety of information, including acquired signals, generated high-resolution spectral information, brain states or brain state indicators, patient characteristics, and so forth. The report may also provide feedback for controlling a subject. As mentioned, such feedback may be in the form of control signals actionable or executable by external equipment to control a subject.

Figure 3:
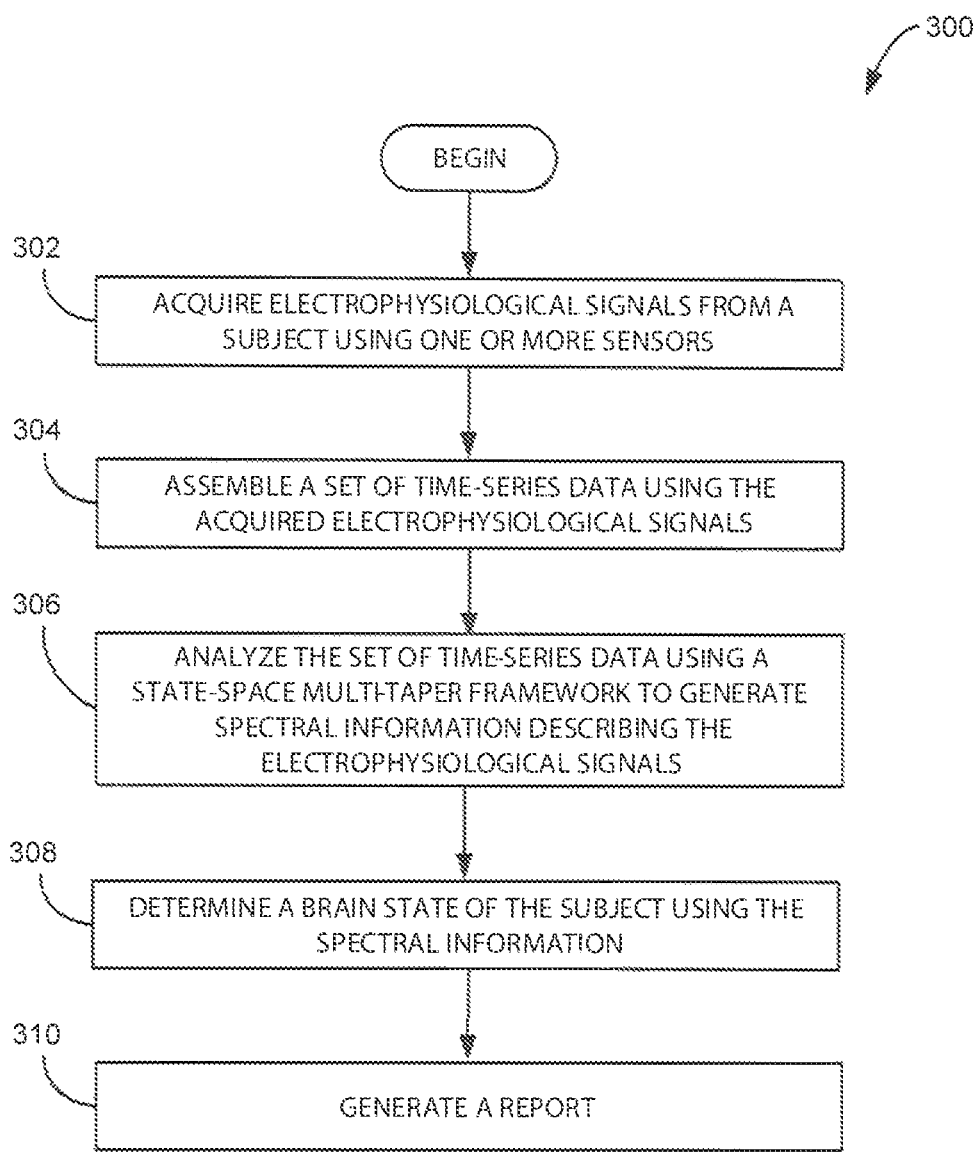
FIG. 3 is a flowchart setting forth steps of a process, in accordance with aspects of the present disclosure.

Turning now to FIG. 3, a flowchart setting forth the steps of a process 300, in accordance with aspect of the present disclosure, is shown. The process 300, or various steps therein, may be carried out using any suitable devices or systems, such as systems described with reference to FIG. 1. In some aspects, the process 300 may be implemented as a program or executable instructions stored in non-transitory computer readable media or hardwired.

The process 300 may begin at process block 302, with acquiring electrophysiological signals from a subject. The electrophysiological signals may be acquired from a subject using one or more sensors, either independently or in a substantially concomitant fashion. Examples electrophysiological signals may include EEG, EMG, ECoG, LFP, ECG, EOG, GSR, $SAO_2$, OMT, and other electrophysiological signals. Specifically, electrophysiological signals may be acquired during a variety of clinical or experimental scenarios, such as during sleep, drug delivery, general or local anesthesia, sedation, coma, hypothermia, and so forth. In some aspects, electrophysiological signals or data may be alternatively retrieved from a memory, database, server, or other data storage location at process block 302.

The acquired/retrieved electrophysiological signals or data may undergo various pre-processing steps. For instance, the electrophysiological signals or data may be amplified, scaled, and/or filtered to substantially reduce or eliminate noise therein. Pre-processed electrophysiological signals may then be assembled into a set of time-series data, as indicated by process block 304.

The process 300 may continue at process block 306, with analyzing the assembled time-series data using a SS-MT framework to generate spectral information describing the acquired electrophysiological signals. In some aspects, electrophysiological data, such as EEG data, may be assembled into time-frequency representations or spectrograms. Other representations may also be possible. Spectral information determined at process block 306 may then be used to determine brain states of the subject, such as depths of anesthesia, levels of sedation, sleep states, and so forth. As described, spectral signatures, as well as other signatures, may be utilized to determine the brain states. In particular, spectral signatures, based on features ascertained from one or more assembled spectrograms, may be analyzed and/or tracked at different time points to determine current and/or future brain states.

At process block 310 a report may be generated. The report may be in any form and include a variety of information. For instance, the report may be a graphical illustration provided via a display. The report may indicate tracked electrophysiological parameters, such as EEG signals, as well as other electrophysiological (e.g. heart rate, behavioral response rate, sleep stage, and so on) or pharmacological (drug infusion rate, drug effect site concentration, and so on) correlates. The report may also include spectral information, brain states, and other information.

The report may be generated and/or updated in substantially real time, as new electrophysiological signals or data become available, or may be generated after all electrophysiological data provided has been processed. In some aspects, the report may provide feedback, in the form of intermittent or continuous signals, to control a subject based on brain states determined. For example, in a closed-loop system, feedback may be provided to an infusion pump, other drug delivery system, controlling anesthesia administered to the subject.

Process blocks 302-310 may be repeated, as desired or upon fulfillment of a termination condition. For example, a termination condition may be expressly fulfilled by an indication for termination provided by a user. Alternatively, a termination condition may be fulfilled if an error in signal acquisition is encountered or if analysis of a dataset is completed. In some aspects, process blocks 302-310 may be repeated to continuously or intermittently monitor, track and optionally control brain states of a subject.

In what follows a SS-MT framework, based on a time-frequency model is described. It may be assumed that observations produce non-stationary time-series of the form $$y_t = x_t + \varepsilon_t \tag{1}$$

where $x_t$ is a zero mean, second-order, locally stationary Gaussian process, and $\varepsilon_t$ is independent, zero mean Gaussian noise with common variance $\sigma_\varepsilon^2$ for $t=1, 2, \ldots, T$. The local stationarity of $x_t$ may be defined by assuming that one can write $T=KJ$, where $K$ defines the number of distinct, non-overlapping intervals on which $x_t$ is stationary and $J$ is the number of observations per stationary interval. The stationary intervals can be indexed as $k=1, \ldots, K$ and the points per interval as $j=1, \ldots, J$. For example, if 1,440 seconds of a time-series are recorded at 250 Hz, then $K=1,440$, $J=250$ and $T=360,000$.

In some aspects, to relate data on adjacent intervals, Gaussian increment differences linked by a random walk model may be assumed. In addition, the data on stationary interval k can be presented as the vector $Y_k$ of length $J$ whose jth element is $Y_{k,j}=y_{J(k-1)+j}$, $X_{k,j}=x_{J(k-1)+j}$ and $\varepsilon_{k,j}=\varepsilon_{J(k-1)+j}$ for $k=1, \ldots, K$ and $j=1, \ldots, J$. Using the spectral representation theorem one can express each $Y_k$ as $$Y_k = X_k + \varepsilon_k = W\Delta Z_k + \varepsilon_k, \tag{2}$$

where W is a J×J matrix whose (l,j)th element is $(W)_{l,j}=$ $$J^{-1/2}\exp\left(\frac{i2\pi(l-1)}{J}j\right),$$

$\Delta Z_k=(\Delta Z_k(\omega_1), \ldots, \Delta Z_k(\omega_J))'$ are differences of orthogonal Gaussian increments, where $\omega_j$ may be defined as $\omega_j=2\pi(j-1)/J$.

Because the length of the stationary intervals is finite, the bias-variance trade-off in estimating the spectrum on each stationary interval can be balanced by applying MT spectral methods using Slepian functions. It may be assumed that for the given time-series, a number of tapers M has been chosen, and the tapers indexed as $m=1, \ldots, M$. Let $S^{(m)}$ denote the operator for applying the mth Slepian taper to the data. The tapered data may be defined as $Y_k^{(m)}=S^{(m)}Y_k$.

Let F be the Fourier transform operator defined as the J×J matrix whose (l,j)th element is $$(F)_{l,j} = J^{-1/2}\exp\left(-\frac{i2\pi(l-1)}{J}j\right).$$

Define $Y_k^{(m),F}=FY_k^{(m)}$ as the Fourier transform of the data to which the taper m has been applied. One may then define $$f_k^{MT}(\omega_j) = M^{-1}\sum_{m=1}^{M}\|Y_{k,j}^{(m),F}\|^2, \tag{3}$$

as the MT spectrogram estimate at frequency $\omega_j$ on interval k, where $\|Y_{k,j}^{(m),F}\|^2$ is the mth eigenspectrogram. Each eigenspectrogram is a spectrogram estimate computed by weighting the data with a different Slepian taper. The MT spectrogram estimate (Eq. 3) is the average of the M approximately independent eigenspectrograms.

Taking the Fourier transform of Eq. 2 yields $$Y_k^F = \Delta Z_k + \varepsilon_k^F, \tag{4}$$

where $Y_k^F=FY_k$, $FW=I$, and $\varepsilon_k^F=F\varepsilon_k$ is a zero mean, complex Gaussian vector with J×J covariance matrix $I(\sigma_\varepsilon^2)$. If one takes the Slepian tapers to be orthonormal, then the Fourier transform of each tapered series has the same probability distribution as $Y_k^F$, and thus, a spectral representation that agrees with the spectral representation in Eq. 4. Therefore, one can write $$Y_k^{(m),F} = \Delta Z_k^{(m)} + \varepsilon_k^{(m),F}. \tag{5}$$

$\Delta Z_k^{(m)}$ can be viewed as a realization of $\Delta Z_k$ and $\varepsilon_k^{(m),F}$ as a realization of $\varepsilon_k^F$ observable through the mth tapered series.

Applying MT methods to successive non-overlapping intervals assumes that the data are stationary separately on each interval. However, it is unlikely that data on adjacent intervals are unrelated. Therefore, one can relate the data on adjacent intervals by assuming that, for each tapered series, the Gaussian increment differences are linked by a random walk model having the form $$\Delta Z_k^{(m)} = \Delta Z_{k-1}^{(m)} + v_k^{(m)}, \tag{6}$$

where it may be assume that $v_k^{(m)}$ is a zero mean, independent complex Gaussian vector with a J×J diagonal covariance matrix $I(\sigma_{v,j}^{2,(m)})$ for $j=1, \ldots, J$ and $m=1, \ldots, M$. Equation 6 defines stochastic continuity constraints on the non-stationary time-series. Equations 5 and 6 define a state-space multitaper time-frequency model.

The linear complex Gaussian form of Eqs. 5 and 6 suggests that a Kalman filter algorithm can be used to compute the sequence of increment differences and thus, the sequence of spectrum estimates. For this problem the Kalman filter has a special structure. Because the M $\Delta Z_k^{(m)}$ are independent, there are M separate, independent J-dimensional Kalman filters. In addition, because the $\Delta Z_k^{(m)}(\omega_j)$ are orthogonal across frequencies, there are, for each tapered series. J parallel one-dimensional complex Kalman filter algorithms, one for each frequency $\omega_j$. Hence, the Gaussian increment differences can be recursively estimated by applying M J one-dimensional complex Kalman filter algorithms to the M tapered time-series. Assuming that the increment difference estimates have been computed on interval k−1, then, for tapered series m, the one-dimensional complex Kalman filter algorithm for estimating $\Delta Z_k^{(m)}(\omega_j)$ on interval k is $$\Delta Z_{k|k-1}^{(m)}(\omega_j) = \Delta Z_{k-1|k-1}^{(m)}(\omega_j) \tag{7a}$$

$$\sigma_{k|k-1,j}^{2,(m)} = \sigma_{k-1|k-1,j}^{2,(m)} + \sigma_{v,j}^{2,(m)} \tag{7b}$$

$$\Delta Z_{k|k}^{(m)}(\omega_j) = \Delta Z_{k|k-1}^{(m)}(\omega_j) + C_{k,j}^{(m)}(Y_{k,j}^{(m),F} - \Delta Z_{k|k-1}^{(m)}(\omega_j)) \quad (7c)$$

$$\sigma_{k|k,j}^{2,(m)} = (1 - C_{k,j}^{(m)})\sigma_{k|k-1,j}^{2,(m)}, \quad (7d)$$

where the Kalman gain for m=1, ..., M, k=1, ..., K, and j=1, ..., J is $$C_{k,j}^{(m)} = (\sigma_\varepsilon^{2,(m)} + \sigma_{k|k-1,j}^{2,(m)})^{-1}\sigma_{k|k-1,j}^{2,(m)}, \quad (8)$$

The notation k|s denotes the estimate on stationary interval k given all of the data observed through stationary interval s. The derivation of the Kalman filter algorithm is described below. One may assume that the algorithm has initial conditions $aZ_0^{(m)}(\omega_j)$ and $\sigma_{0,j}^{2,(m)}$ whose estimation can be carried out along with the model parameters using an expectation-maximization (EM) algorithm. Given the Kalman filter estimate of the increment differences on interval k, the SS-MT spectrogram estimate at frequency $w_j$ on interval k is then:

$$f_{k|k}^{SS-MT}(\omega_j) = M^{-1}\sum_{m=1}^{M}\|\Delta Z_{k|k}^{(m)}(\omega_j)\|^2. \quad (9)$$

Equations 7-9 define the SS-MT algorithm for spectrogram estimation for non-stationary time-series. For each tapered series, the increment difference estimate on interval k is a weighted average between the increment difference estimate on interval k−1 and the difference between the Fourier transform of the tapered series and the increment difference estimate on interval k−1. The weighting may depend on the Kalman gain, which may between 0 and 1. If the Kalman gain is close to 0, then the one-step prediction variance $\sigma_{k|k-1,j}^{2,(m)}$ is small relative to the observation variance $\sigma_\varepsilon^{2,(m)}$, and hence, the increment difference estimate on interval k is close to the estimate on interval k−1. If the Kalman gain is close to 1, then the one-step prediction variance is large relative to the observation variance, meaning that the uncertainty in the prediction of the increment difference on interval k based on the data up through interval k−1 is large. In this case, the increment difference estimate on interval k is close to the Fourier transform of the tapered series observed on interval k.

In the absence of tapering, Eq. 9 becomes the state-space ("SS") periodogram estimate $$f_{k|k}^{SS-P}(\omega_j) = \|\Delta Z_{k|k}^{SS-P}(\omega_j)\|^2, \quad (10)$$

which is computed by applying J parallel one-dimensional complex Kalman filters to the Fourier transformed data $Y_k^F$. In the absence of tapering and the state-space model, Eq. 1 becomes the periodogram estimate $$f_k^P(\omega_j) = \|Y_{k,j}^F\|^2, \quad (11)$$

where $Y_k^F = (Y_{k,1}^F, \ldots, Y_{k,J}^F)'$. By comparing the SS-MT algorithm (Eqs. 7-9) with the standard MT (Eq. 10), the periodogram (Eq. 2), and the SS periodogram (Eq. 1) algorithms, it is possible to understand the effects on spectrogram estimation of combining the multitaper approach with state-space modeling.

Given the $\Delta Z_{k|k}^{(m)}$, one can estimate the denoised time-domain signal as $$X_{k|k} = W\Delta Z_{k|k}, \quad (12)$$

where $\Delta Z_{k|k} = M^{-1}\sum_{m=1}^{M}\Delta Z_{k|k}^{(m)}$. The extracted signal is a linear combination of the estimated increment differences across all of the frequencies. Frequency components on different stationary intervals are related because all are estimated by the complex Kalman filter algorithm in Eqs. 7a-7d. Hence, elective filtering, such as high-pass, low-pass, and band-pass filtering can be performed by simply choosing the components of $\Delta Z_{k|k}$ in the desired frequency range. Given a set of L, not necessarily sequential frequencies, $\omega_j$ for $j=s_1, \ldots, s_L$, we can obtain the filtered time-domain signal as $$X_{k|k}^L = W\Delta Z_{k|k}^L, \quad (13)$$

where the components of $\Delta Z_{k|k}^L$, outside the L frequencies and their conjugate symmetric frequencies, are all zero. Eq. 4 provides a highly flexible alternative to EMD that allows extraction of a time-domain signal comprised of any specified frequency components. The analytic version of the filtered time-domain signal can be computed as $$R_{k|k,t}^L + iI_{k|k,t}^L = 2J^{-\frac{1}{2}}\sum_{j=s_1}^{s_L}\Delta Z_{k|k}^L(\omega_j)e^{i\omega_j t}, \quad (14)$$

for t=J(k−1)+l and l=1, ..., J. Here, $[(R_{k|k,t}^L)^2 + (I_{k|k,t}^L)^2]^{1/2}$ and $\tan(-I_{k|k,t}^L/R_{k|k,t}^L)$ are the instantaneous amplitude and phase of the time-domain signal in the specified frequency range. This computation obviates the need to apply a Hilbert-Huang transform to either filtered or EMD processed data to estimate instantaneous amplitude and phase.

To make inferences for functions of the increment differences at any time points, we compute the joint distribution of the increment differences conditional on all of the data in the time-series using the fixed-interval smoothing algorithm, which is $$\Delta Z_{k|K}^{(m)}(\omega_j) = \Delta Z_{k|k}^{(m)}(\omega_j) +$$

$$A_{k,j}(\Delta Z_{k+1|K}^{(m)}(\omega_j) - \Delta Z_{k+1|k}^{(m)}(\omega_j))$$

$$\sigma_{k|K,j}^{2,(m)} = \sigma_{k|k,j}^{2,(m)} + A_{k,j}^2(\sigma_{k+1|K,j}^{2,(m)} - \sigma_{k+1|k,j}^{2,(m)})$$

$$A_{k,j} = \sigma_{k|k,j}^{2,(m)}(\sigma_{k+1|k,j}^{2,(m)})^{-1}, \quad (15)$$

where the initial conditions are $\Delta Z_{K|K}^{(m)}(\omega_j)$ and $\sigma_{K|K,j}^{2,(m)}$ for k=K−1, K−2, ..., 1 and j=1, 2, ..., J. To compute the covariances between any two states one can use the covariance smoothing algorithm defined as $$\sigma_{k,u|K,j}^{(m)} = A_{k,j}\sigma_{k+1,u|K,j}^{(m)}, \quad (16)$$

for 1≤k<u≤K. Equations 6 and 7 allow computation of the joint distribution of the increment differences conditional on all of the data. Therefore, one can compute the distribution of any function of the increment differences by Monte Carlo methods. For each Monte Carlo sample one can draw from the joint distribution and compute the function of interest. The histogram of the function of interest provides a Monte Carlo estimate of its posterior probability density. The estimate is empirical Bayes' because it is computed conditional on the maximum likelihood parameter estimates.

The Kalman filter (Eqs. 7 and 8), Kalman smoother (Eq. 15) and covariance smoothing (Eq. 16) algorithms assume that the initial states $\Delta Z_0^{(m)}(\omega_j)$, the initial state variances $\sigma_{0,j}^{2,(m)}$, and the model parameters $\sigma_{v,j}^{2,(m)}$ and $\sigma_\varepsilon^{2,(m)}$ are known. One can use an EM algorithm to compute maximum likelihood estimates of the initial conditions and the model parameters.

By making standard assumptions regarding joint local stationarity between two or more time-series, the SS-MT paradigm can be extended to compute SS-MT cross-spectrograms. It is assumed that one can compute on interval k, the Fourier transforms of tapered data series $Y_k^{r,(m),F}$ and $Y_k^{s,(m),F}$ from recording locations r and s, respectively. The corresponding increment difference estimates can be computed from the two locations as $\Delta Z_{k|k}^{r,(m)}(\omega_j)$ and $\Delta Z_{k|k}^{2,(m)}(\omega_j)$, the mth SS-MT eigencross-spectrogram as $$f_{k|k}^{SS-MT(r,s)(m)}(\omega_j) = \Delta Z_{k|k}^{r,(m)}(\omega_j) \cdot \Delta Z_{k|k}^{s,(m)}(\omega_j)^* \qquad (17)$$

and the SS-MT cross-spectrogram estimate is $$f_{k|k}^{SS-MT(r,s)}(\omega_j) = M^{-1} \sum_{m=1}^{M} f_{k|k}^{SS-MT(r,s)(m)}(\omega_j). \qquad (18)$$

The corresponding SS-MT coherogram estimate is $$C_{k|k}^{r,s}(\omega_j) = \frac{\|f_{k|k}^{SS-MT(r,s)}(\omega_j)\|}{\left(f_{k|k}^{SS-MT(r,r)}(\omega_j) \cdot f_{k|k}^{SS-MT(s,s)}(\omega_j)\right)^{\frac{1}{2}}}. \qquad (19)$$

Figure 4A:
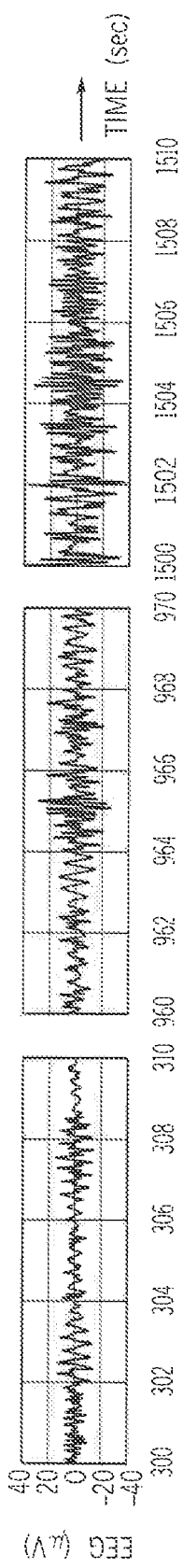
FIG. 4A shows a spectrogram analysis of the time-varying AR(6) process defined in Eq. 20, with 10-second segments from the simulated time-series starting at 5, 16, and 25 minutes.

To demonstrate the power of the present SS-MT algorithm, an example non-stationary process (FIG. 4A) was simulated using the following sixth-order autoregressive model:

$$x_t = 3.9515 x_{t-1} + 7.8885 x_{t-2} + 9.7340 x_{t-3} + \qquad (20)$$
$$7.7435 x_{t-4} + 3.8078 x_{t-5} + 0.9472 x_{t-6} + \frac{16t}{T} v_t$$

where T=128,000 s and $v_t$ is independent, zero-mean Gaussian noise with unit variance. Using this model, the true spectrogram (FIG. 4B), as well as a periodogram (FIG. 4C), a MT spectrogram (FIG. 4D), a SS periodogram (FIG. 4E), and a SS-MT spectrogram (FIG. 4F), in accordance with aspects of this disclosure, were computed. Specifically, the true spectrogram of the model includes three peaks at 3.5 Hz, 9.5 Hz, and 11.5 Hz that grow linearly in height and width with time. In performing these computations, the number of observations per stationary interval was selected to be J=1024 and the number of non-overlapping intervals as K=125. In particular, for the MT computations, the number of tapers was selected to be M=4, which correspond to a spectral resolution of approximately 0.5 Hz. Also, model parameters were estimated from the first 50 observations using the EM algorithm. Other parameter selections may also be possible.

While the various periodograms and spectrograms illustrated shown in FIGS. 4C-4F capture the general structure of the true spectrogram (FIG. 4B), there are clear differences. Specifically, the MT spectrogram shows a better resolution of (less variability in estimating) the 3 peaks compared with the periodogram. However, when comparing the power in the frequency bands outside the 3 peaks, both the periodogram and the MT spectrogram overestimate the noise relative to the true spectrogram by about 10 to 15 dB. On the other hand, the SS periodogram and the SS-MT spectrogram estimate the noise outside the 3 peaks to be at or near the −10 dB value of the true spectrogram.

Figure 4B:
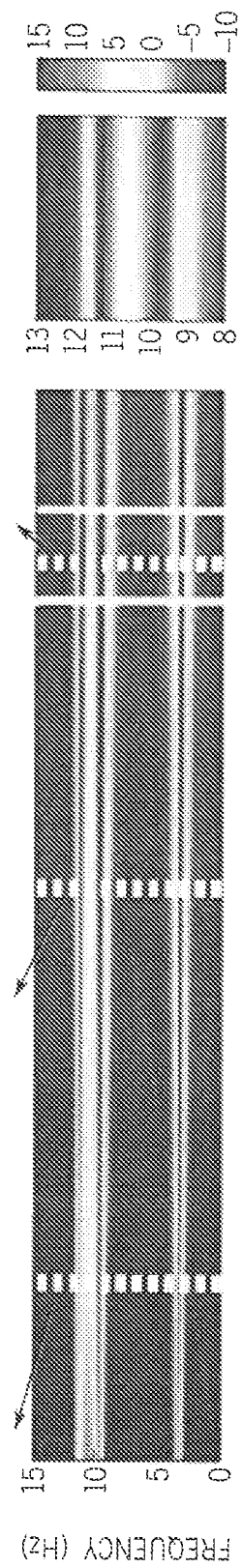
FIG. 4B shows a true spectrogram related to FIG. 4A.
Figure 4C:
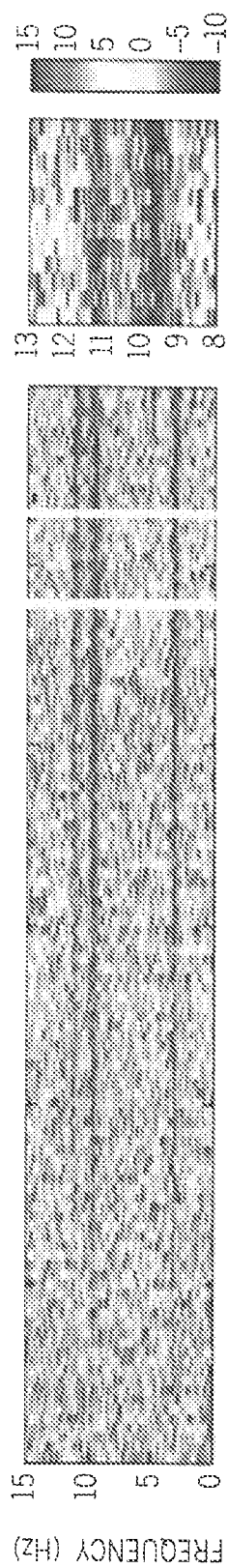
FIG. 4C shows a periodogram related to FIGS. 4A and 4B.
Figure 4D:
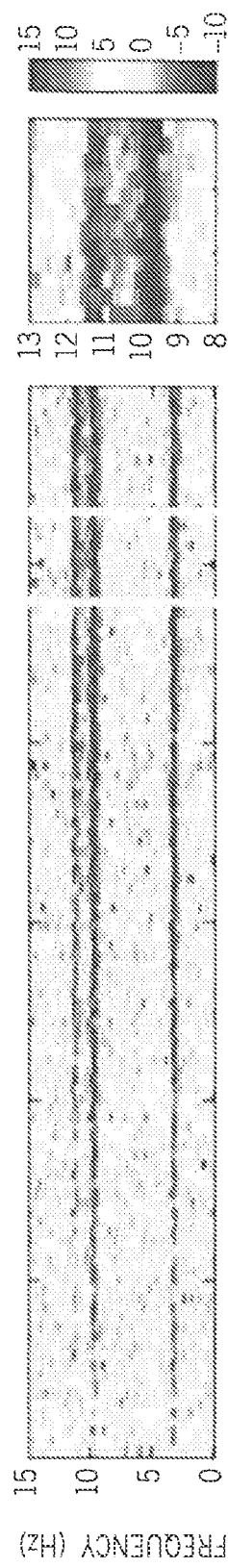
FIG. 4D shows a multitaper ("MT") spectrogram related to FIGS. 4A-4C.
Figure 4E:
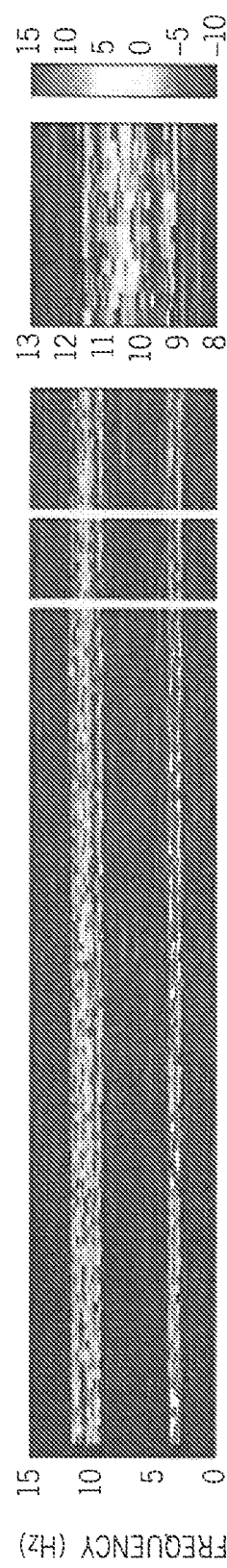
FIG. 4E shows a state-space periodogram in accordance with the present disclosure.
Figure 4F:
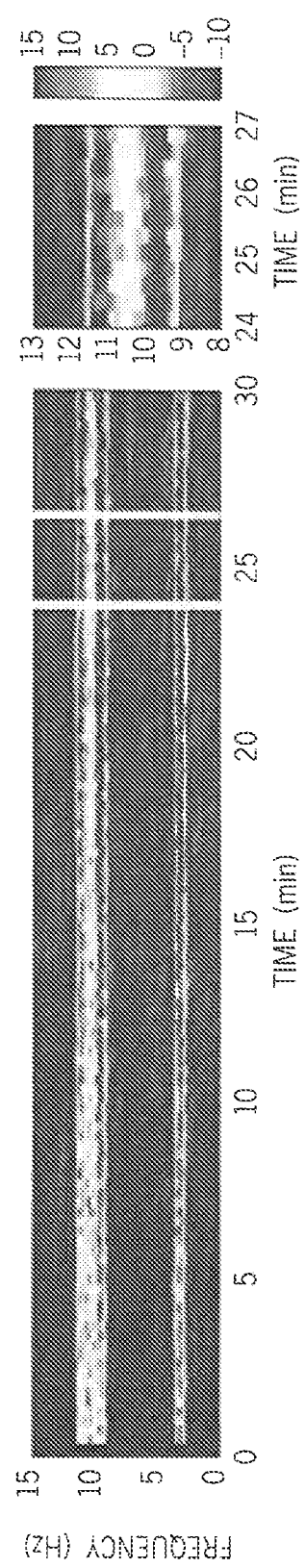
FIG. 4F shows a state-space MT spectrogram in accordance with the present disclosure. The right column shows for each panel a zoomed-in display of the three minutes between 24 to 27 minutes. The color scale is in decibels.

As apparent from FIGS. 4D and 4F, the MT spectrogram and the SS-MT spectrogram agree closely with the true spectrogram in their estimates of the power in the 3 peaks (FIGS. 4D and 4F, second column). However, a key difference between appears as the power level increases. In particular, as shown in FIG. 4B, as the heights of the spectral peaks at 9.5 and 11.5 Hz in the true spectrogram increase, the height of the "valley" between them also increases. This "valley" is at about 5 dB between minutes 24 and 27 (FIG. 4B, second column). The MT spectrogram estimates the "valley" to be at about 10 dB (FIG. 4D, second column). By contrast, the SS-MT spectrogram more accurately estimates the "valley" to be at about 4 dB (FIG. 4D, second column). In addition, the mean square error of the SS-MT spectrogram is lower at all frequencies compared to the periodograms and MT spectrogram computed.

The advantages of the presently described SS-MT algorithm, including enhanced denoising and spectral resolution, may further be appreciated from analysis of real recordings, such as EEG recordings obtained during general anesthesia. In particular, anesthetic drugs act in the brain to create the altered states of general anesthesia by producing highly structured oscillations that disrupt normal information flow between brain regions. Because these oscillations are readily visible in the EEG, EEG and EEG-derived measures are commonly used to track in real time the brain states of patients receiving general anesthesia and sedation.

Figure 5D:
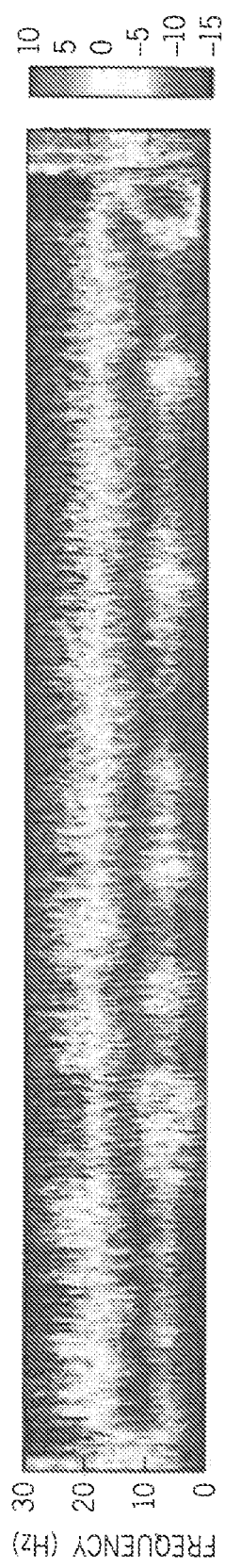
FIG. 5D shows a MT spectrogram associated with FIGS. 5A-5C.
Figure 5E:
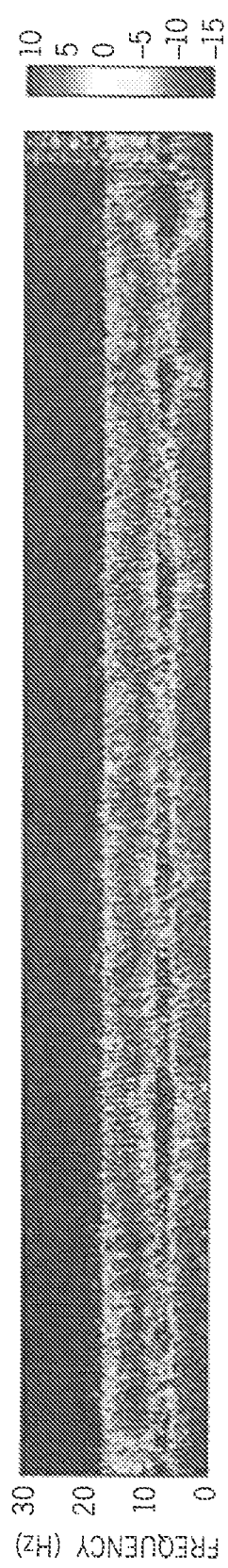
FIG. 5E shows a state-space periodogram associated with FIGS. 5A-5D.
Figure 5F:
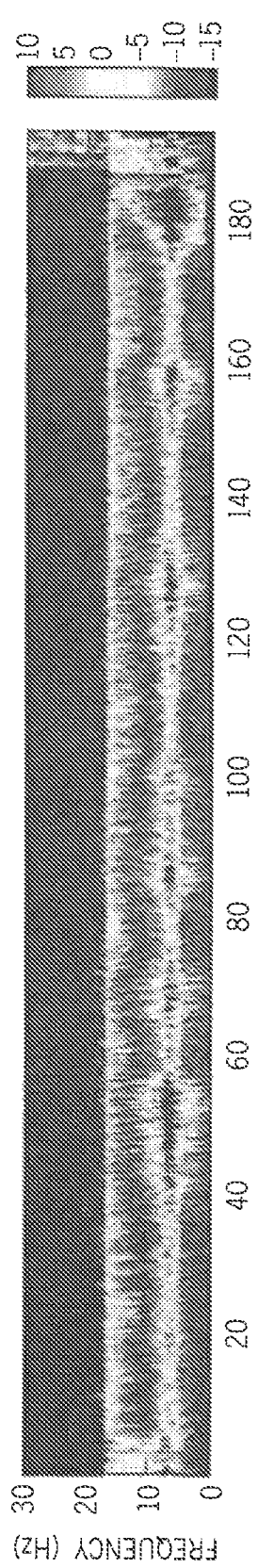
FIG. 5F shows a state-space multi taper ("SS-MT") spectrogram associated with FIGS. 5A-5E, where the color scale is in decibels.

By way of example, FIGS. 5A-5F illustrates data acquired from a patient under general anesthesia maintained with sevoflurane with oxygen. In particular, FIG. 5A shows the expired concentration of sevoflurane, FIG. 5B shows raw EEG recordings, FIG. 5C shows a periodogram, FIG. 5D shows a MT spectrogram, FIG. 5E shows a SS periodogram, and FIG. 5F shows a SS-MT spectrogram, in accordance with aspects of the disclosure.

EEG data was recorded continuously using the Sedline monitor (Masimo, Irvine, Calif.) and a standard six-electrode frontal montage at a sampling frequency of approximately 250 Hz. The electrode array included electrodes located approximately at positions Fp1, Fp2, F7, and F8. For each channel, the electrode impedance was less than 5 kilo-Ohms. The EEG recordings began approximately 3 to 5 minutes prior to induction of general anesthesia and continued for approximately 3 to 5 minutes after extubation, lasting approximately 190 minutes. The EEG data recorded at Fp1 was used for the spectral analyses and EEG data recorded at Fp1 and Fp2 was used for the coherence analyses.

In performing the spectral analysis, parameters selected included. T=2,850,000, J=500, K=5,750, and M=3, which corresponding to a 2 Hz spectral resolution, although it may be appreciated that other parameter selections could have been utilized. Unless specified otherwise, the same choices of M and J values are used in the subsequent examples. The model parameters and initial conditions were estimated from the first 5 minutes of data using the EM algorithm. To estimate the observation noise variance in the EM algorithm, the analysis was restricted to frequencies in the electrophysiologically relevant range of 0.1 to 30 Hz.

The raw EEG signals (FIG. 5B) show strong modulation with changes in the sevoflurane concentration (FIG. 5A). The periodograms and spectrograms for these data showed the well-known alpha-beta oscillations (8 to 17 Hz) and slow-delta oscillations (0.1 to 4 Hz) that are characteristic of general anesthesia maintained by sevoflurane. When the sevoflurane concentration increases, the power in the alpha-beta band shifts to lower frequencies while the power in the slow-delta band power shifts to higher frequencies. The opposite changes occur when the sevoflurane concentration decreases. The spectral changes associated with increases in the sevoflurane concentration appear as increases in theta oscillation power (4 to 8 Hz).

The periodogram (FIG. 5C) shows diffuse, grainy power between 10 to 17 Hz and in the slow-delta range. By comparison, the MT spectrogram (FIG. 5D) has higher spectral resolution relative to the periodogram. Both the periodogram and the MT spectrogram show diffuse power ranging from 7 to −2 dB in the theta range and from −5 to −15 dB in the beta-gamma range (>17 Hz). Compared to the periodogram and the MT spectrogram, the SS-periodogram (FIG. 5E) and the SS-MT spectrogram (FIG. 5F) show substantially greater denoising, which may be defined as a reduction in power in the frequency bands with low power. For the latter two spectrograms, the power in the beta-gamma range lies uniformly at −15 dB, which is a 5 to 15 dB power reduction relative to the MT spectrogram. Both the SS-periodogram and the SS-MT spectrogram estimate the power in the theta band to be 10 to 15 dB less than that for either the periodogram or the MT spectrogram. Like the periodogram, the prominent, alpha-beta and the slow-delta power in the SS-periodogram is grainy and diffuse.

The SS-MT spectrogram of FIG. 5F shows greater denoising compared to the MT spectrogram of FIG. 5D due to the stochastic continuity constraint (Eq. 6) and to the eigenspectrogram averaging. Specifically, the stochastic continuity constraint has a different independent effect at each frequency. In fact, in both the theoretical example of FIG. 4 and the real data example of FIG. 5, the state variances, $\sigma_{v,l}^{2,(m)}$ were small (0.05 to 4 dB) for frequencies with low power and large (27 to 38 dB) for frequencies with high power. The Kalman gains, $C_{k,l}^{(m)}$, reached steady state values within 5 to 10 updates, and like the state variances, the Kalman gains were small (0.1 to 0.4) for frequencies with low power and large (0.7 to 0.95) for frequencies with high power. Rewriting Eq. 7c as $$\Delta Z_{k|k}^{(m)}(\omega_l) = (1 - C_{k,l}^{(m)}) \Delta Z_{k-1|k-1}^{(m)}(\omega_l) + C_{k,l}^{(m)} Y_{k,l}^{(m),F}, \quad (21)$$

shows that the increment difference estimate on interval k is a weighted average between the increment difference estimate on interval k−1 and the Fourier transform of the tapered data on interval k, in particular, frequencies with low power weight $Z_{k-1|k-1}^{(m)}(\omega_l)$ more than $Y_{k,l}^{(m),F}$. Such weighting favors suppressing increases or fluctuations in the low power or noise frequencies. In contrast, frequencies with high power provide more weight to the new information in $Y_{k,l}^{(m),F}$.

Figure 9A:
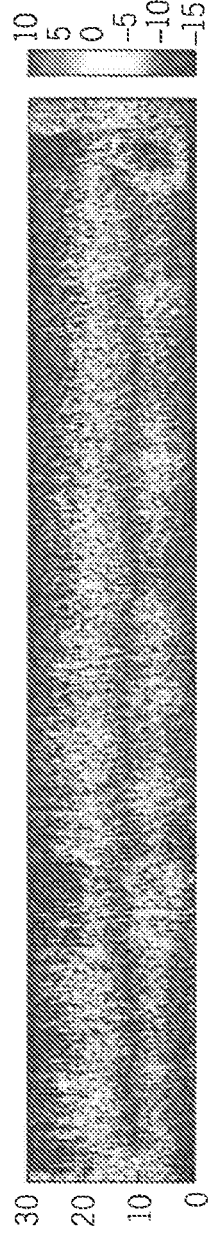
FIG. 9A shows eigenspectrogram and spectrogram estimates of the multitaper method from EEG data recorded from a patient undergoing sevoflurane-induced general anesthesia (FIG. 5) illustrating an eigenspectrogram for a first tapered signal.
Figure 9B:
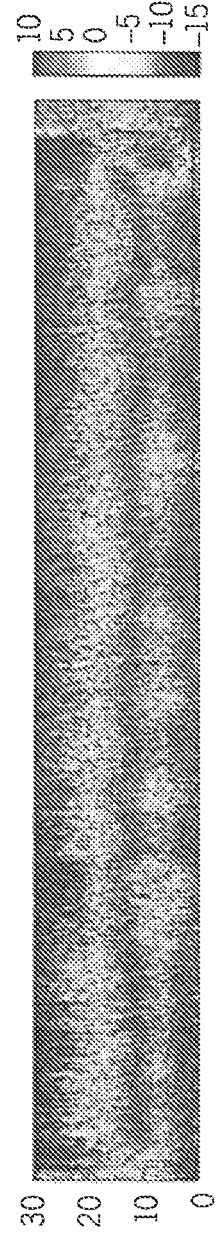
FIG. 9B shows eigenspectrogram and spectrogram estimates of the multitaper method from EEG data recorded from a patient undergoing sevoflurane-induced general anesthesia (FIG. 5) illustrating an eigenspectrogram for a second tapered signal.
Figure 9C:
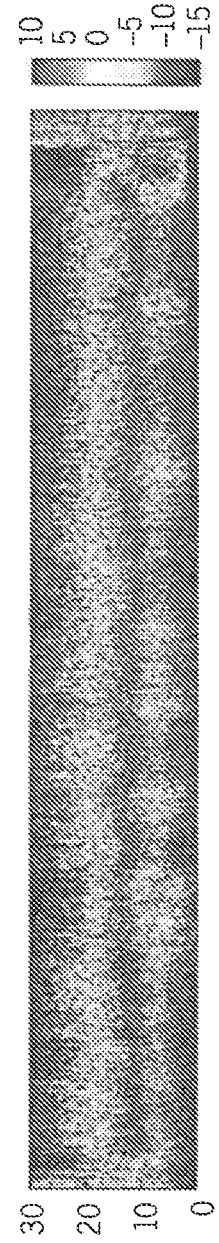
FIG. 9C shows eigenspectrogram and spectrogram estimates of the multitaper method from EEG data recorded from a patient undergoing sevoflurane-induced general anesthesia (FIG. 5) illustrating an eigenspectrogram for a third tapered signal.
Figure 9D:
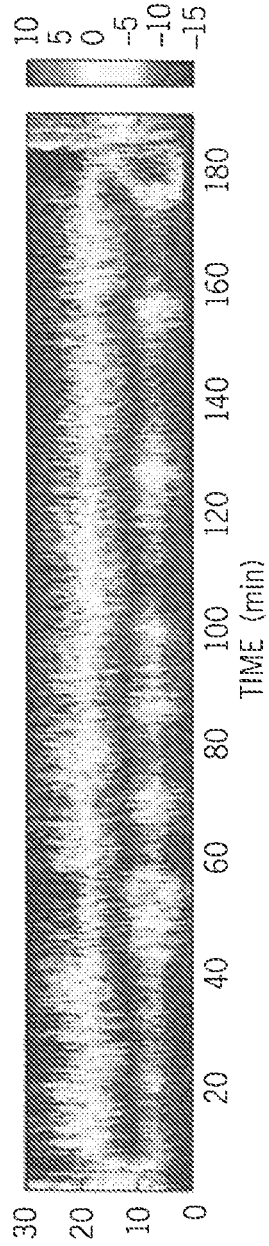
FIG. 9D MT method spectrogram relate to FIGS. 9A-9C. The color scale is in decibels.
Figure 12A:
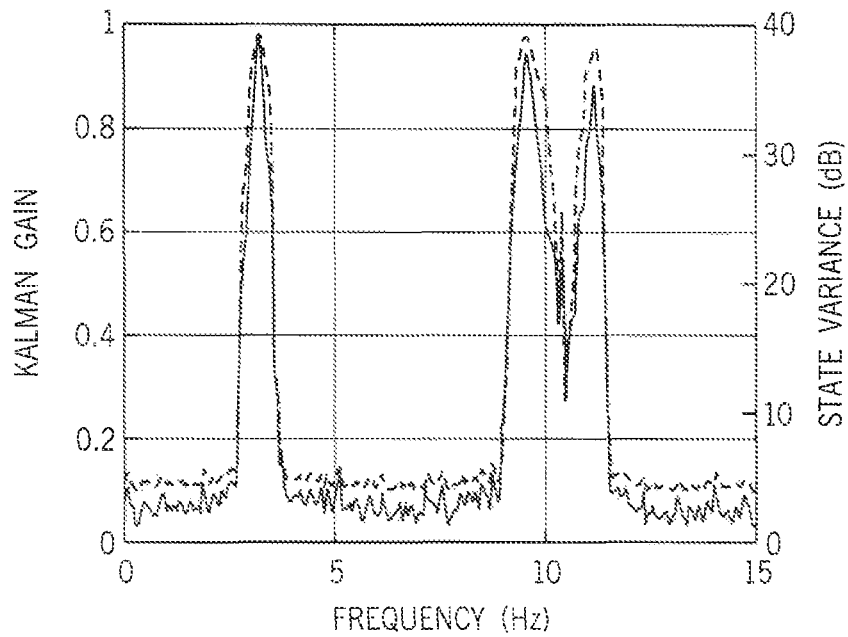
FIG. 12A shows state variance estimates and steady-state Kalman gains for the first tapered time-series plotted as a function of frequency for the complex Kalman filter algorithms used to compute the state-space multitaper spectrogram for the simulated time-series in FIG. 3F.
Figure 12B:
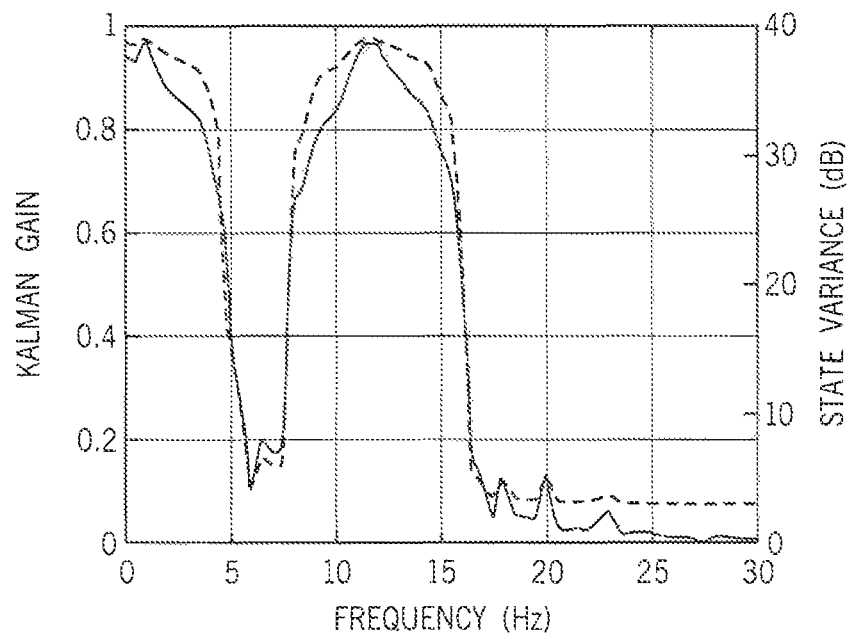
FIG. 12B shows state variance estimates and steady-state Kalman gains for the first tapered time-series plotted as a function of frequency for the complex Kalman filter algorithms used to compute the state-space multitaper spectrogram for the EEG time-series in FIG. 5F.
Figure 13A:
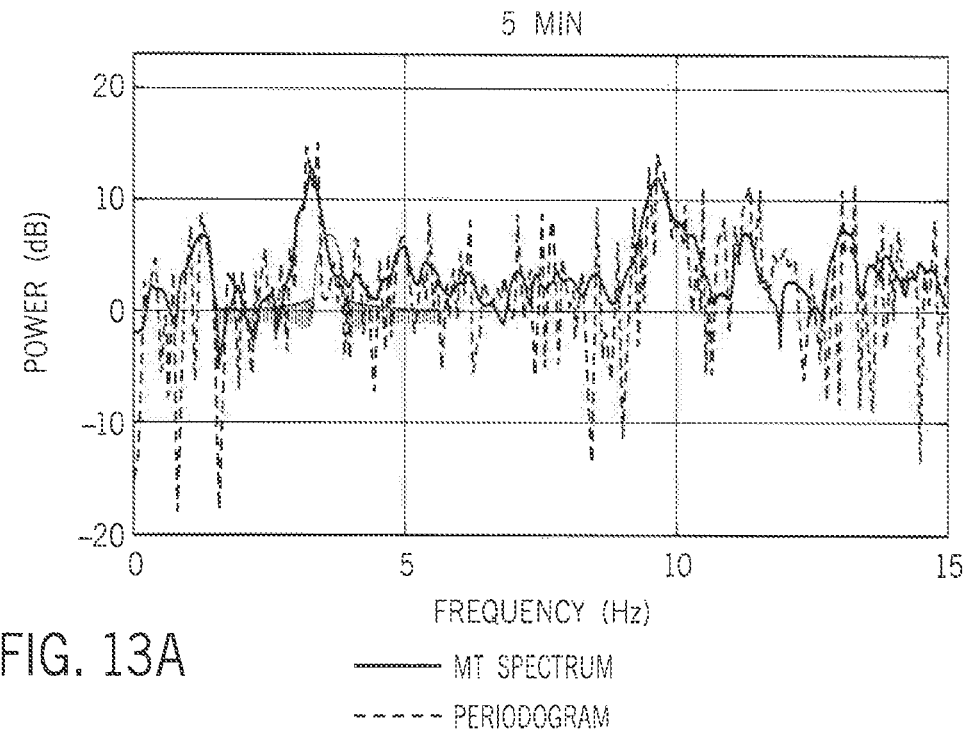
FIG. 13A shows spectrogram Denoising and Spectral Resolution Analysis for a periodogram (red curve) and MT spectrum (black curve) at 5 minutes (FIGS. 4D and 4E) with power spectral density of the first taper (blue curve) centered at 3.5 Hz to analyze leakage at 4 Hz. The MT spectral resolution was set at 0.5 Hz.
Figure 13B:
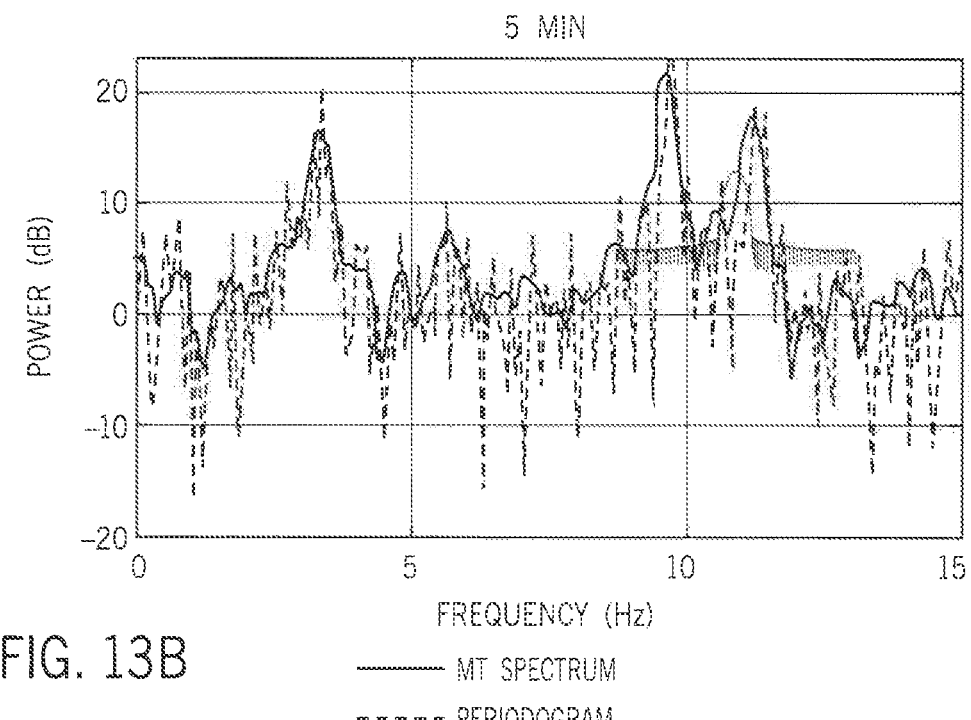
FIG. 13B shows a periodogram (red curve) and MT spectrum (black curve) at 25 minutes (FIGS. 4D and 4E) with power spectral density of the first taper (blue curve) centered at 11 Hz.
Figure 13C:
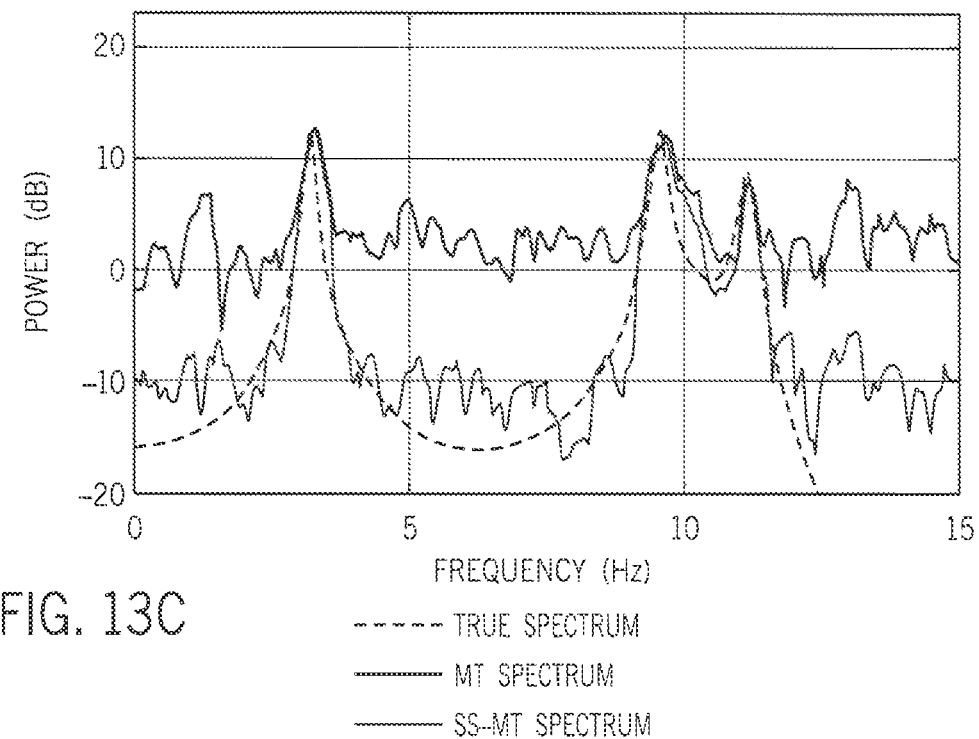
FIG. 13C shows a minute 5 MT spectrum (black curve) from FIG. 4E, SS-MT spectrum (blue curve) from FIG. 4F and true spectrum (red curve) from FIG. 4B.
Figure 13D:
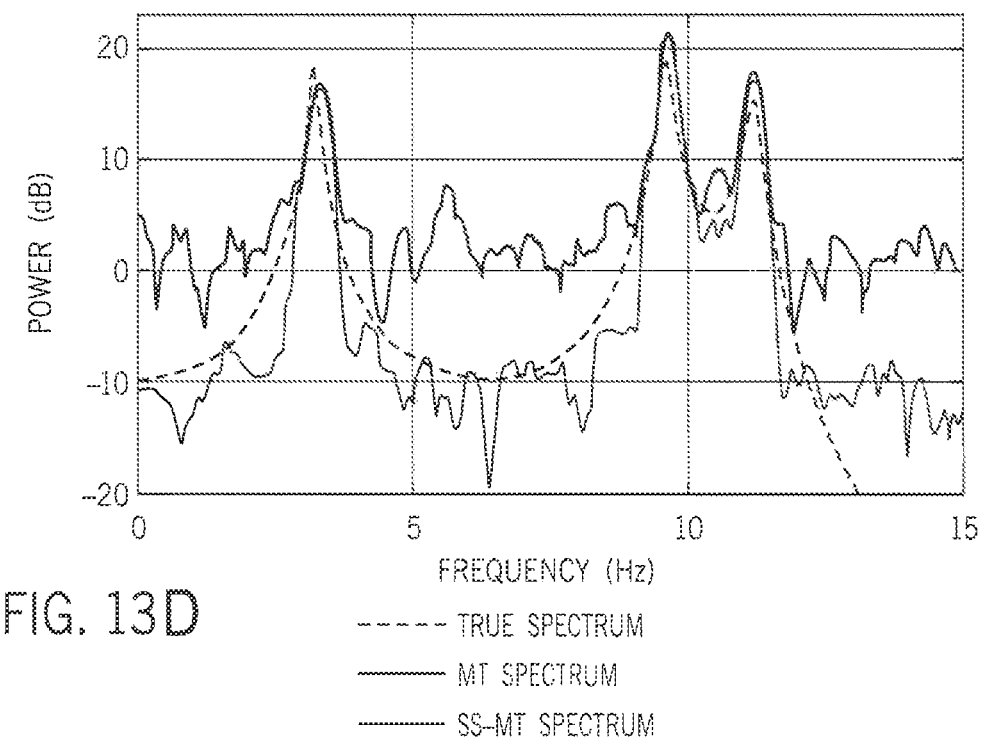
FIG. 13D shows a minute 25 MT spectrum (black curve) from FIG. 4D, SS-MT spectrum (blue curve) from FIG. 4F and true spectrum (red curve) from FIG. 4B.
Figure 15A:
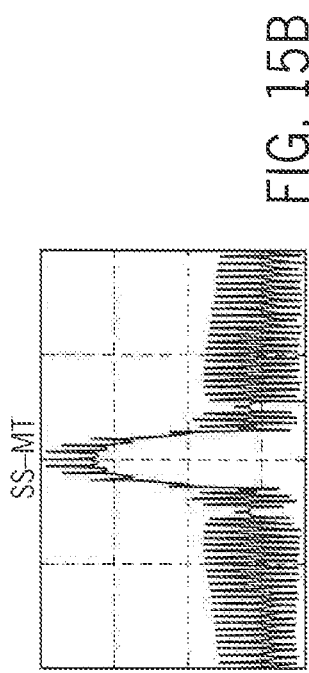
FIG. 15A shows the PSD of the tapers at 25 minutes and at frequency 6 Hz for the MT and the SS-MT spectrograms for the simulated time-series in FIG. 4 for taper 1.
Figure 15B:
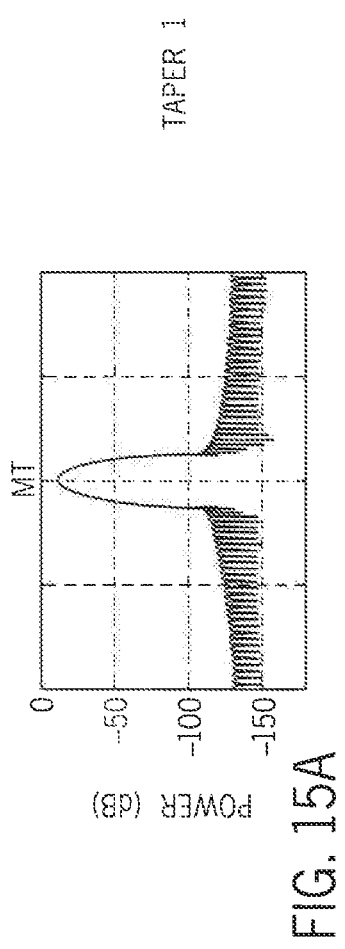
FIG. 15B show the PSD for SS-MT algorithm for taper 1.
Figure 15C:
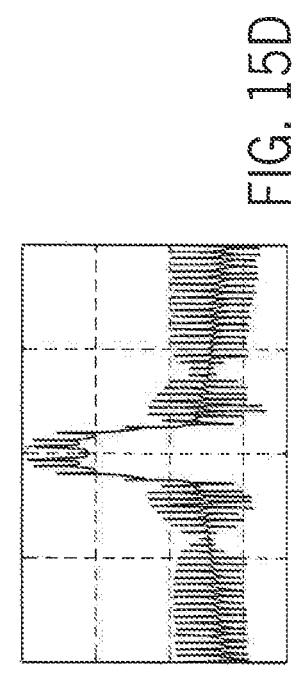
FIG. 15C shows show the PSD for MT method for taper 2.
Figure 15D:
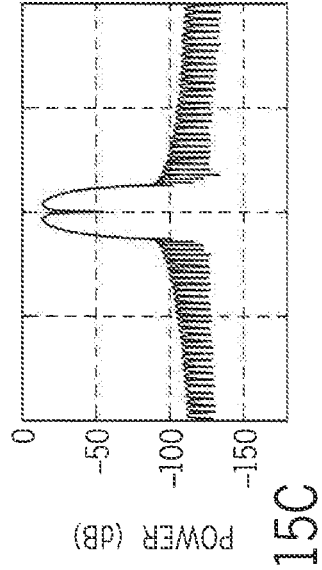
FIG. 15D shows the PSD for SS-MT algorithm for taper 2.
Figure 15E:
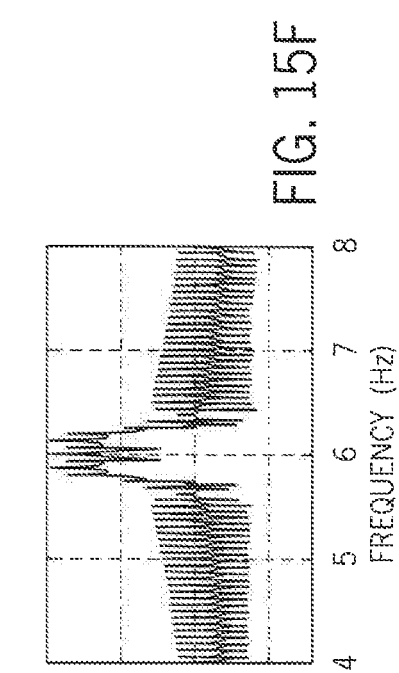
FIG. 15E shows the PSD for MT method for taper 3.
Figure 15F:
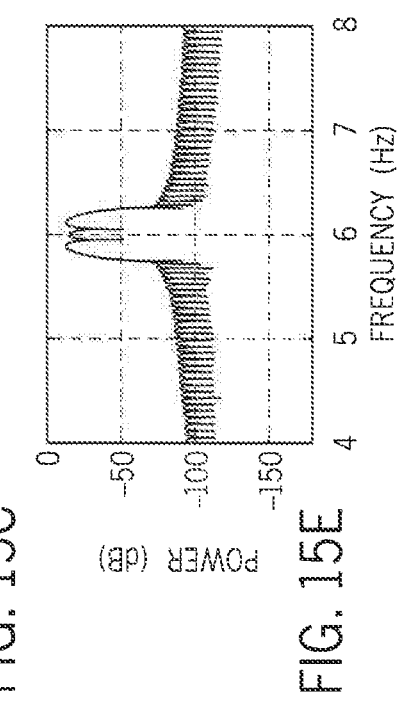
FIG. 15F shows the PSD for SS-MT algorithm for taper 3.
Figure 16A:
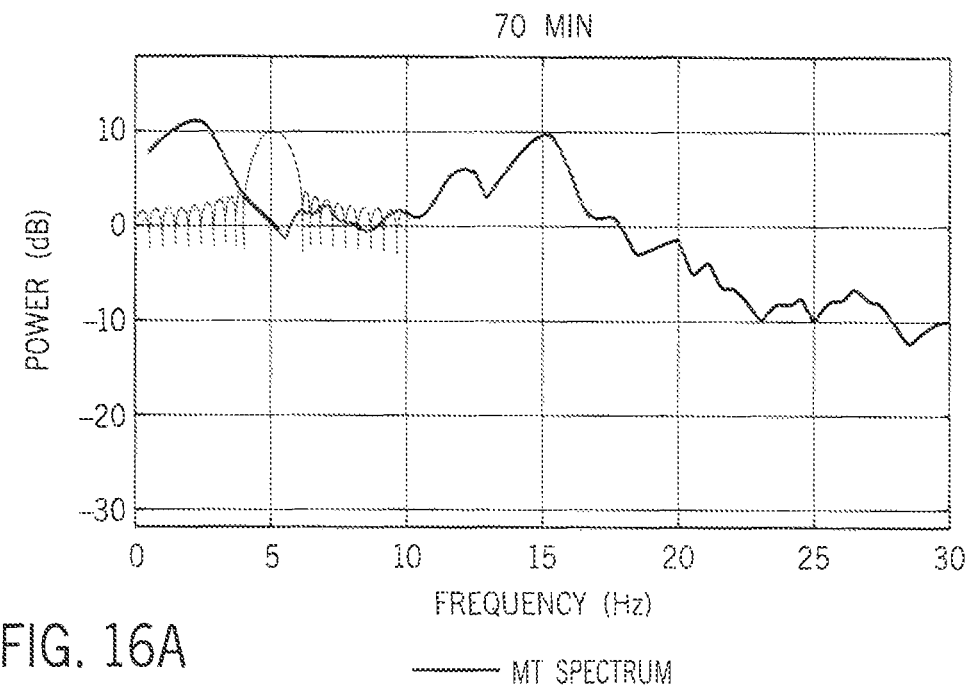
FIG. 16A shows spectrogram Denoising and Spectral Resolution Analysis illustrating MT spectrum (black curve) at 70 minutes (FIG. 5E) with power spectral density of the first taper (blue curve) centered at 5 Hz to analyze leakage at 6 Hz. The spectral resolution was set at 2 Hz.
Figure 16B:
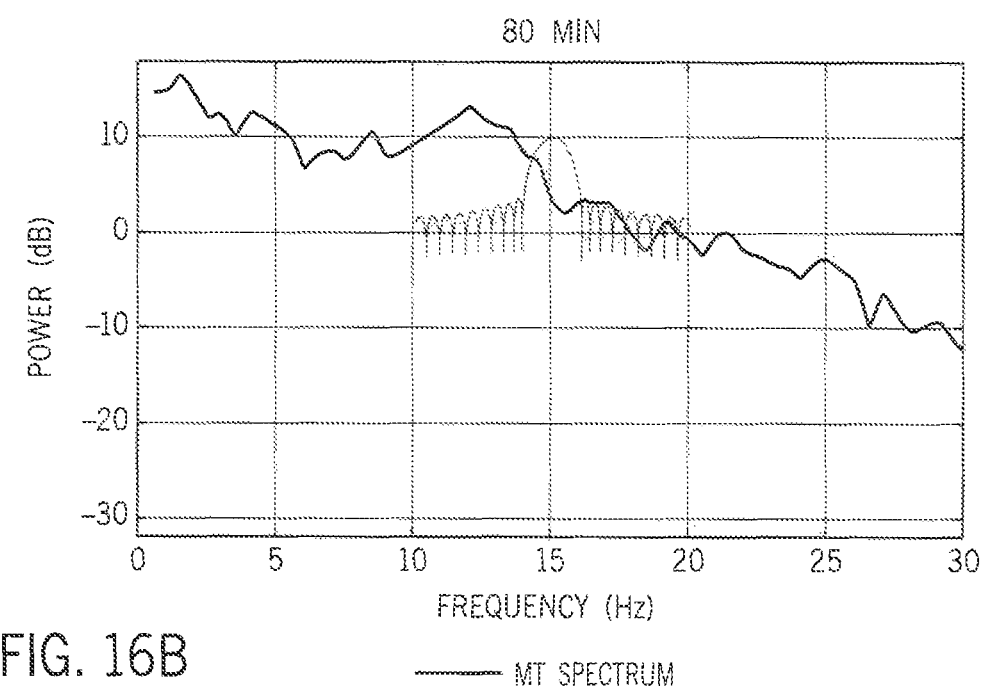
FIG. 16B shows spectrogram Denoising and Spectral Resolution Analysis illustrating MT spectrum (black curve) at 80 minutes (FIG. 5E) with power spectral density of the first taper (blue curve) centered at 15 Hz.
Figure 16C:
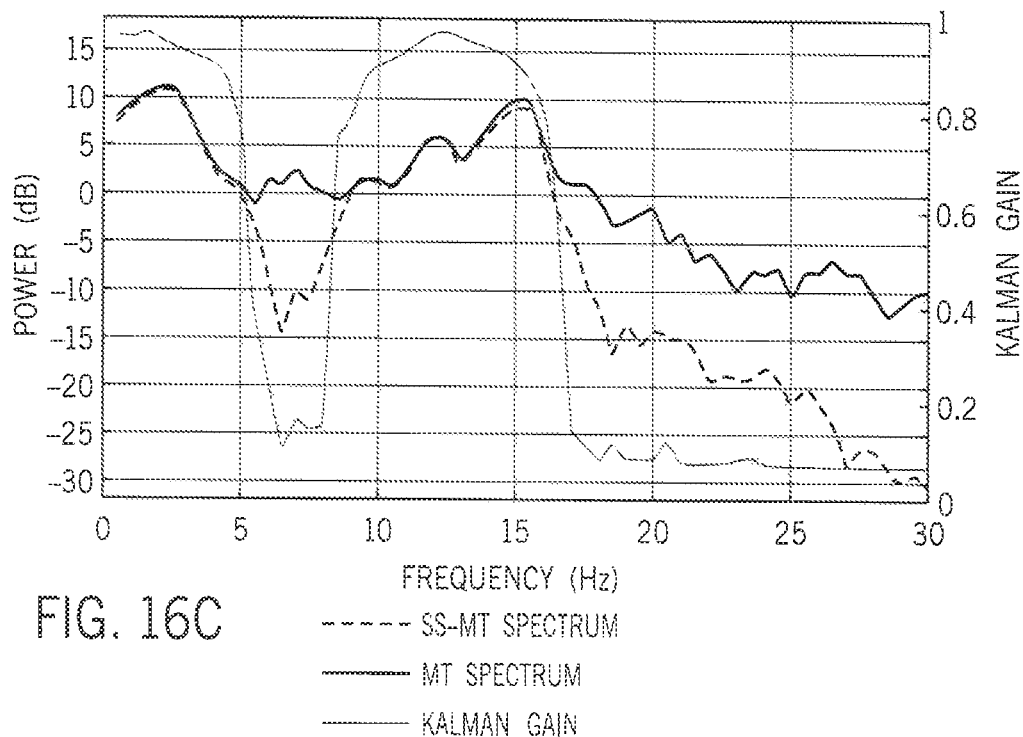
FIG. 16C shows spectrogram Denoising and Spectral Resolution Analysis illustrating a minute 70 MT spectrum (dashed black curve) from FIG. 5E, SS-MT spectrum (red curve) from FIG. 5F and SS-MT steady state Kalman gain for first tapered series (red curve).
Figure 16D:
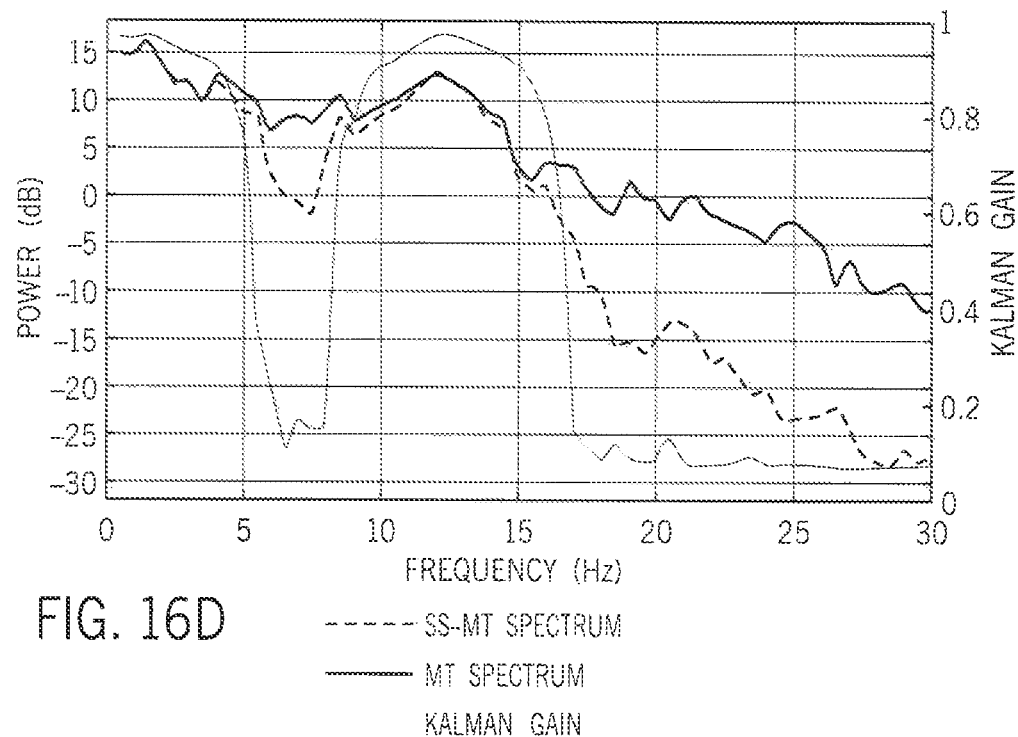
FIG. 16D shows spectrogram Denoising and Spectral Resolution Analysis illustrating a minute 80 MT spectrum (dashed black curve) from FIG. 5E, SS-MT spectrum (red curve) from FIG. 5F and SS-MT steady state Kalman gain for first tapered series (blue curve).

Differential effects demise the SS-MT spectrogram by heightening the contrast between frequencies with high power and those with low power, as illustrated in the analysis of the simulated EEG data (FIG. 4F) and in the analysis of the actual EEG recordings (FIG. 5F). MT eigenspectrograms (FIGS. 9A-9C) have a variability similar to the periodogram (FIG. 5C) that can be reduced by averaging to obtain the MT spectrogram (FIG. 9D, 5D). By contrast, each SS-MT eigenspectrogram (FIGS. 10A-10C) has a variability similar to the SS periodogram (FIG. 5E). By averaging the SS-MT eigenspectrograms, a variability reduction by $M^{-1}$ (Eq. 9) can be achieved at each frequency of the SS-MT spectrogram (FIG. 10D, FIG. 5F), which provides enhanced denoising.

Kalman filter updating (Eqs. 7c and 18) enhances the spectral resolution of the SS-MT spectrogram relative to the MT spectrogram by reducing leakage. To appreciate why, one can assume that $f_k(\omega_j)$ and $f_k(\omega_l)$ are the true spectrograms on time interval k at two frequencies $\omega_j$ and $\omega_l$, and that $f_k(\omega_j) \gg f_k(\omega_l)$. Let $\Delta\omega_r$ be the frequency resolution chosen for the MT analysis. If $|w_j - \omega_l| < \Delta\omega_r$ ($|\omega_j - \omega_l| > \Delta\omega_r$) then, in the m analysis, the narrow (broad) band power at $\omega_j$ leaks into the power at $\omega_l$. The extent of the leakage is governed by the power spectral density of each taper. In the SS-MT analysis, because $\omega_l$ has low power, $\Delta Z_{k|k}^{(m)}(\omega_l)$ weights $\leftarrow Z_{k-1|k-1}^{(m)}(\omega_l)$ much more than $Y_{k,l}^{(m),F}$, the term in Eq. 18 carries the leakage from $\omega_j$. Hence, broad and narrow band power leakage from $\omega_j$ into the power at $\omega_l$ are reduced because the Kalman gain at $\omega_l$ is small.

For example, at 70 minutes (FIG. 5D, 5F), the MT and SS-MT spectrograms generally agree in the high power frequency bands, i.e., 0.1 to 5 Hz and 9.5 to 15.5 Hz, yet disagree in the low power frequency bands, 5.1 to 9.4 Hz and 15.6 to 30 Hz. The 6 Hz frequency lies just on the border of the narrow band leakage from 5 Hz for the MT spectrogram. The 12 dB difference between the MT and the SS-MT spectrograms at 6 Hz results because the former has leakage from the power at 5 Hz, whereas the latter has enhanced denoising and reduced leakage. A 10 to 15 dB power difference persists between the MT and SS-MT spectrograms beyond 15 Hz due to the small values of the Kalman gain in this frequency band.

At 80 minutes (FIGS. 5D and 5F), the MT and SS-MT spectrograms also generally agree in the high power frequency bands, 0.1 to 5 Hz and 10.5 to 15 Hz, yet disagree in the low power frequency bands, i.e. 5.1 to 9.4 Hz and 15.1 to 30 Hz. A similar argument explains the 7 dB difference in power at 16 Hz between the MT and the SS-MT spectrograms at minute 80. The same argument also explains in the analysis of the simulated data example the 7 dB difference in power at 11 Hz in the MT and SS-MT spectrograms at 25 minutes.

As described, the present SS-MT approach estimates increment differences. Therefore, Eq. 13 was used to extract the slow-delta (FIG. 19A), theta (FIG. 19B), alpha (FIG. 19C), and oscillations. In addition, Eq. 14 was used to estimate instantaneous amplitudes (FIG. 19C) for 12 sec of data shown in FIG. 5B beginning at 140 minutes. The magnitudes of the oscillations are consistent with what is observed in the SS-MT spectrograms. The alpha and theta oscillations show substantial slow-delta amplitude modulation consistent with previous reports. A 95% credibility interval for these signals are shown.

In a further example that illustrates the full potential of the SS-MT algorithm introduced herein, EEG data acquired from a human subject receiving intravenous anesthesia was analyzed (FIG. 6). The infusion was administered by computer control at an increasing and then a decreasing rate. In particular, gradually increasing the propofol infusion rate allows the subject to transition gradually from being awake to unconsciousness. On the other hand, gradually decreasing the propofol infusion rate from the rate required to achieve the maximum target effect-site concentration allows the subject to transition from unconsciousness to the awake state.

In analyzing recorded EEG signals, MT spectrograms and SS-MT spectrograms, in accordance with aspects of the present disclosure, were generated, as shown in FIGS. 6C and 6D, respectively. Also, since EEG frequency content can change substantially depending upon the target effect-site concentration, a different set of model parameters was estimated for each anesthetic state using the EM algorithm based on the first 5 minutes of EEG data recorded in each respective state.

Prior to administering propofol, baseline EEG signals was recorded using a frontal lead for approximately 20 minutes while the subject lay supine with eyes closed, After the baseline period, propofol was administered to achieve 5 different increasing level effect-site concentrations (model-derived brain concentrations), as shown in FIG. 6A. Once the 5th level was reached, the infusion rate was systematically reduced, until the infusion was stopped (not shown), to achieve a similar sequence of target effect-site concentrations but in reverse, decreasing order. Each target effect-site concentration was maintained for approximately 14 minutes. Based on the analyses of the subject's responses to yes-no questions administered every 4 seconds, 5 distinct behavioral or anesthetic states were identified, namely a conscious or awake state, a loss of consciousness ("LC") state, an unconscious state, a recovery of consciousness ("RC") state, and again a conscious state, as indicated in FIG. 6A.

The effect of changing the propofol infusion rate are apparent in the unprocessed time-domain EEG signals (FIG. 6B, black curve), the extracted, denoised EEG signals (FIG. 6B, red curve, Eq. 13), and more particularly in the MT spectrogram (FIG. 6C) and SS-MT spectrogram (FIG. 6D). Specifically, moderate-amplitude slow oscillations dominate the EEG at baseline. In increasing the infusion rate, low amplitude, beta-gamma oscillations appear midway through level 2, and transition into narrow-band high-amplitude alpha oscillations by level 4. At the same time, the slow oscillations transition to high-amplitude slow-delta oscillations. By level 5, the alpha oscillations have nearly dissipated and the EEG is dominated by slow-delta oscillations. As the propofol infusion rate is decreased, EEG dynamics are recapitulated in reverse.

As in the previous examples, the SS-MT spectrogram shows substantial spectral denoising and increased resolution when compared to the MT spectrogram. As such, the SS-MT spectrogram, generated in accordance with aspects of the present disclosure, can provide a quantifiably enhanced representation of the different EEG oscillatory components present in different anesthetic states.

To illustrate the ability of the present approach to formal statistical inferences about relationships between different anesthetic states and EEG signatures, the power associated with the different anesthetic states was compared using the SS-MT spectrogram of FIG. 6D. In particular, the average power across frequencies approximately between 0.1 to 30 Hz was computed using representative 100-sec intervals. With reference to FIG. 6A, these representative intervals included a baseline period between 500 to 600 sec (Awake 1), the period between 3,100 to 3,200 sec (LOC), the period between 4,600 to 4,700 sec (UNC), the period between 6,600 to 6,700 sec (ROC), and the period 9,000 to 9,100 sec (Awake 2). To compare two 100-sec intervals for each frequency ω in a given frequency range, the average difference spectrogram between two intervals was computed using:

$$\Delta f \tilde{f}_{r,s}(\omega) = 100^{-1} [\int_s \int_t f^{SS-MT}(\omega) dt - \int_s \int_T f^{SS-MT}(\omega) dt]. \quad (22)$$

where r and s represent two distinct 100-sec intervals. To determine whether there is an appreciable change in the spectrogram properties between any two anesthetic states, a Monte Carlo procedure was used to compute an approximate 95% empirical Bayes' credibility interval for $\Delta \tilde{f}_{r,s}(\omega)$. By using the Kalman filter (Eqs. 7 and 8), the Kalman smoothing (Eq. 15) and the covariance smoothing (Eq. 16) algorithms, the multivariate complex Gaussian joint posterior density $\Delta Z_{k|K}$, for $k=1, \ldots, K$ may be defined, conditional on the parameter estimates. The quantity $\Delta \tilde{f}_{r,s}(\omega)$ is a function of the $\Delta Z_{k|K}$, such that for each random sample of the $\Delta Z_{k|K}$, $\Delta \tilde{f}_{r,s}(\omega)$ may be computed. By drawing a large number of the $\Delta Z_{K|K}$, the associated 95% credibility intervals for $\Delta \tilde{f}_{r,s}(\omega)$ may be computed (FIG. 7).

Figure 7A:
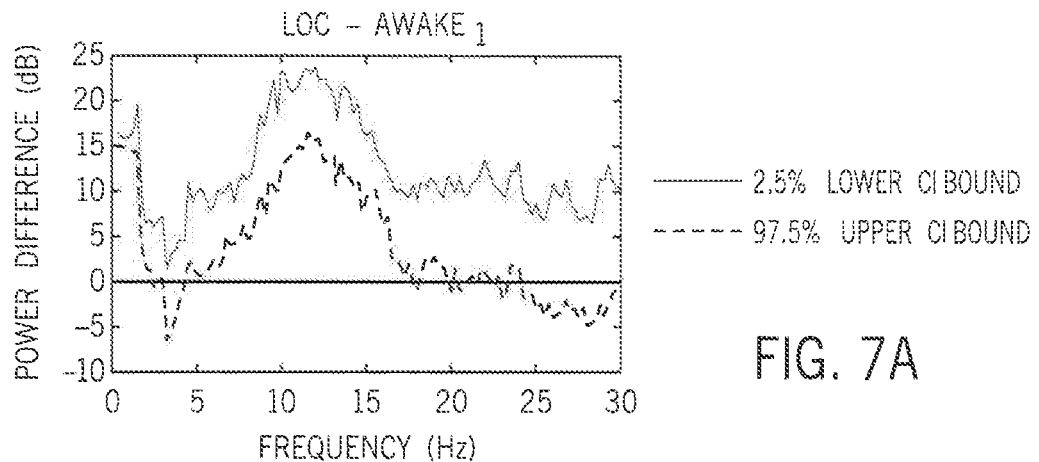
FIG. 7A shows a graph of LOC-Awake1, loss of consciousness compared with baseline awake state for comparison to other graphs comparing the difference in SS-MT spectrogram power between different anesthetic states in FIG. 6A, where each panel shows the average power difference (black line), the upper 97.5% credibility interval (CI) bound (red curve) and the lower 2.5% credibility interval (CI) bound (blue curve).
Figure 7B:
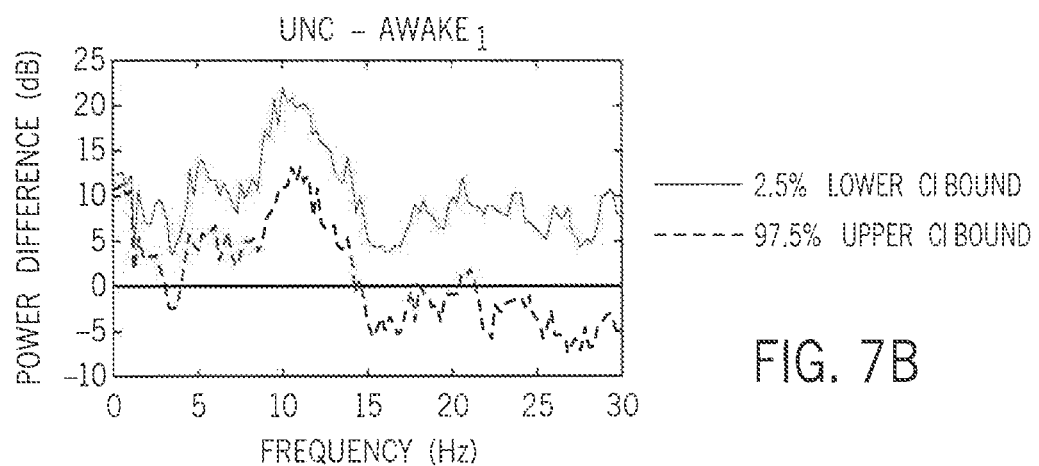
FIG. 7B shows a graph of UNC-Awake1, unconsciousness compared with baseline awake state.
Figure 7C:
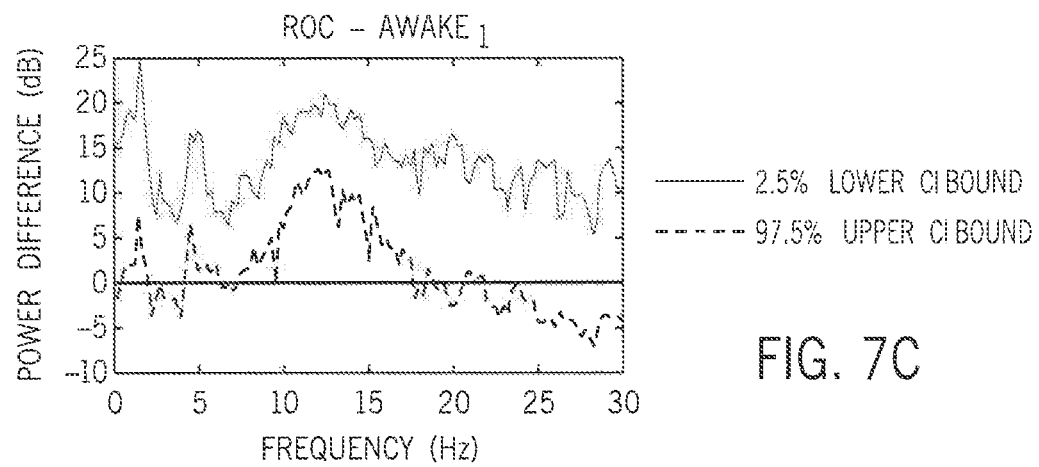
FIG. 7C shows a ROC-Awake1, return of consciousness compared with baseline awake state.
Figure 7D:
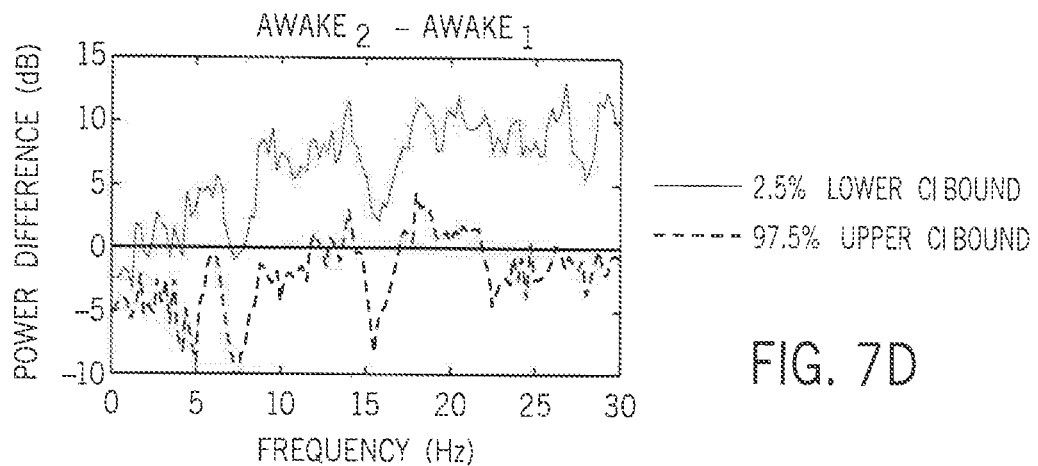
FIG. 7D shows an Awake2-Awake1, final awake state compared with baseline awake state.
Figure 7E:
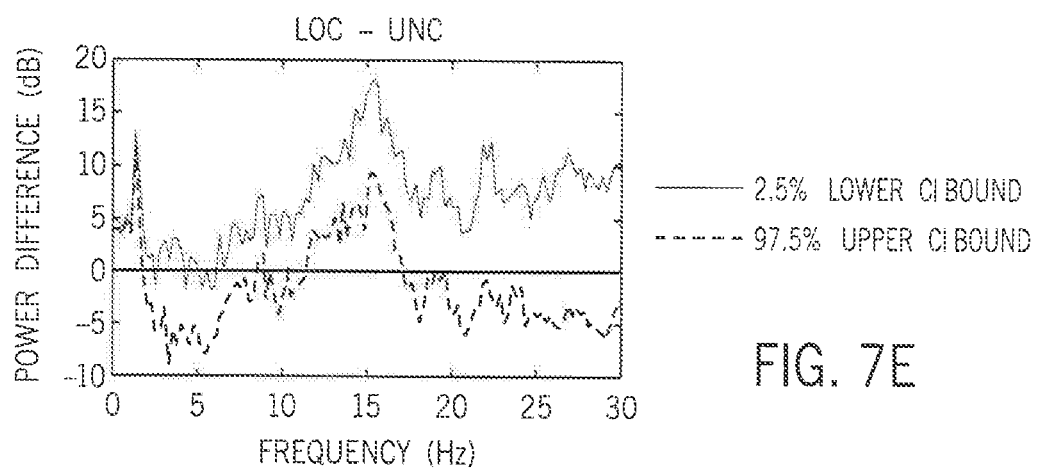
FIG. 7E shows a LOC-UNC, loss of consciousness compared with the unconsciousness state.
Figure 7F:
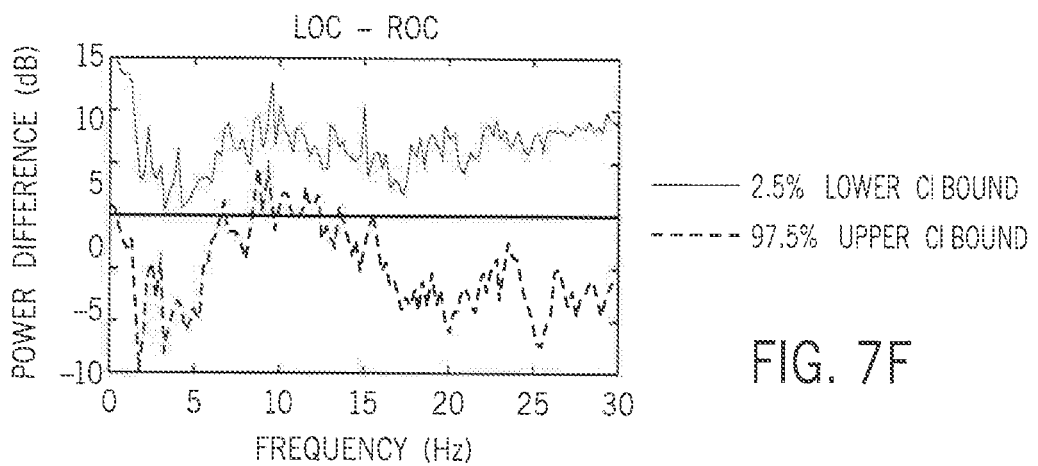
FIG. 7F shows a LOC-ROC, loss of consciousness compared with return of consciousness.

In FIGS. 7A-7F, 6 of the 10 possible comparisons of differences in power among the 5 anesthetic states described with reference to FIG. 6 are shown. In particular, the LOC and UNC states show significant increases in power in the slow-delta and alpha bands relative to the Awake1 state (FIGS. 7A and 7B). There is also a significant increase in power in the upper part of the slow-delta and in the alpha bands between the ROC and Awake1 state (FIG. 7B) and between the LOC and the UNC state (FIG. 7E) In contrast, there are no appreciable differences in power between the Awake1 and Awake1 state (FIG. 7D) or between the LOC and ROC state (FIG. 7F).

As appreciated, these findings are in complete agreement with the structure of the power in the MT-SS spectrogram shown in FIG. 6D. Therefore, it may be concluded that there are significant quantifiable differences in EEG power between different anesthetic states and that those differences can range from 10 to 20 dB (95% credibility interval). These findings also agree with, and extend beyond, the original analyses of these data in which hypothesis testing methods using Bonferroni corrections were used to compare the anesthetized states with just the Awake1 state. Advantageously, inferences obtained as described obviate the need for multiple comparison corrections because they were obtained based on the approximate joint posterior distribution of the power across all of the frequencies and all times in the time series, rather than using tests of multiple null hypothesis. Also, by reporting the results in terms of 95% credibility, the effect size can be directly measured, that is, how much EEG power differs among different anesthetic states. To date, no time-frequency analysis techniques provide an inference framework applicable to the entire series.

As described, in some aspects, a coherence analysis may also performed. Therefore, 16 minutes of EEG data recorded from a patient receiving general anesthesia maintained by an intravenous propofol infusion were analyzed. FIG. 8 shows the MT coherogram (FIG. 8A) and the SS-MT coherogram (FIG. 8B). Both methods showed high coherence (>0.9) between 10 to 15 Hz during this period that is characteristic of general anesthesia maintained by propofol. As appreciated from FIG. 8, the SS-MT coherogram showed greater denoising outside this frequency band compared to the MT coherogram.

The spectral representation of a second-order stationary Gaussian process (Eq. 2) was used to combine the multitaper and the state-space approaches into a computationally efficient, empirical Bayes' paradigm for frequency-domain and time-domain analyses of non-stationary time-series. By the spectral representation theorem, the orthogonal increment differences are the fundamental process that underlie a stationary time-series. Hence, it is reasonable to define non-stationarity in a time-series by modeling the temporal continuity in these fundamental elements.

An important feature of the present framework is the formulation of spectrogram estimation for non-stationary time-series as the problem of estimating the unobservable Gaussian increment differences. This inverse problem was solved by modeling the increment differences as a Gaussian random walk in the frequency domain (Eq. 6), taking the observation model to be the Fourier transform of the tapered time-series (Eq. 5), and then applying a complex Kalman filter algorithm to recursively compute the increment differences (Eqs. 7a-7d). The SS-MT spectrogram (cross-spectrogram) estimates were computed by summing the M eigenspectrograms (eigencross-spectrograms) in Eq. 9 (Eq. 18).

The present solution is computationally efficient because for a given taper, the Fourier transform of the tapered data are J independent, complex Gaussian observations in the frequency domain. Hence, to estimate the increment differences, J independent one-dimensional complex Kalman filters were implemented in parallel. Therefore, given the M tapers, the M·J algorithms run in parallel, a feature which makes the SS-MT spectrogram estimation attractive for real-time applications. Each one-dimensional complex Kalman filter has an associated, Kalman smoother (Eq. 15), covariance smoothing (Eq. 16), and an EM algorithm. The EM algorithm uses all three algorithms to estimate the model parameters from an initial data segment.

Both the state-space and the multitaper components of SS-MT analysis contribute significantly to spectrogram denoising. The state variances and Kalman gains are high (low) at frequencies with high (low) power. Therefore, the Kalman filter updating (Eqs. 7c and 21) denoises the spectrogram by heightening the contrast between high and low power spectrogram ordinates (FIGS. 5D and 5F). The MT component of the SS-MT algorithm further contributes to the denoising by averaging the eigenspectrograms to reduce the spectrogram variance at all frequencies by $M^{-1}$. In addition, state-space estimation (Eqs. 7c and 21) enhances the spectral resolution in the SS-MT spectrogram relative to the MT spectrogram by reducing both narrow band and broad band leakage. Because the Kalman gains at low power frequencies are small, leakage from even nearby frequencies with high power is reduced. In the present simulated and real data examples, the effect of state-space updating on denoising and spectral resolution was a 10 to 15 dB difference between the SS-MT and the MT spectrograms in the low power frequency bands (FIGS. 4D, 4F, 5D, 5F)

By applying the spectral representation theorem to the estimated increment differences (Eqs. 13 and 14), the time-domain signals within specified frequency bands were extracted as well as instantaneous phase and amplitude (FIG. 6). This example is important because time-domain signal extraction is not possible with standard non-parametric spectral methods which only estimate power as a function of frequency. With conventional approaches, estimating instantaneous phase and amplitude requires a second analysis: filtering the data to extract a signal in a particular frequency band followed by applying the Hilbert-Huang transform to the filtered data. The SS-MT paradigm conducts spectral analysis, signal extraction and instantaneous phase and amplitude estimation as parts of a unified framework. Moreover, the SS-MT paradigm is highly flexible because arbitrary combinations of frequencies can be chosen to construct the time-domain signal.

Together the Kalman filter, Kalman smoother and covariance smoothing algorithms provide an empirical Bayes' estimate of the joint distributions of the increment differences conditional on the entire time-series. Therefore, the joint distribution of any time- or frequency-domain function of the increment differences can be computed or simulated and used to make statistical inferences. This aspect of the present paradigm was demonstrated by comparing integrated spectral power in two different time intervals in the isoflurane-ketamine spectrograms (FIG. 7). In contrast, MT methods rely on the jackknife, bootstrap and asymptotic theory to estimate confidence statements for individual frequencies. This is a reasonable approximation to the joint distribution within a stationary interval because the MT spectral estimates are approximately independent. Unlike the SS-MT paradigm, MT spectral analysis does not allow inferences about the spectrogram between different stationary intervals. EMD uses an additive white noise technique to characterize uncertainty in the modes. Justification of this approach has yet to be established.

State-space methods have been applied in non-stationary time-series analysis. If the time-series is modeled as a time-dependent order p autoregressive process (AR(p)), then the order p state model constrains the AR coefficients. Coefficient updates are computed using a p-dimensional Kalman filter or Kalman smoother. After each update, the spectrum is computed using the standard formula for an AR(p) spectrum. The AR(p) model is less flexible than the SS-MT model and care must be taken to insure that each coefficient update produces a stationary process. These models have been used in analyses of speech processing, cardiovascular control, intracranial pressure and sleep states.

One group assumed a time-dependent harmonic regression model and used a time-domain Kalman filter algorithm to update the model coefficients. They analyzed spectra instead of spectrograms, emphasizing spectrum estimation in the presence of missing observations. Recently, spectral pursuit, which is a computationally intensive algorithm to analyze non-stationary time-series by assuming temporal continuity with sparsity in frequency, was introduced by the inventors. Spectral pursuit fits robust stochastic continuity models by iterative Gaussian approximations in a batch analysis, with hyper-parameters estimated by cross-validation.

Herein, the complex Gaussian distribution may be defined as $\varepsilon = \varepsilon_r + i\varepsilon_i$, where the real and imaginary components are independent, zero mean Gaussian random variables with variance $\sigma_\varepsilon^2/2$. The one-dimensional circularly symmetric complex Gaussian distribution is $$p(\varepsilon) = (\pi\sigma_\varepsilon^2)^{-1} \exp\left(-\frac{\varepsilon\varepsilon^*}{\sigma_\varepsilon^2}\right) \triangleq \mathcal{CN}(\varepsilon; 0, \sigma_\varepsilon^2), \qquad (23)$$

where $\varepsilon^* = \varepsilon_r - i\varepsilon_i$ is the complex conjugate of $\varepsilon$.

The derivation of the complex Kalman filter algorithm is now described. Specifically, the parallel, one-dimensional complex Kalman filter algorithms may be derived following the standard maximum a posteriori derivation of the Kalman filter algorithm. To define the recursive estimator of $\Delta Z_k^{(m)}$, Bayes' rule may be used and express the posterior density of $\Delta Z_k^{(m)}$ given all of the data, $Y_{1:k}^{(m),F}$, up through interval k as $$p(\Delta Z_k^{(m)} | Y_{1:k}^{(m),F}) = \frac{p(\Delta Z_k^{(m)} | Y_{1:k-1}^{(m),F}) p(Y_k^{(m),F} | \Delta Z_k)}{p(Y_k^{(m),F} | Y_{1:k-1}^{(m),F})}, \qquad (24)$$

where the first term on the right side of Eq. 2 is the one-step prediction density defined by the Chapman-Kolmogorov equation as $$p(\Delta Z_k^{(m)} | Y_{1:k-1}^{(m),F}) = \int p(\Delta Z_{k-1}^{(m)} | Y_{1:k-1}^{(m),F}) p(\Delta Z_k^{(m)} | \Delta Z_{k-1}^{(m)}) d\Delta Z_{k-1}^{(m)}, \qquad (25)$$

The $\Delta Z_k^{(m)}(\omega_j)$ are independent for $j=1, \ldots, J$ and for each j, $p(\Delta Z_k^{(m)(\omega}{}_j)|Y_{1:k-1,j}^{(m),F})$ is a one-dimensional circularly symmetric complex Gaussian distribution. Hence, given the recursion up through interval k−1 and the state model (Eq. 6), the one-step prediction density has the form $$p(\Delta Z_k^{(m)} \mid Y_{1:k-1}^{(m),F}) = \prod_{j=1}^{J} \mathcal{CN}(\Delta Z_k^{(m)}(\omega_j); \Delta Z_{k|k-1}^{(m)}(\omega_j), \sigma_{k|k-1,j}^{2,(m)}), \quad (26)$$

where $$\Delta Z_{k|k-1}^{(m)}(\omega_j) \triangleq E(\Delta Z_k^{(m)}(\omega_j) \mid Y_{1:k-1,j}^{(m),F}) = \Delta Z_{k-1|k-1}^{(m)}(\omega_j) \quad (27)$$

$$\sigma_{k|k-1,j}^{2,(m)} \triangleq$$
$$E(\|\Delta Z_k^{(m)}(\omega_j) - \Delta Z_{k|k-1}^{(m)}(\omega_j)\|^2 \mid Y_{1:k-1,j}^{(m),F}) = \sigma_{k-1|k-1,j}^{2,(m)} + \sigma_{v,j}^{2,(m)} \quad (28)$$

Moreover, the $Y_{k,j}^{(m),F}$ are also independent for $j=1, \ldots, J$ and for each j, $p(Y_{k,j}^{(m),F}|\Delta Z_k^{(m)}(\omega_j))$ is a one-dimensional circularly symmetric complex Gaussian distribution that is defined by Eq. 5. Hence, the observation model at interval k is $$p(Y_k^{(m),F} \mid \Delta Z_k^{(m)}) = \prod_{j=1}^{J} \mathcal{CN}(Y_{k,j}^{(m),F}; \Delta Z_k^{(m)}(\omega_j), \sigma_\varepsilon^{2,(m)}). \quad (29)$$

The posterior density at interval k is $$p(\Delta Z_k^{(m)}|Y_{1:k}^{(m),F}) \propto p(\Delta Z_k^{(m)}|Y_{1:k-1}^{(m),F})p(Y_k^{(m),F}|\Delta Z_k^{(m)}), \quad (30)$$

and the log posterior density at interval k is $$\log p(\Delta Z_k^{(m)} \mid Y_{1:k}^{(m),F}) = \quad (31)$$
$$-\sum_{j=1}^{J} \frac{\|Y_{k,j}^{(m),F} - \Delta Z_k^{(m)}(\omega_j)\|^2}{\sigma_\varepsilon^{2,(m)}} - \sum_{j=1}^{J} \frac{\|\Delta Z_k^{(m)}(\omega_j) - \Delta Z_{k|k-1}^{(m)}(\omega_j)\|^2}{\sigma_{k|k-1,j}^{2,(m)}}.$$

The J pairs of one-step prediction densities and observation models are independent. Therefore, differentiating Eq. 31 with respect to $\Delta Z_k^{(m)*}(\omega_j)$ gives $$\frac{\partial \log p(\Delta Z_k^{(m)} \mid Y_{1:k}^{(m),F})}{\partial \Delta Z_k^{(m)*}(\omega_j)} = \quad (32)$$
$$\frac{\Delta Z_k^{(m)}(\omega_j) - \Delta Z_{k|k-1}^{(m)}(\omega_j)}{\sigma_{k|k-1,j}^{2,(m)}} - \frac{Y_{k,j}^{(m),F} - \Delta Z_k^{(m)}(\omega_j)}{\sigma_\varepsilon^{2,(m)}},$$

for $j=1, \ldots, J$. Setting Eq. 32 equal to zero yields the recursion of estimate $\Delta Z_{k|k}^{(m)}(\omega_j)$ $$\Delta Z_{k|k}^{(m)}(\omega_j) = \frac{\sigma_\varepsilon^{2,(m)} \Delta Z_{k|k-1}^{(m)}(\omega_j) + \sigma_{k|k-1,j}^{2,(m)} Y_{k,j}^{(m),F}}{\sigma_{k|k-1,j}^{2,(m)} + \sigma_\varepsilon^{2,(m)}}. \quad (33)$$

Setting $\sigma_{k|k,j}^{2,(m)}$ equal to the negative reciprocal of the second derivative of Eq. 31 gives $$\sigma_{k|k,j}^{2,(m)} = ((\sigma_{k|k-1,j}^{2,(m)})^{-1} + (\sigma_\varepsilon^{2,(m)})^{-1})^{-1}. \quad (34)$$

Eq. 7c (Eq. 7d) follows from Eq. 32 (Eq. 33) by applying the definition of the Kalman gain in Eq. 8. Eqs. 27, 28, 33, and 34 are the one-dimensional complex Kalman filter algorithm given in Eqs. 7a-7d.

An example EM algorithm for model parameters and initial state estimation is described below. In particular, an EM algorithm may be used to find the maximum-likelihood estimates of $\Theta = \{\sigma_\varepsilon^{2,(m)}, \sigma_{v,j}^{2,(m)}, \Delta Z_0^{(m)}\}$. The maximum-likelihood estimates may be computed by maximizing the expectation of completed data log-likelihood. The join probability distribution of $\Delta Z_{1:k}^{(m)}(\omega_j)$ and $Y_{1:K,j}^{(m),F}$ at frequency j can be written as:

$$L_j^{(m)} = p(\Delta Z_0^{(m)}(\omega_j) \mid \sigma_{v,j}^{2,(m)}) \times \prod_{k=1}^{K} p(\Delta Z_k^{(m)}(\omega_j) \mid \Delta Z_{k-1}^{(m)}(\omega_j), \sigma_{v,j}^{2,(m)}) \times \quad (35)$$
$$\prod_{k=1}^{K} p(Y_{k,j}^{(m),F} \mid \Delta Z_k^{(m)}(\omega_j), \sigma_\varepsilon^{2,(m)}),$$

where the probability density of the initial state may be assumed to be given by $$p(\Delta Z_0^{(m)}(\omega_j)) = (\pi \sigma_{v,j}^{2,(m)})^{-1} \exp\left(-\frac{\|\Delta Z_0^{(m)}(\omega_j)\|^2}{\sigma_{v,j}^{2,(m)}}\right). \quad (36)$$

In iterating l of the E-step, the algorithm may compute the expectation of the complete data log-likelihood, given the observed data and the previous estimates of the parameters from the previous iteration l−1. For simplicity, the superscript m may be omitted for the tapered data series. Taking the log and expectation to the likelihood yields:

$$E[\log L_j^{(l)} \mid Y_{1:K,j}^F, \Theta^{(l-1)}] = \quad (37)$$
$$E\left[-\frac{\|\Delta Z_0^{(l)}(\omega_j)\|^2}{\sigma_{v,j}^{2,(l-1)}} - \frac{1}{\sigma_\varepsilon^{2,(l-1)}} \sum_{k=1}^{K} \|Y_{k,j}^{F,(l)} - \Delta Z_k^{(l)}(\omega_j)\|^2 - \right.$$
$$K \log(\pi \sigma_\varepsilon^{2,(l-1)}) - (K+1)\log(\pi \sigma_{v,j}^{2,(l-1)}) -$$
$$\left. \frac{1}{\sigma_{v,j}^{2,(l-1)}} \sum_{k=1}^{K} \|\Delta Z_k^{(l)}(\omega_j) - \Delta Z_{k-1}^{(l)}(\omega_j)\|^2 \mid Y_{1:K,j}^F \right].$$

To evaluate Eq. 37, three quantities need to be computed for $k=1, \ldots, K$. These are:

$$\Delta Z_{k|K}^{(l)}(\omega j) = E[\Delta Z_k(\omega j)|Y_{1:K,j}^F, \Theta^{(l-1)}],$$

$$W_{k|K,j}^{(l)} = E[\|\Delta Z_k(\omega j)\|^2 | Y_{1:K,j}^F, \Theta^{(l-1)}],$$

$$W_{k,k-1|K,j}^{(l)} = E[\Delta Z_k(\omega j) \Delta Z_{k-1}^*(\omega j) | Y_{1:K,j}^F, \Theta^{(l-1)}]. \quad (38)$$

Quantities in Eq. 38 may be efficiently computed using a Kalman filter, Kalman smoothing, and covariance smoothing algorithms.

To carry out the M-step, one may let $\tau_{v,j}^{(l)}=1/\sigma_{v,j}^{2,(l)}$ and $\tau_{\varepsilon}^{(l)}=1/\sigma_{\varepsilon}^{2,(l)}$. In addition, it may be used that each has a gamma prior density defined as $$p(\tau \mid \alpha, \beta) = \frac{\beta^{\alpha}}{\Gamma(\alpha)}(\tau)^{\alpha-1}\exp(-\beta\tau), \quad (39)$$

for $\alpha>1$ and $\beta>0$. The expectation of log join posterior density of $\tau_{v,j}^{(l)}$ and $\tau_{g}^{(l)}$ may be defined as $$E[\log p(\tau_{\varepsilon}^{(l)},\tau_{v,j}^{(l)}|Y_{1:K,j}^{F},\Theta^{l-1}]$$

$$\propto \log(p(\tau_{\varepsilon}^{(l)}|\alpha,\beta))+\log(p(\tau_{v,j}^{(l)}|\alpha,\beta))+E[\log L_{j}^{(l)}], \quad (40)$$

Eq. 40 may be maximized with respect to $\tau_{v,j}^{(l)}$ and $\tau_{\varepsilon}^{(l)}$ to obtain $$\tau_{v,j}^{(l)} = \frac{K + \alpha}{2\sum_{k=1}^{K}\left(W_{k-1|K,j}^{(l)} - \Re\{W_{k,k-1|K,j}^{(l)}\}\right) + W_{K|K,j}^{(l)} + \beta}, \quad (41)$$

$$\tau_{\varepsilon}^{(l)} = \frac{\alpha - 1 + JK}{\left(\left(Y_{k,j}^{P,(l)}\right)^{2} + W_{k|K,j}^{(l)} - 2\Re\{Y_{k,j}^{F,(l)*}\Delta Z_{k|K,j}^{(l)}\}\right) + \beta}.$$

respectively. The initial state $\Delta Z_0(\omega_j)$ can be estimated using the Fourier transform of the original time series $X_1$ as $\Delta Z_0(\omega_j)$=$FX_1$. The EM algorithm may iterate between E-steps and M-steps until $\|\Delta Z_{k|K}^{(l)}-\Delta Z_{k|K}^{(l-1)}\|^2/\|\Delta Z_{k|K}^{(l-1)}\|^2<\varepsilon$ where $\varepsilon\in(0, 0.001)$ or $l=L_{max}$, where $L_{max}$ may be a pre-specified number of maximum iterations.

Figure 20:
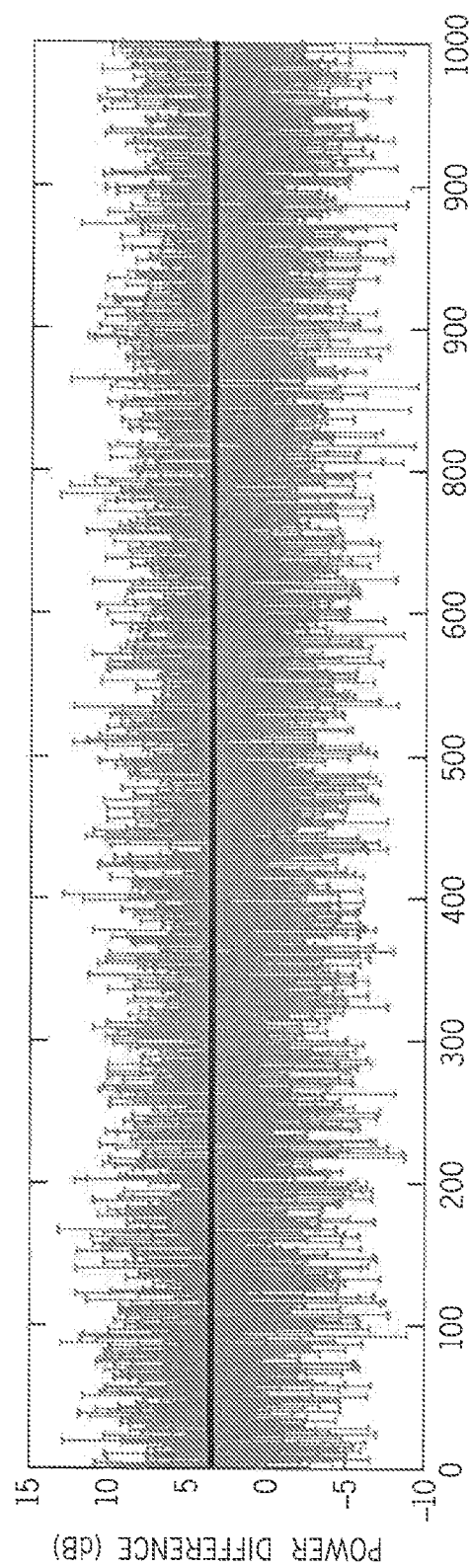
FIG. 20 shows results from a simulation analysis of the coverage probability for the empirical Bayes 95% confidence intervals.

To assess the accuracy of the empirical Bayes 95% confidence intervals, a simulation analysis was conducted using the non-stationary AR(6) process in Eq. 20. Results are shown in FIG. 20. Specifically, the actual difference in spectral power at 11.5 Hz between times 27 and 15 minutes was computed. One thousand time-series from Eq. 20 were simulated and each fit using the SS-MT model and EM algorithm. A Monte Carlo algorithm was used to compute from each SS-MT fit the 95% confidence interval for the spectral power difference by making 3,000 draws from the empirical Bayes posterior distribution $f(\Delta Z|Y, \hat{\Sigma})$, where $\hat{\Sigma}$ denotes the maximum likelihood estimates of the noise floor variance and the state variances at each frequency. The black horizontal line in FIG. 20 at about 4 dB represents the true difference in spectral power at 11.5 Hz between times 27 and 15 minutes. The red vertical lines in FIG. 20 represent the empirical Bayes 95% confidence intervals computed from the simulations. Analysis revealed the actual frequentist coverage probability to be about 0.966. The lower and upper bounds of the Monte Carlo error based on 1000 draws from a binomial distribution with p=0.95 was [0.947, 0.964]. The fact that the actual coverage probability was just beyond the upper Monte Carlo error bound suggests that the SS-MT 95% confidence interval may be slightly conservative. This observation is reassuring given that the SS-MT model lies outside the model class that generated the data.

Using the AR (6) model in Eq. 20, the effect of stationary interval choice on spectrogram estimation was analyzed. For this model, no ground truth interval was selected because there is no finite interval on which data are stationary. Moreover, the SS-MT model is outside the model class generating the data. In FIG. 4F, the number of data points per stationary interval was selected to be J=1.024. In this analysis, the SS-MT model was also fit using J=512 (8 seconds), J=1,024 (16 seconds), J=2,048 (32 seconds), and J=4,096 (64 seconds). The table below shows the mean-squared error for seven frequencies computed by averaging the sum of squared differences between each estimate (periodogram, MT, SS-periodogram, and SS-MT) and the true spectrogram over all time intervals for the four difference choices of stationary interval lengths.

| Mean-Squared Error as a Function of Stationary Interval Length | | | | |
|---|---|---|---|---|
| Frequency (Hz) | Periodogram | MT | SS-P | SS-MT |
| J = 512 (8 seconds) | | | | |
| 1.5 | 7 | 7 | −17 | −18 |
| 3.5 | 34 | 29 | 33 | 28 |
| 6.5 | 8 | 7 | −15 | −18 |
| 9.5 | 34 | 34 | 34 | 33 |
| 10.5 | 17 | 12 | 13 | 5 |
| 11.5 | 31 | 28 | 30 | 25 |
| 12.5 | 8 | 8 | −15 | −20 |
| J = 1,024 (16 seconds) | | | | |
| 1.5 | 7 | 5 | −16 | −22 |
| 3.5 | 35 | 27 | 34 | 27 |
| 6.5 | 8 | 5 | −15 | −21 |
| 9.5 | 34 | 30 | 33 | 29 |
| 10.5 | 16 | 11 | 10 | 5 |
| 11.5 | 32 | 23 | 32 | 23 |
| 12.5 | 8 | 5 | −17 | −19 |
| J = 2,048 (32 seconds) | | | | |
| 1.5 | 7 | 5 | −16 | −22 |
| 3.5 | 35 | 25 | 35 | 25 |
| 6.5 | 8 | 5 | −13 | −18 |
| 9.5 | 33 | 29 | 33 | 29 |
| 10.5 | 16 | 10 | 8 | 2 |
| 11.5 | 34 | 19 | 34 | 19 |
| 12.5 | 6 | 5 | −16 | −18 |
| J = 4,096 (64 seconds) | | | | |
| 1.5 | 7 | 5 | −19 | −21 |
| 3.5 | 33 | 26 | 33 | 28 |
| 6.5 | 7 | 4 | −11 | −18 |
| 9.5 | 34 | 28 | 33 | 28 |
| 10.5 | 17 | 10 | 8 | −1 |
| 11.5 | 38 | 17 | 38 | 17 |
| 12.5 | 6 | 4 | −13 | −17 |

The MT and SS-MT spectrograms were estimated using 2 tapers (J = 512), 4 tapers (J = 1,024), 8 tapers (J = 2,048), and 10 tapers (J = 4,096) to keep spectral resolution at 0.5 Hz. Table entries are in decibels, i.e., $10\log_{10}(\text{MSE})$.
MT: multitaper spectrogram;
SS-P: state-space periodogram;
SS-MT: state-space multitaper spectrogram.

Within the SS-MT estimates, the stationary interval length that minimized the MSE differed in relation to the magnitude of the spectral power at a given frequency. For two of the frequencies with high power (9.5 Hz and 11.5 Hz), and the frequency with intermediate power (10 Hz), the MSE was minimized by choosing a 64-second stationary interval. The MSE for the third highest frequency With high power (3.5 Hz) was minimized by a 32-second stationary interval choice. The spectrogram estimates for the high-power frequencies using the 64-second stationary interval resembled most closely the true spectrogram. For the three frequencies with low power (1.5 Hz, 6.5 Hz and 12.5 Hz), the minimum MSE stationary interval choice was the 16-second interval. Although the 16-second stationary interval spectrogram estimate had the smallest MSEs for the low-power frequencies, the difference between it and the other spectrograms at these frequencies were not appreciable discernible.

In summary, the present disclosure introduces a new paradigm that provides a computationally efficient framework for spectrogram estimation, time-domain signal extraction and statistical inference for non-stationary time-series, and offers a number of advantages, as described below.

First, the SS-MT approach described significantly reduces background noise. This may be appreciated by comparing the simulated example in FIG. 5D (MT) and 2F (SS-MT) and the real EEG example in FIGS. 6D (MT) and 6F (SS-MT). There is a 10-15 dB decrease in background noise. This difference is substantial.

Second, the SS-MT approach described has enhanced spectral resolution beyond that which is achievable by MT alone. The key idea here is that MT is optimal in enhancing resolution for a fixed interval. SS-MT takes that estimate and improves upon it by reducing the leakage either further by using the information from the previous estimate. For example, in the MT estimate in FIG. 5D, there is substantial leakage of power from 16 Hz to 17 Hz. This does not happen in the SS-MT estimate in FIG. 5F because the Kalman filter estimate of the spectrum at 17 Hz uses more information from the previous estimate than it does from the new estimate, and as a consequence, the leakage that would come if the new estimate alone were used is reduced.

Third, the spectral components are more easily identified because of the substantial denoising and enhanced resolution (FIG. 5). This is key for anesthetic state monitoring and control. Also, time-domain signals can be extracted in any frequency band with SS-MT (FIG. 6). This is not possible at all with traditional MT. In particular, traditional MT estimates only the spectrum on an interval. SS-MT estimates the complex-valued Gaussian increments that make up the spectrum on an interval. In fact, one can reconstruct any signal within any frequency band desired from the data: high-pass, band pass, low pass or arbitrary combinations of any desired frequencies. To do this, currently the standard practice uses a filtering technique combined with a Hilbert-Huang transform. That is, another technique must be utilized. By contrast, filtering comes straight out of the present method. The filtering and Hilbert-Huang transform cannot select an arbitrary set of frequencies. SS-MT can compute in addition, both instantaneous phase and amplitude information at all times (Eq. 14). To do this currently the standard practice is to use a filtering technique. These types of signal extractions call be performed with the SS-MT algorithm and are key for monitoring and control of anesthetic state.

Fourth, the SS-MT approach described has is highly efficient. For any taper the computation is a J-dimensional Kalman filter where J could be 500, such as in the real data examples in the paper. Herein, this computation is carried out not with a J-dimensional Kalman filter, but rather with J one-dimensional, independent Kalman filters run in parallel. This is because the geometry of the problem is exploited and carried out in all of the computations in the frequency domain where the increments differences at different frequencies are (independent) orthogonal. The computations are substantially fast, making real-time implementation very straight forward.

Finally, the present SS-MT framework allows formal statistical comparisons between arbitrary points in the data. This is not possible for current spectral methods because estimates on different data segments are assumed to be unrelated. This is an important advance for comparing the properties of the spectrogram (anesthetic state) at one point with the spectrogram (anesthetic state) at another and being able to say precisely how much the spectrograms (anesthetic states) differ.

It is important to appreciate that the state-space analysis alone (modeling the relationship between the intervals) would not give the improvements described herein. This may be appreciated by comparing FIG. 5E (State-space alone) with FIG. 5F (SS-MT). Averaging across eigenspectrograms produces denoising that the state-space alone cannot give. The variance of the noise decreases by 1 over the number of tapers due to eigenspectogram averaging. Hence, the combination of SS and MT represents an important, and non-obvious step that provides the present SS-MT approach its unique advantages. In other words, for the first time, spectrogram estimation, along with spectral characterization, has been explicitly achieved across entire time-series data sets. By contrast, up to now, all investigations using traditional MT methods have only considered spectrum estimation within an interval.

The presently described SS-MT paradigm facilitates several new lines of investigation. The state variances are the key algorithm parameters because a different state variance independently controls stochastic continuity at each frequency. Alternatives to EM estimates such as the method-of-moments and adaptive estimates should be studied. Adaptive parameters estimation is important when power at a frequency abruptly changes by several decibels. Subject matter constraints may be used to reduce the number of parameters. In the real data examples, state variance estimation was limited to frequencies below 30 Hz based on knowledge of the frequency range relevant to tracking anesthetic states. The SS-MT paradigm may be extended by using higher-order state models and/or observation noise models. Finally, the SS-MT theoretical framework may connect more closely with non-stationary time-series and multitaper spectral estimation theory.

There are several important commercial applications that are envisioned including monitoring reliably and accurately the brain states of patients receiving general anesthesia and sedation. In particular, the SS-MT approach described would allow build a far more principled approach to anesthetic state monitoring and control systems than use traditional MT. SS-MT is a substantial non-obvious technological advance that helps both scientific understand and product design. It will give a clearer picture of the individual anesthetic signatures and the anesthetics signatures for patients as a function age. All of this greatly facilitates clearer, cleaner monitoring and anesthetic state control design strategies.

The present invention has been described in terms of one or more preferred embodiments, and it should be appreciated that many equivalents, alternatives, variations, and modifications, aside from those expressly stated, are possible and within the scope of the invention.

The invention claimed is:

1. A system for analyzing electrophysiological signals acquired from a subject, the system comprising:
   an input configured to receive electrophysiological signals acquired from a subject; and
   at least one processor, in communication with the input, configured to:
      assemble a set of time-series data using the electrophysiological signals received by the input;
      analyze the set of time-series data across a series of intervals dividing the time-series of data using a state-space multi-taper framework to generate spectral information describing the electrophysiological signals using information from more than a single interval dividing the time-series of data;
      generate a report including the spectral information extending in time with the time-series of data; and
   an output configured to provide the report.

2. The system of claim 1, wherein the system further comprises a sensor assembly in communication with the input that is configured to acquire the electrophysiological signals.

3. The system of claim 2, wherein the sensor assembly is configured to acquire at least one of electroencephalogram ("EEG") signals, electromyography ("EMG") signals, electrocorticography ("ECoG") signals, local field potentials ("LFP") signals, electrocardiography ("ECG") signals, electrooculography ("EOG") signals, galvanic skin response ("GSR") signals, oxygen saturation ("SAO$_2$") signals, and ocular microtremor ("OMT") signals.

4. The system of claim 1, wherein the at least one processor is further configured to generate a time-frequency representation using the spectral information.

5. The system of claim 1, wherein the at least one processor is further configured to apply a Kalman filter in analyzing the set of time-series data.

6. The system of claim 1, wherein the at least one processor is further configured to apply an expectation maximization ("EM") algorithm in analyzing the set of time-series data.

7. The system of claim 1, wherein the at least one processor is further configured to determine a depth of anesthesia, a level of sedation, or a change thereof, using the spectral information.

8. The system of claim 1, wherein the at least one processor is further configured to determine a sleep state of the subject using the spectral information.

9. The system of claim 1, wherein the at least one processor is further configured to identify and provide, based on the brain state determined, feedback for controlling the subject to reach a predetermined brain state.

10. The system of claim 1, wherein the at least one processor is further configured to apply a weighting when generating the spectral information that at least one of disfavors increases or fluctuations in low power or noise frequencies relative to at least one preceding interval or favors frequencies with high power relative to at least one preceding interval.

11. A method for analyzing electrophysiological signals acquired from a subject, the method comprising:
receiving electrophysiological signals acquired from a subject using one or more sensors;
assembling a set of non-stationary time-series data using the acquired electrophysiological signals;
analyzing the set of time-series data across a plurality of stationary intervals using a state-space multi-taper framework to generate spectral information describing the electrophysiological signals;
and
generating a report including the spectral information extending with the non-stationary, time-series data.

12. The method of claim 11, wherein the method further comprises acquiring at least one of electroencephalogram ("EEG") signals, electromyography ("EMG") signals, electrocorticography ("ECoG") signals, local field potentials ("LFP") signals, electrocardiography ("ECG") signals, electrooculography ("EOG") signals, galvanic skin response ("GSR") signals, oxygen saturation ("SAO$_2$") signals, and ocular microtremor ("OMT") signals.

13. The method of claim 11, wherein the method further comprises generating a time-frequency representation using the determined spectral information.

14. The method of claim 11, wherein the method further comprises applying a Kalman filter in analyzing the set of time-series data.

15. The method of claim 11, wherein the method further comprises applying an expectation maximization ("EM") algorithm in analyzing the set of time-series data.

16. The method of claim 11, wherein the method further comprises determining a depth of anesthesia, a level of sedation, or a change thereof.

17. The method of claim 11, wherein the method further comprises determining a sleep state of the subject using the spectral information.

18. The method of claim 11, wherein the method further comprises controlling the subject based on the determined brain state.

19. The method of claim 11, wherein the method further comprises identifying and providing, based on the brain state determined, feedback for controlling the subject to reach a predetermined brain state.

20. The method of claim 11, further comprising apply a weighting when generating the spectral information that at least one of disfavors increases or fluctuations in low power or noise frequencies relative to at least one preceding of the plurality of stationary intervals or favors frequencies with high power relative to at least one preceding of the plurality of stationary intervals.

* * * * *

UNITED STATES PATENT AND TRADEMARK OFFICE
CERTIFICATE OF CORRECTION

PATENT NO. : 10,786,168 B2
APPLICATION NO. : 15/826182
DATED : September 29, 2020
INVENTOR(S) : Emery N. Brown et al.

It is certified that error appears in the above-identified patent and that said Letters Patent is hereby corrected as shown below:

In the Specification

Column 3, Line 7, "points, in principle," should be --points. In principle,--.

Column 4, Line 52, "and 5." should be --and 5B.--.

Column 4, Line 57, "multi taper" should be --multitaper--.

Column 6, Line 49, "taper" should be --taper 2--.

Column 14, Line 8, "$\|Y_{k,j}^{(m),F}\|^2$" should be -- $\|Y_{k,j}^{(m),F}\|^2$ --.

Column 14, Eq (4), "$Y_k^F = \Delta Z_k + \varepsilon_k^F$" should be -- $Y_k^F = \Delta Z_k + \varepsilon_k^F$ --.

Column 14, Line 17, "$Y_k^F = FY_k$" should be -- $Y_k^F = FY_k$ --.

Column 14, Line 17, "$\varepsilon_k^F = F\varepsilon_k$" should be -- $\varepsilon_k^F = F\varepsilon_k$ --.

Column 14, Line 18, "$I(\sigma_\varepsilon^2)$" should be -- $I(\sigma_\varepsilon^2)$ --.

Column 14, Line 21, "$Y_k^F$" should be -- $Y_k^F$ --.

Column 14, Eq. (5)," $Y_k^{(m),F} = \Delta Z_k^{(m)} + \varepsilon_k^{(m),F}$" should be -- $Y_k^{(m),F} = \Delta Z_k^{(m)} + \varepsilon_k^{(m),F}$ --.

Column 14, Line 27, "$\Delta Z_k^{(m)}$" should be -- $\Delta Z_k^{(m)}$ --.

Signed and Sealed this
Twenty-ninth Day of December, 2020

Andrei Iancu
*Director of the United States Patent and Trademark Office*

CERTIFICATE OF CORRECTION (continued)

U.S. Pat. No. 10,786,168 B2

Column 14, Line 27, "$\varepsilon_k^{(m),F}$" should be -- $\varepsilon_k^{(m),F}$ --.

Column 14, Line 28, "$\varepsilon_k^F$" should be -- $\varepsilon_k^F$ --.

Column 14, Eq. (6), "$\Delta Z_k^{(m)} = \Delta Z_{k-1}^{(m)} + v_k^{(m)}$" should be -- $\Delta Z_k^{(m)} = \Delta Z_{k-1}^{(m)} + v_k^{(m)}$ --.

Column 14, Line 40, "$v_k^{(m)}$" should be -- $v_k^{(m)}$ --.

Column 14, Line 42, "$l(\sigma_{v,j}^{2,(m)})$" should be -- $I(\sigma_{v,j}^{2,(m)})$ --.

Column 14, Line 51, "$\Delta Z_k^{(m)}$" should be -- $\Delta Z_k^{(m)}$ --.

Column 14, Line 53, "$\Delta Z_k^{(m)}(\omega_j)$" should be -- $\Delta Z_k^{(m)}(\omega_j)$ --.

Column 14, Line 62, "$\Delta Z_k^{(m)}(\omega_j)$" should be -- $\Delta Z_k^{(m)}(\omega_j)$ --.

Column 14, Eq. (7a), "$\Delta Z_{k|k-1}^{(m)}(\omega_j) = \Delta Z_{k-1|k-1}^{(m)}(\omega_j)$" should be -- $\Delta Z_{k|k-1}^{(m)}(\omega_j) = \Delta Z_{k-1|k-1}^{(m)}(\omega_j)$ --.

Column 14, Eq. (7b), "$\sigma_{k|k-1,j}^{2,(m)} = \sigma_{k-1|k-1,j}^{2,(m)} + \sigma_{v,j}^{2,(m)}$" should be -- $\sigma_{k|k-1,j}^{2,(m)} = \sigma_{k-1|k-1,j}^{2,(m)} + \sigma_{v,j}^{2,(m)}$ --.

Column 15, Eq. (7c), "$\Delta Z_{k|k}^{(m)}(\omega_j) = \Delta Z_{k|k-1}^{(m)}(\omega_j) + C_{k,j}^{(m)}(Y_{k,j}^{(m),F} - \Delta Z_{k|k-1}^{(m)}(\omega_j))$" should be -- $\Delta Z_{k|k}^{(m)}(\omega_j) = \Delta Z_{k|k-1}^{(m)}(\omega_j) + C_{k,j}^{(m)}(Y_{k,j}^{(m),F} - \Delta Z_{k|k-1}^{(m)}(\omega_j))$ --.

Column 15, Eq. (7d), "$\sigma_{k|k,j}^{2,(m)} = (1 - C_{k,j}^{(m)})\sigma_{k|k-1,j}^{2,(m)}$" should be -- $\sigma_{k|k,j}^{2,(m)} = (1 - C_{k,j}^{(m)})\sigma_{k|k-1,j}^{2,(m)}$ --.

Column 15, Eq. (8), "$C_{k,j}^{(m)} = (\sigma_\varepsilon^{2,(m)} + \sigma_{k|k-1,j}^{2,(m)})^{-1} \sigma_{k|k-1,j}^{2,(m)}$" should be -- $C_{k,j}^{(m)} = (\sigma_\varepsilon^{2,(m)} + \sigma_{k|k-1,j}^{2,(m)})^{-1} \sigma_{k|k-1,j}^{2,(m)}$ --.

Column 15, Line 13, "$aZ_o^{(m)}(\omega_j)$ and $\sigma_{o,j}^{2,(m)}$" should be -- $aZ_o^{(m)}(\omega_j)$ and $\sigma_{o,j}^{2,(m)}$ --.

Column 15, Line 34, "$\sigma_{k|k-1,j}^{2,(m)}$" should be -- $\sigma_{k|k-1,j}^{2,(m)}$ --.

Column 15, Line 35, "$\sigma_\varepsilon^{2,(m)}$" should be -- $\sigma_\varepsilon^{2,(m)}$ --.

CERTIFICATE OF CORRECTION (continued)
U.S. Pat. No. 10,786,168 B2

Page 3 of 6

Column 15, Eq. (10), "$f_{k|k}^{SS-P}(\omega_j) = \|\Delta Z_{k|k}^{SS-P}(\omega_j)\|^2$" should be -- $f_{k|k}^{SS-P}(\omega_j) = \|\Delta Z_{k|k}^{SS-P}(\omega_j)\|^2$ --.

Column 15, Eq. (11), "$f_k^P(\omega_j) = \|Y_{k,j}^F\|^2$" should be -- $f_k^P(\omega_j) = \|Y_{k,j}^F\|^2$ --.

Column 15, Line 54, "$Y_k^F = (Y_{k,1}^F, \ldots, Y_{k,J}^F)'$" should be -- $Y_k^F = (Y_{k,1}^F, \ldots, Y_{k,j}^F)'$ --.

Column 15, Line 60, "$\Delta Z_{k|k}^{(m)}$" should be -- $\Delta Z_{k|k}^{(m)}$ --.

Column 15, Line 64, "$\Delta Z_{k|k} = M^{-1} \Sigma_{m-1}^M \Delta Z_{k|k}^{(m)}$" should be -- $\Delta Z_{k|k} = M^{-1} \sum_{m=1}^M \Delta Z_{k|k}^{(m)}$ --.

Column 16, Eq. (13), "$X_{k|k}^L = W \Delta Z_{k|k}^L$" should be -- $X_{k|k}^L = W \Delta Z_{k|k}^L$ --.

Column 16, Line 10, "$\Delta Z_{k|k}^L$" should be -- $\Delta Z_{k|k}^L$ --.

Column 16, Line 22-23, "$[(R_{k|k,t}^L)^2 + (l_{k|k,t}^L)^2]^{1/2}$" should be -- $[(R_{k|k,t}^L)^2 + (I_{k|k,t}^L)^2]^{1/2}$ --.

Column 16, Line 23, "$\tan(-1_{k|k,t}^L / R_{k|k,t}^L)$" should be -- $\tan(-I_{k|k,t}^L / R_{k|k,t}^L)$ --.

Column 16, Eq. (15), "
$$\Delta Z_{k|K}^{(m)}(\omega_j) = \Delta Z_{k|k}^{(m)}(\omega_j) +$$
$$A_{k,j}(\Delta Z_{k+1|K}^{(m)}(\omega_j) - \Delta Z_{k+1|k}^{(m)}(\omega_j))$$
$$\sigma_{k|K,j}^{2,(m)} = \sigma_{k|k,j}^{2,(m)} + A_{k,j}^2(\sigma_{k+1|K,j}^{2,(m)} - \sigma_{k+1|k,j}^{2,(m)})$$
$$A_{k,j} = \sigma_{k|k,j}^{2,(m)} (\sigma_{k+1|k,j}^{2,(m)})^{-1}$$
" should be
--
$$\Delta Z_{k|K}^{(m)}(\omega_j) = \Delta Z_{k|k}^{(m)}(\omega_j) +$$
$$A_{k,j}(\Delta Z_{k+1|K}^{(m)}(\omega_j) - \Delta Z_{k+1|k}^{(m)}(\omega_j))$$
$$\sigma_{k|K,j}^{2,(m)} = \sigma_{k|k,j}^{2,(m)} + A_{k,j}^2(\sigma_{k+1|K,j}^{2,(m)} - \sigma_{k+1|k,j}^{2,(m)})$$
$$A_{k,j} = \sigma_{k|k,j}^{2,(m)} (\sigma_{k+1|k,j}^{2,(m)})^{-1}$$
--.

Column 16, Line 41, "$\Delta Z_{K|K}^{(m)}(\omega_j)$" should be -- $\Delta Z_{K|K}^{(m)}(\omega_j)$ --.

Column 16, Line 42, "$\sigma_{K|K,j}^{2,(m)}$" should be -- $\sigma_{K|K,j}^{2,(m)}$ --.

Column 16, Eq. (16), "$\sigma_{k,u|K,j}^{(m)} = A_{k,j} \sigma_{k+1,u|K,j}^{(m)}$" should be -- $\sigma_{k,u|K,j}^{(m)} = A_{k,j} \sigma_{k+1,u|K,j}^{(m)}$ --.

Column 16, Line 59, "$\Delta Z_o^{(m)}(\omega_j)$" should be -- $\Delta Z_o^{(m)}(\omega_j)$ --.

CERTIFICATE OF CORRECTION (continued)
U.S. Pat. No. 10,786,168 B2

Column 16, Line 60, "$\sigma_{o,j}^{2,(m)}$" should be -- $\sigma_{o,j}^{2,(m)}$ --.

Column 16, Line 60, "$\sigma_{v,j}^{2,(m)}$ and $\sigma_\varepsilon^{2,(m)}$" should be -- $\sigma_{v,j}^{2,(m)}$ and $\sigma_\varepsilon^{2,(m)}$ --.

Column 17, Lines 1-2, "$Y_k^{r,(m),F}$ and $Y_k^{s,(m),F}$" should be -- $Y_k^{r,(m),F}$ and $Y_k^{s,(m),F}$ --.

Column 17, Line 4, "$\Delta Z_{k|k}^{r,(m)}(\omega_j)$ and $\Delta Z_{k|k}^{2,(m)}$" should be -- $\Delta Z_{k|k}^{r,(m)}(\omega_j)$ and $\Delta Z_{k|k}^{s,(m)}$ --.

Column 19, Line 26, "$\sigma_{v,l}^{2,(m)}$" should be -- $\sigma_{v,l}^{2,(m)}$ --.

Column 19, Line 29, "$C_{k,l}^{(m)}$" should be -- $C_{k,l}^{(m)}$ --.

Column 19, Eq. (21), "$\Delta Z_{k|k}^{(m)}(\omega_l) = (1 - C_{k,l}^{(m)})\Delta Z_{k-1|k-1}^{(m)}(\omega_l) + C_{k,l}^{(m)} Y_{k,l}^{(m),F}$" should be -- $\Delta Z_{k|k}^{(m)}(\omega_l) = (1 - C_{k,l}^{(m)})\Delta Z_{k-1|k-1}^{(m)}(\omega_l) + C_{k,l}^{(m)} Y_{k,l}^{(m),F}$ --.

Column 19, Line 41, "$Z_{k-1|k-1}^{(m)}(\omega_l)$" should be -- $Z_{k-1|k-1}^{(m)}(\omega_l)$ --.

Column 19, Line 41, "$Y_{k,l}^{(m),F}$" should be -- $Y_{k,l}^{(m),F}$ --.

Column 19, Line 45, "$Y_{k,l}^{(m),F}$" should be -- $Y_{k,l}^{(m),F}$ --.

Column 19, Line 46, "demise" should be --denoise--.

Column 20, Line 3, "$\Delta Z_{k|k}^{(m)}(\omega_l)$" should be -- $\Delta Z_{k|k}^{(m)}(\omega_l)$ --.

Column 20, Line 4, "$\leftarrow Z_{k-1|k-1}^{(m)}(\omega_l)$" should be -- $\Delta Z_{k-1|k-1}^{(m)}(\omega_l)$ --.

Column 20, Line 4, "$Y_{k,l}^{(m),F}$" should be -- $Y_{k,l}^{(m),F}$ --.

Column 21, Eq. (22), "$\Delta \overline{ff}_{r,s}(\omega) = 100^{-1}[\int_r \int_t^{SS-MT}(\omega)dt - \int_s \int_T^{SS-MT}(\omega)dt]$," should be -- $\Delta \overline{f}_{r,s}(\omega) = 100^{-1}\left[\int_r f_t^{SS-MT}(\omega)dt - \int_s f_t^{SS-MT}(\omega)dt\right]$ --.

Column 22, Line 11, "Awake1 and Awake1" should be --Awake2 and Awake1--.

CERTIFICATE OF CORRECTION (continued)
U.S. Pat. No. 10,786,168 B2

Column 24, Line 52, "$\Delta Z_k^{(m)}$" should be -- $\Delta Z_k^{(m)}$ --.

Column 24, Line 54, "$\Delta Z_k^{(m)}$" should be -- $\Delta Z_k^{(m)}$ --.

Column 24, Line 54, "$Y_{1:k}^{(m),F}$" should be -- $Y_{1:k}^{(m),F}$ --.

Column 24, Eq. (25), "$p(\Delta Z_k^{(m)} \mid Y_{1:k-1}^{(m),F}) = \int p(\Delta Z_{k-1}^{(m)} \mid Y_{1:k-1}^{(m),F}) p(\Delta Z_k^{(m)} \mid \Delta Z_{k-1}^{(m)}) d\Delta Z_{k-1}^{(m)}$," should be -- $p(\Delta Z_k^{(m)} \mid Y_{1:k-1}^{(m),F}) = \int p(\Delta Z_{k-1}^{(m)} \mid Y_{1:k-1}^{(m),F}) p(\Delta Z_k^{(m)} \mid \Delta Z_{k-1}^{(m)}) d\Delta Z_{k-1}^{(m)}$ --.

Column 25, Line 1, "$\Delta Z_k^{(m)}(\omega_j)$" should be -- $\Delta Z_k^{(m)}(\omega_j)$ --.

Column 25, Line 2, "$p(\Delta Z_k^{(m)(\omega_j)} \mid Y_{1:k-1,f}^{(m),F})$" should be -- $p(\Delta Z_k^{(m)}(\omega_j) \mid Y_{1:k-1,j}^{(m),F})$ --.

Column 25, Line 20, "$Y_{k,j}^{(m),F}$" should be -- $Y_{k,j}^{(m),F}$ --.

Column 25, Line 21, "$p(Y_{k,j}^{(m),F} \mid \Delta Z_k^{(m)}(\omega_j))$" should be -- $p(Y_{k,j}^{(m),F} \mid \Delta Z_k^{(m)}(\omega_j))$ --.

Column 25, Eq. (30), "$p(\Delta Z_k^{(m)} \mid Y_{1:k}^{(m),F}) \propto p(\Delta Z_k^{(m)} \mid Y_{1:k-1}^{(m),F}) p(Y_k^{(m),F} \mid \Delta Z_k^{(m)})$," should be -- $p(\Delta Z_k^{(m)} \mid Y_{1:k}^{(m),F}) \propto p(\Delta Z_k^{(m)} \mid Y_{1:k-1}^{(m),F}) p(Y_k^{(m),F} \mid \Delta Z_k^{(m)})$ --.

Column 25, Line 50, "$\Delta Z_k^{(m)} * (\omega_j)$" should be -- $\Delta Z_k^{(m)*}(\omega_j)$ --.

Column 25, Line 60, "$\Delta Z_{k|k}^{(m)}(\omega_j)$" should be -- $\Delta Z_{k|k}^{(m)}(\omega_j)$ --.

Column 26, Line 1, "$\sigma_{k|k,j}^{2,(m)}$" should be -- $\sigma_{k|k,j}^{2,(m)}$ --.

Column 26, Eq. (34), "$\sigma_{k|k,j}^{2(m)} = ((\sigma_{k|k-1,j}^{2,(m)})^{-1} + (\sigma_\varepsilon^{2,(m)})^{-1})^{-1}$" should be -- $\sigma_{k|k,j}^{2(m)} = \left((\sigma_{k|k-1,j}^{2,(m)})^{-1} + (\sigma_\varepsilon^{2,(m)})^{-1}\right)^{-1}$ --.

Column 26, Line 14, "$\Theta = \{\sigma_\varepsilon^{2,(m)}, \sigma_{v,j}^{2,(m)}, \Delta Z_o^{(m)}\}$," should be -- $\Theta = \{\sigma_\varepsilon^{2,(m)}, \sigma_{v,j}^{2,(m)}, \Delta Z_o^{(m)}\}$ --.

Column 26, Line 17, "$\Delta Z_{1:k}^{(m)}(\omega_j)$ and $Y_{1:K,j}^{(m),F}$" should be -- $\Delta Z_{1:k}^{(m)}(\omega_j)$ and $Y_{1:K,j}^{(m),F}$ --.

CERTIFICATE OF CORRECTION (continued)
U.S. Pat. No. 10,786,168 B2

Column 26, Eq. (38), "
$$\Delta Z_{k|K}^{(l)}(\omega j) = E[\Delta Z_k(\omega j) | Y_{1:K,j}^F, \Theta^{(l-1)}],$$
$$W_{k|K,j}^{(l)} = E[\|\Delta Z_k(\omega_j)\|^2 | Y_{1:K,j}^F, \Theta^{(l-1)}],$$
$$W_{k|k-1|K,j}^{(l)} = E[\Delta Z_k(\omega_j)\Delta Z_{k-1}^*(\omega_j) | Y_{1:K,j}^F, \Theta^{(l-1)}].$$
" should be $$\Delta Z_{k|K}^{(l)}(\omega_j) = E[\Delta Z_k(\omega_j) | Y_{1:K,j}^F, \Theta^{(l-1)}],$$
$$W_{k|K,j}^{(l)} = E[\|\Delta Z_k(\omega_j)\|^2 | Y_{1:K,j}^F, \Theta^{(l-1)}],$$
$$W_{k,k-1|K,j}^{(l)} = E[\Delta Z_k(\omega_j)\Delta Z_{k-1}^*(\omega_j) | Y_{1:K,j}^F, \Theta^{(t-1)}].$$
--.

Column 27, Line 1, "$\tau_{v,j}^{(l)} = 1/\sigma_{v,j}^{2,(l)}$" should be -- $\tau_{v,j}^{(l)} = 1/\sigma_{v,j}^{2,(l)}$ --.

Column 27, Line 2, "$\tau_\varepsilon^{(l)} = 1/\sigma_\varepsilon^{2,(l)}$" should be -- $\tau_\varepsilon^{(l)} = 1/\sigma_\varepsilon^{2,(l)}$ --.

Column 27, Line 10, "$\tau_{v,j}^{(l)}$ and $\tau_g^{(l)}$" should be -- $\tau_{v,j}^{(l)}$ and $\tau_\varepsilon^{(l)}$ --.

Column 27, Eq. 40,
"$E[\log p(\tau_\varepsilon^{(l)}, \tau_{v,j}^{(l)} | Y_{1:K,j}^F, \Theta^{l-1}] \propto \log(p(\tau_\varepsilon^{(l)} | \alpha, \beta)) + \log(p(\tau_{v,j}^{(l)} | \alpha, \beta)) + E[\log L_j^{(l)}]$" should be
-- $E[\log p(\tau_\varepsilon^{(l)}, \tau_{v,j}^{(l)}) | Y_{1:K,j}^F, \Theta^{l-1}] \propto \log(p(\tau_\varepsilon^{(l)} | \alpha, \beta)) + \log(p(\tau_{v,j}^{(l)} | \alpha, \beta)) + E[\log L_j^{(l)}]$ --.

Column 27, Line 15, "$\tau_{v,j}^{(l)}$ and $\tau_\varepsilon^{(l)}$" should be -- $\tau_{v,j}^{(l)}$ and $\tau_\varepsilon^{(l)}$ --.

Column 27, Eq. (41), "
$$\tau_{v,j}^{(l)} = \frac{K+\alpha}{2\sum_{k=1}^{K}\left(W_{k-1|K,j}^{(l)} - \Re\{W_{k,k-1|K,j}^{(l)}\}\right) + W_{K|K,j}^{(l)} + \beta},$$
$$\tau_\varepsilon^{(l)} = \frac{\alpha - 1 + JK}{\left(\left(Y_{k,j}^{P,(l)}\right)^2 + W_{k|K,j}^{(l)} - 2\Re\{Y_{k,j}^{F,(l)*}\Delta Z_{k|K,j}^{(l)}\}\right) + \beta}$$
" should be
--
$$\tau_{v,j}^{(l)} = \frac{K+\alpha}{2\sum_{k=1}^{K}\left(W_{k-1|K,j}^{(l)} - \Re\{W_{k,k-1|K,j}^{(l)}\}\right) + W_{K|K,j}^{(l)} + \beta},$$
$$\tau_\varepsilon^{(l)} = \frac{\alpha - 1 + JK}{\sum_{k,j}\left(\left(Y_{k,j}^{F,(l)}\right)^2 + W_{k|K,j}^{(l)} - 2\Re\{Y_{k,j}^{F,(l)*}\Delta Z_{k|K,j}^{(l)}\}\right) + \beta}$$
--.

Column 27, Lines 30-31, "$\|\Delta Z_{k|K}^{(l)} - \Delta Z_{k|K}^{(l-1)}\|^{2/}\|\Delta Z_{k|K}^{((l-1)}\|^2 < \varepsilon$" should be
-- $\|\Delta Z_{k|K}^{(l)} - \Delta Z_{k|K}^{(l-1)}\|^2 / \|\Delta Z_{k|K}^{(l-1)}\|^2 < \varepsilon$ --.